United States Patent [19]

Bruderer et al.

[11] Patent Number: 5,318,967

[45] Date of Patent: Jun. 7, 1994

[54] 2,3,3A,4,5,9B-HEXAHYDRO-1H-BENZO[E]INDOLE DERIVATIVES

[75] Inventors: Hans Bruderer, Biel-Benken; Thierry Godel, Reinach; René Imhof, Gipf-Oberfrick, all of Switzerland; Roland Jakob-Roetne, Inzlingen, Fed. Rep. of Germany

[73] Assignee: Hoffmann-La Roche Inc., Nutley, N.J.

[21] Appl. No.: 118,831

[22] Filed: Sep. 3, 1993

Related U.S. Application Data

[63] Continuation of Ser. No. 989,242, Dec. 11, 1992, abandoned.

[30] Foreign Application Priority Data

Dec. 20, 1991 [CH] Switzerland .................. 3806/91
Oct. 19, 1992 [CH] Switzerland .................. 3254/92

[51] Int. Cl.$^5$ .............. A61K 31/40; A61K 31/535; C07D 209/56; C07D 413/06
[52] U.S. Cl. .................. 514/232.8; 514/323; 514/411; 544/142; 546/200; 548/428
[58] Field of Search ............ 544/142; 546/200; 548/427; 514/232.8, 323, 411

[56] References Cited

FOREIGN PATENT DOCUMENTS 2044172 9/1970 Denmark .
2235667 7/1972 Denmark .
041488 5/1981 European Pat. Off. .
0127597 4/1984 European Pat. Off. .
016862 4/1974 Japan .
WO9015047 12/1990 World Int. Prop. O. .
WO91/00856 1/1991 World Int. Prop. O. .

OTHER PUBLICATIONS

Ellmann et al. Biochem. Pharmacol. 7, 1961, 88.
Johnson et al. Analytical Biochemistry 64, 1975 229.
Weber et al. Proc. Natl. Acad. Sci. USA 83, 1986, 8784.
Watson et al. Pharmacol. Exp. Ther. 237 (1986) 419.
Eberlein et al. Trends Pharmacol. Science 10 (1989) 50.
Kilbinger et al. Eur. J. Pharmacol. 103 (1984) 313.
J. Pharm. Pharmacol 1991, 43:11–16.
Chim.Ther.–Recherches dans la serie des aryl-3 pyrrolidines III. Preparation de derives du benzo(e) indole et de l'indano(1,2b)pyrrole 450–458 (1972).

Primary Examiner—Robert W. Ramsuer
Attorney, Agent, or Firm—George M. Gould; William G. Isgro

[57] ABSTRACT

The invention relates to cis-2,3,3a,4,5,9b-Hexahydro-1H-benzo[b]indole derivatives of the formula

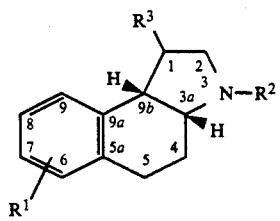

wherein $R^1$ is a residue of the formula —O—CO—NR$^4$R$^5$, $R^2$ is lower alkyl, lower cycloalkyl or lower alkyl substituted by lower cycloalkyl, aryl, aroyl, aroylamino, amino or by a cyclic amino, amide or imide group, $R^3$ is hydrogen or lower alkyl, $R^4$ is lower alkyl and $R^5$ is hydrogen or lower alkyl, the corresponding trans isomers or cis-trans isomeric mixtures and pharmaceutically acceptable salts thereof. These compounds and salts are especially suitable for the treatment or prophylaxis of cognitive disorders and senile dementia particularly, Alzheimer's disease, and for the improvement of memory capacity.

27 Claims, No Drawings

2,3,3A,4,5,9B-HEXAHYDRO-1H-BENZO[E]INDOLE DERIVATIVES

This is a continuation of application Ser. No. 07/989,242 filed Dec. 11, 1992 now abandoned.

BRIEF SUMMARY OF THE INVENTION

The invention relates to indole derivatives. In particular, it relates to cis-2,3,3a,4,5,9b-hexahydro-1H-benzo[e]indole derivatives of the formula

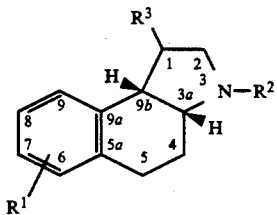

wherein $R^1$ is a residue of the formula —O—CO—$NR^4R^5$, $R^2$ is lower alkyl, lower cycloalkyl or lower alkyl substituted by lower cycloalkyl, aryl, aroyl, aroylamino, amino or by a cyclic amino, amide or imide group, $R^3$ is hydrogen or lower alkyl, $R^4$ is lower alkyl and $R^5$ is hydrogen or lower alkyl, the corresponding trans isomers or cis-trans isomeric mixtures and pharmaceutically acceptable salts thereof.

The compounds of formula I and salts thereof are distinguished by valuable therapeutic properties. In particular, they are suitable for the treatment or prophylaxis of cognitive disorders and senile dementia (especially Alzheimer's disease) and for the improvement of memory capacity.

DETAILED DESCRIPTION OF THE INVENTION

The invention relates to indole derivatives. In particular, it relates to cis-2,3,3a,4,5,9b-hexahydro-1H-benzo[e]indole derivatives of the formula

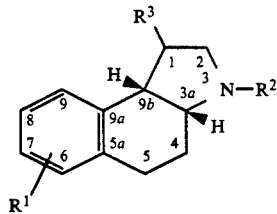

wherein $R^1$ is a residue of the formula —O—CO—$NR^4R^5$, $R^2$ is lower alkyl, lower cycloalkyl or lower alkyl substituted by lower cycloalkyl, aryl, aroyl, aroylamino, amino or by a cyclic amino, amide or imide group, $R^3$ is hydrogen or lower alkyl, $R^4$ is lower alkyl and $R^5$ is hydrogen or lower alkyl, the corresponding trans isomers or cis-trans isomeric mixtures and pharmaceutically acceptable salts thereof.

The compounds of formula I and salts thereof are distinguished by valuable therapeutic properties. In particular, they are suitable for the treatment or prophylaxis of cognitive disorders and senile dementia (especially Alzheimer's disease) and for the improvement of memory capacity.

Objects of the invention are the compounds of formula I as well as corresponding trans isomers or cis-trans isomer mixtures and pharmaceutically acceptable salts thereof, the manufacture thereof, medicaments containing them and the manufacture thereof, as well as the use thereof for the treatment or prophylaxis of cognitive disorders and senile dementia (especially Alzheimer's disease) and for the improvement of memory capacity and, respectively, for the manufacture of medicaments for the stated indications.

As used herein, the term "lower alkyl" shall mean straight-chain or branched saturated hydrocarbon residues with up to 7 carbon atoms, such as, methyl, ethyl, n-propyl, isopropyl, n-butyl, sec.butyl, isobutyl, n-pentyl, n-hexyl and the like.

The term "lower cycloalkyl" shall mean cyclic saturated hydrocarbon residues with up to 7 carbon atoms, such as, cyclopentyl, cyclohexyl and the like.

The terms "aryl" and "aroyl" shall mean optionally substituted phenyl and, respectively, benzoyl residues, which may be substituted, for example, by 1 to 3 lower alkoxy groups (such as methoxy), lower alkanesulfonyl groups (such as methane-sulfonyl), halogens (such as fluorine) and the like, examples of the substitution pattern are 4-methoxy-, 3,4-dimethoxy-, 4-fluoro-, 4-methanesulfonyl- and the like.

The terms "cyclic amino group", "cyclic amide group" and "cyclic imide group" shall mean 5- or 6-membered heterocyclic residues which are attached via the nitrogen atom, which can contain an additional hetero atom and/or which can be substituted and/or which can be fused. Oxygen preferably comes into consideration as the additional hetero atom and one or two lower alkyl groups, such as methyl, preferably come into consideration as substituents; in addition to the heterocyclic residue fused residues contain preferably a benzene ring which can be hydrogenated and/or substituted, preferably by halogen (preferably one or two chlorine atoms), nitro, hydroxy or pyridyl.

Piperidin-1-yl, morpholin-4-yl, 1-oxoisoindolin-2-yl, 1,3-dioxoisoindolin-2-yl, 1,3-dioxo-octahydro-cis-isoindolin-2-yl, 4,4-dimethyl-2,6-dioxopiperidin-1-yl and the like are examples of cyclic amino, amide and imide groups.

When, in the compounds of formula I or in the corresponding trans isomers $R^3$ is hydrogen and neither $R^1$ nor $R^2$ has an asymmetric center, the compounds of the invention can exist as enantiomers, otherwise various diastereomer pairs of enantiomers are possible. The invention embraces all possible stereoisomers as well as mixtures thereof, preferably cis-trans mixtures and/or racemates.

$R^1$ is situated, for example, in the 6- or 9-position of the tricyclic ring structure. In the residue $R^1$ represented by the formula —O—CO—$NR^4R^5$, for example, $R^4$ can be methyl, ethyl, propyl or butyl and $R^5$ can be hydrogen or $R^4$ can be methyl and $R^5$ can be ethyl or $R^4$ and $R^5$ can both be methyl.

$R^2$ can be, for example, n-propyl, 3-methylbutyl, cyclo-pentyl, cyclohexylmethyl, 2-cyclohexylethyl, 3-cyclohexylpropyl, 4-cyclohexylbutyl, 2-cyclopentylethyl, benzyl, 2-phenylethyl, 3-phenylpropyl, 3-benzoylpropyl, 4-benzoylbutyl, 3-(4-methoxybenzoyl)propyl, 4-(3,4-dimethoxybenzoyl)butyl, 5-(3,4-di-methoxybenzoyl)pentyl, 3-(4-fluorobenzoyl)propyl, 4-benzoylaminobutyl, 5-benzoylaminopentyl, 6-benzoylaminohexyl, 4-(4-methanesulfonylbenzoylamino)-butyl, 5-(4-methanesulfonylbenzoylamino)pentyl, 6-(4-methanesulfonylbenzoylamino)hexyl, 4-aminobutyl, 5-aminopentyl, 6-aminohexyl, 2-morpholin-4-ylethyl, 3-morpholin-4-ylpropyl, 2-piperidin-1-ylethyl, 3-piperidin-1-ylpropyl, 4-(1,3-dioxoisoindolin-1-yl)butyl, 5-(1,3-dioxoisoindolin-1-yl)pentyl, 6-(1,3-dioxoisoindolin-1-yl)hexyl, 5-(1,3-dioxo-octahydro-cis-isoindolin-2-yl)pentyl, 4-(4,4-dimethyl-2,6-dioxopiperidin-1-yl)butyl, 5-(4,4-dimethyl-2,6-dioxo-piperidin-1-yl)pentyl, 6-(4,4-dimethyl-2,6-dioxopiperidin-1-yl)hexyl, 4-(1-oxoisoindolin-2-yl)butyl, 5-(1-oxoisoindolin-2-yl)pentyl or 6-(1-oxoisoindolin-2-yl)pentyl.

$R^3$ can be, for example, hydrogen or methyl.

Preferred compounds of formula I are:

(+)-cis-3-(2-Cyclohexylethyl)-2,3,3a,4,5,9b-hexahydro-1H-benzo[e]indol-6-yl dimethylcarbamate, (−)-cis-3-(2-cyclohexylethyl)-2,3,3a,4,5,9b-hexahydro-1H-benzo[e]indol-6-yl dimethylcarbamate, rac-cis-3-(2-cyclohexylethyl)-2,3,3a,4,5,9b-hexahydro-1H-benzo[e]indol-6-yl dimethylcarbamate, rac-cis-2,3,3a,4,5,9b-hexahydro-3-(4-phthalimidobutyl)-1H-benzo[e]indol-6-yl dimethylcarbamate, rac-cis-2,3,3a,4,5,9b-hexahydro-3-(6-phthalimidohexyl)-1H-benzo[e]indol-6-yl dimethylcarbamate, rac-cis-2,3,3a,4,5,9b-hexahydro-3-(2-morpholinoethyl)-1H-benzo[e]indol-6-yl dimethylcarbamate, rac-2,3,3aα,4,5,9bα-hexahydro-1α-methyl-3-propyl-1H-benzo[e]indol-6-yl dimethylcarbamate, rac-cis-2,3,3a,4,5,9b-hexahydro-3-propyl-1H-benzo[e]indol-9-yl dimethylcarbamate, (+)-3-(2-cyclohexylethyl)-cis-2,3,3a,4,5,9b-hexahydro-1H-benzo[e]indol-6-yl methylcarbamate, (+)-3-(2-cyclohexylethyl)-cis-2,3,3a,4,5,9b-hexahydro-1H-benzo[e]indol-6-yl propylcarbamate, (+)-3-(2-cyclohexylethyl)-cis-2,3,3a,4,5,9b-hexahydro-1H-benzo[e]indol-6-yl ethylmethylcarbamate, rac-3-cyclohexylmethyl-cis-2,3,3a,4,5,9b-hexahydro-1H-benzo[e]indol-6-yl dimethylcarbamate, rac-3-(3-cyclohexylpropyl)-cis-2,3,3a,4,5,9b-hexahydro-1H-benzo[e]indol-6-yl dimethylcarbamate, rac-3-(4-cyclohexylbutyl)-cis-2,3,3a,4,5,9b-hexahydro-1H-benzo[e]indol-6-yl dimethylcarbamate and rac-3-(2-cyclopentylethyl)-cis-2,3,3a,4,5,9b-hexahydro-1H-benzo[e]indol-6-yl dimethylcarbamate.

Exemplary of additional compounds of formula I are:

(+)-3-(2-Cyclohexylethyl)-cis-2,3,3a,4,5,9b-hexahydro-1H-benzo[e]indol-6-yl ethylcarbamate, rac-3-(2-cyclohexylethyl)-cis-2,3,3a,4,5,9b-hexahydro-1H-benzo[e]indol-6-yl butylcarbamate, rac-3-(3-methylbutyl)-cis-2,3,3a,4,5,9b-hexahydro-1H-benzo[e]indol-6-yl dimethylcarbamate, rac-3-phenethyl-cis-2,3,3a,4,5,9b-hexahydro-1H-benzo[e]indol-6-yl dimethylcarbamate, rac-3-propyl-cis-2,3,3a,4,5,9b-hexahydro-1H-benzo[e]indol-6-yl dimethylcarbamate, rac-3-(3-phenylpropyl)-cis-2,3,3a,4,5,9b-hexahydro-1H-benzo[e]indol-6-yl dimethylcarbamate, rac-3-(3-morpholin-4-yl-propyl)-cis-2,3,3a,4,5,9b-hexahydro-1H-benzo[e]indol-6-yl dimethylcarbamate, rac-3-(2-piperidin-1-yl-ethyl)-cis-2,3,3a,4,5,9b-hexahydro-1H-benzo[e]indol-6-yl dimethylcarbamate, rac-3-(3-piperidin-1-yl-propyl)-cis-2,3,3a,4,5,9b-hexahydro-1H-benzo[e]indol-6-yl dimethylcarbamate, rac-3-[5-(1,3-dioxo-isoindolin-2-yl)-pentyl]-cis-2,3,3a,4,5,9b-hexahydro-1H-benzo[e]indol-6-yl dimethylcarbamate, rac-3-[4-(1-oxo-isoindolin-2-yl)-butyl]-cis-2,3,3a,4,5,9b-hexahydro-1H-benzo[e]indol-6-yl dimethylcarbamate, rac-3-[5-(1-oxo-isoindolin-2-yl)-pentyl]-cis-2,3,3a,4,5,9b-hexahydro-1H-benzo[e]indol-6-yl dimethylcarbamate, rac-3-[6-(1-oxo-isoindolin-2-yl)-hexyl]-cis-2,3,3a,4,5,9b-hexahydro-1H-benzo[e]indol-6-yl dimethylcarbamate, rac-3-(3-benzoyl-propyl)-cis-2,3,3a,4,5,9b-hexahydro-1H-benzo[e]indol-6-yl dimethylcarbamate, rac-3-(4-benzoyl-butyl)-cis-2,3,3a,4,5,9b-hexahydro-1H-benzo[e]indol-6-yl dimethylcarbamate, rac-3-[3-(4-methoxy-benzoyl)-propyl]-cis-2,3,3a,4,5,9b-hexahydro-1H-benzo[e]indol-6-yl dimethylcarbamate, rac-3-[4-(3,4-dimethoxy-benzoyl)-butyl]-cis-2,3,3a,4,5,9b-hexahydro-1H-benzo[e]indol-6-yl dimethylcarbamate, rac-3-[5-(3,4-dimethoxy-benzoyl)-pentyl]-cis-2,3,3a,4,5,9b-hexahydro-1H-benzo[e]indol-6-yl dimethylcarbamate, rac-3-[4-(4,4-dimethyl-2,6-dioxo-piperidin-1-yl)-butyl]-cis-2,3,3a,4,5,9b-hexahydro-1H-benzo[e]indol-6-yl dimethylcarbamate, rac-3-[5-(4,4-dimethyl-2,6-dioxo-piperidin-1-yl)-pentyl]-cis-2,3,3a,4,5,9b-hexahydro-1H-benzo[e]indol-6-yl dimethylcarbamate, rac-3-[6-(4,4-dimethyl-2,6-dioxo-piperidin-1-yl)-hexyl]-cis-2,3,3a,4,5,9b-hexahydro-1H-benzo[e]indol-6-yl dimethylcarbamate, rac-3-[3-(4-fluoro-benzoyl)-propyl]-cis-2,3,3a,4,5,9b-hexahydro-1H-benzo[e]indol-6-yl dimethylcarbamate, rac-N-[4-(6-dimethylcarbamoyloxy)-cis-2,3,3a,4,5,9b-hexahydro-1H-benzo[e]indol-3-yl)-butyl]-4-methanesulphonylbenzamide, rac-N-[5-(6-dimethylcarbamoyloxy)-cis-2,3,3a,4,5,9b-hexahydro-1H-benzo[e]indol-3-yl)-pentyl]-4-methanesulphonylbenzamide, rac-N-[6-(6-dimethylcarbamoyloxy)-cis-2,3,3a,4,5,9b-hexahydro-1H-benzo[e]indol-3-yl)-hexyl]-4-methanesulphonylbenzamide, rac-N-[4-(6-dimethylcarbamoyloxy)-cis-2,3,3a,4,5,9b-hexahydro-1H-benzo[e]indol-3-yl)-butyl]-benzamide, rac-N-[5-(6-dimethylcarbamoyloxy)-cis-2,3,3a,4,5,9b-hexahydro-1H-benzo[e]indol-3-yl)-pentyl]-benzamide, rac-N-[6-(6-dimethylcarbamoyloxy)-cis-2,3,3a,4,5,9b-hexahydro-1H-benzo[e]indol-3-yl)-hexyl]-benzamide, rac-cis-(3-cyclopentylpropyl)-2,3,3a,4,5,9b-hexahydro-1H-benzo[e]indol-6-yl dimethylcarbamate, rac-cis-3-cyclopentyl-2,3,3a,4,5,9b-hexahydro-1H-benzo[e]indol-6-yl dimethylcarbamate, rac-3-(4-aminobutyl)-2,3,3a,4,5,9b-hexahydro-1H-cis-benzo[e]indol-6-yl dimethylcarbamate, rac-3-(5-aminopentyl)-2,3,3a,4,5,9b-hexahydro-1H-cis-benzo[e]indol-6-yl dimethylcarbamate, rac-3-(6-aminohexyl)-2,3,3a,4,5,9b-hexahydro-1H-cis-benzo[e]indol-6-yl dimethylcarbamate, rac-3-benzyl-2,3,3a,4,5,9b-hexahydro-1H-cis-benzo[e]indol-6-yl dimethylcarbamate, rac-3-[5-(1,3-dioxo-octahydro-cis-isoindol-2-yl)pentyl]-2,3,3a,4,5,9b-hexahydro-1H-cis-benzo[e]indol-6-yl dimethylcarbamate, rac-3-[5-(1,3-dioxoisoindolin-2-yl)pentyl]-2,3,3a,4,5,9b-hexahydro-1H-cis-benzo[e]indol-6-yl ethylcarbamate and (+)-trans-3-(2-cyclohexylethyl)-2,3,3a,4,5,9b-hexahydro-1H-benzo[e]indol-6-yl dimethylcarbamate.

The compounds of formula I or the corresponding trans isomers or cis-trans isomer mixtures and their pharmaceutically acceptable acid addition salts can be manufactured in accordance with the invention by a) acylating a compound of the formula

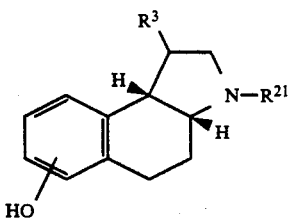
II wherein $R^3$ has the significance given above and $R^{21}$ has in principle the significance given above for $R^2$, but can not be lower alkyl substituted by amino,
or the corresponding trans isomer or cis-trans isomer mixture with an agent yielding a residue of the formula —CO—$NR^4R^5$, wherein $R^4$ and $R^5$ have the significance given above, or b) converting a compound of the formula

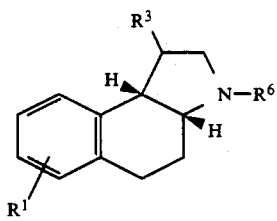
III wherein $R^1$ and $R^3$ have the significance given above and $R^6$ is lower alkyl substituted by a residue convertible into an amino group,
or the corresponding trans isomer or cis-trans isomer mixture into a corresponding compound of formula I or the corresponding trans isomer or cis-trans isomer mixture in which $R^2$ is lower alkyl substituted by amino; or c) appropriately acylating the amino group in a compound of formula I in which $R^2$ is lower alkyl substituted by amino or in a corresponding trans isomer or cis-trans isomer mixture;

d) if desired, separating a cis-trans isomer mixture and/or a mixture of diastereomers obtained; and/or e) if desired, resolving a racemate obtained; and/or f) if desired, converting a compound of formula I or a corresponding trans isomers or cis-trans isomer mixture obtained into a pharmaceutically acceptable acid addition salt.

For the acylation of the phenolic hydroxyl group in the compounds of formula II or in the corresponding trans isomers or cis-trans isomer mixtures, there are conveniently used corresponding carbamoyl chlorides, such as, dimethylcarbamoyl chloride, ethylmethylcarbamoyl chloride or the like, or corresponding isocyanates, such as, methyl isocyanate, ethyl isocyanate, propyl isocyanate, butyl isocyanate or the like. When such acylating agents are used, the acylation is conveniently effected in the presence of an organic solvent which is inert under the reaction conditions, for example, an aromatic hydrocarbon, such as, toluene, in a halogenated hydrocarbon, such as, 1,1,2-trichloroethane and the like.

Furthermore, the acylation is conveniently effected in the presence of 4-dimethylaminopyridine and of base(s), whereby organic bases, such as, trialkylamines, pyridine and the like, primarily come into consideration as bases. The reaction temperature and reaction time are governed by the remaining reaction parameters; in general boiling at reflux for about 1 to 30 hours should be appropriate.

Apart from carbamoyl chlorides and, respectively, isocyanates, mixtures of bis-(trichloromethyl)-carbonate and corresponding monoalkylamines and dialkylamines are also suitable acylating agents.

The substituent denoted by the symbol $R^6$ in formula III contains a residue which can be converted into an amino group. Protected amino groups, for example, acylated amino groups, such as, phthalimido or the like, primarily come into consideration as such residues.

Methods by which groups of the type described previously can be converted into an amino group will be familiar to any person skilled in the art. Furthermore, it will also be evident to any person skilled in the art that there come into consideration only those groups which on the one hand can be converted into an amino group by methods which do not affect other groupings in the molecule and which on the other hand remain unaffected under the reaction conditions used for the synthesis of the compounds of formula III or the corresponding trans isomers or cis-trans isomer mixtures.

The phthalimido group is conveniently converted into an amino group by reaction with hydrazine in ethanol.

The acylation of an amino group present in the substituent $R^2$ is carried out according to methods which are known and which will be familiar to any person skilled in the art, for example, by reaction with a reactive functional derivative of the carboxylic acid corresponding to the acyl residue to be introduced, such as, benzoyl chloride, in the presence of a base, such as, triethylamine or the like, or with the corresponding free carboxylic acid such as 4-(methanesulphonyl)benzoic acid in the presence of a suitable condensation agent, such as, 2(1Hbenzo-triazol-1-yl)-1,1,3,3-tetramethyluronium hexafluorophosphate or the like and a base such as triethylamine or the like.

The separation of cis-trans mixtures and of mixtures of diastereomers as well as the resolution of racemates can be effected according to generally usual methods, whereby it can be convenient to carry this out not only on the compounds of formula I or on corresponding trans isomers or cis-trans isomer mixtures, but already at an earlier stage of the synthesis, for example, at the stage of the compounds of formula II or the corresponding trans isomers or cis-trans isomer mixtures.

The preparation of pharmaceutically acceptable acid addition salts of compounds of formula I or of corresponding trans-isomers or cis-trans isomer mixtures can be effected according to methods which are generally conventional and which will be familiar to any person skilled in the art. There come into consideration not only salts with inorganic acids, but also with organic acids, for example, hydrochlorides, hydrobromides, sulfates, methanesulfonates, p-toluenesulfonates, oxalates, tartrates, citrates, maleates, ascorbates, acetates and the like.

The preparation of the starting materials of formula II and, respectively, of corresponding trans isomers or cis-trans isomer mixtures (which belong to a class of compounds known in principle from WO 91/00856) is illustrated generally hereinafter on the basis of a Reaction Scheme; furthermore, a number of the Examples presented hereinafter contain detailed information concerning the preparation of specific compounds of formula II and, respectively, of corresponding trans isomers or cis-trans isomer mixtures. Thereby, methods which are known and which will be familiar to any person skilled in the art are used throughout.

IV→V

The methoxytetralone of formula IV is first converted by means of pyrrolidine, piperidine, morpholine or another secondary amine such as dimethylamine or diethylamine into an enamine and this is subsequently reacted with iodoacetamide.

V→VI

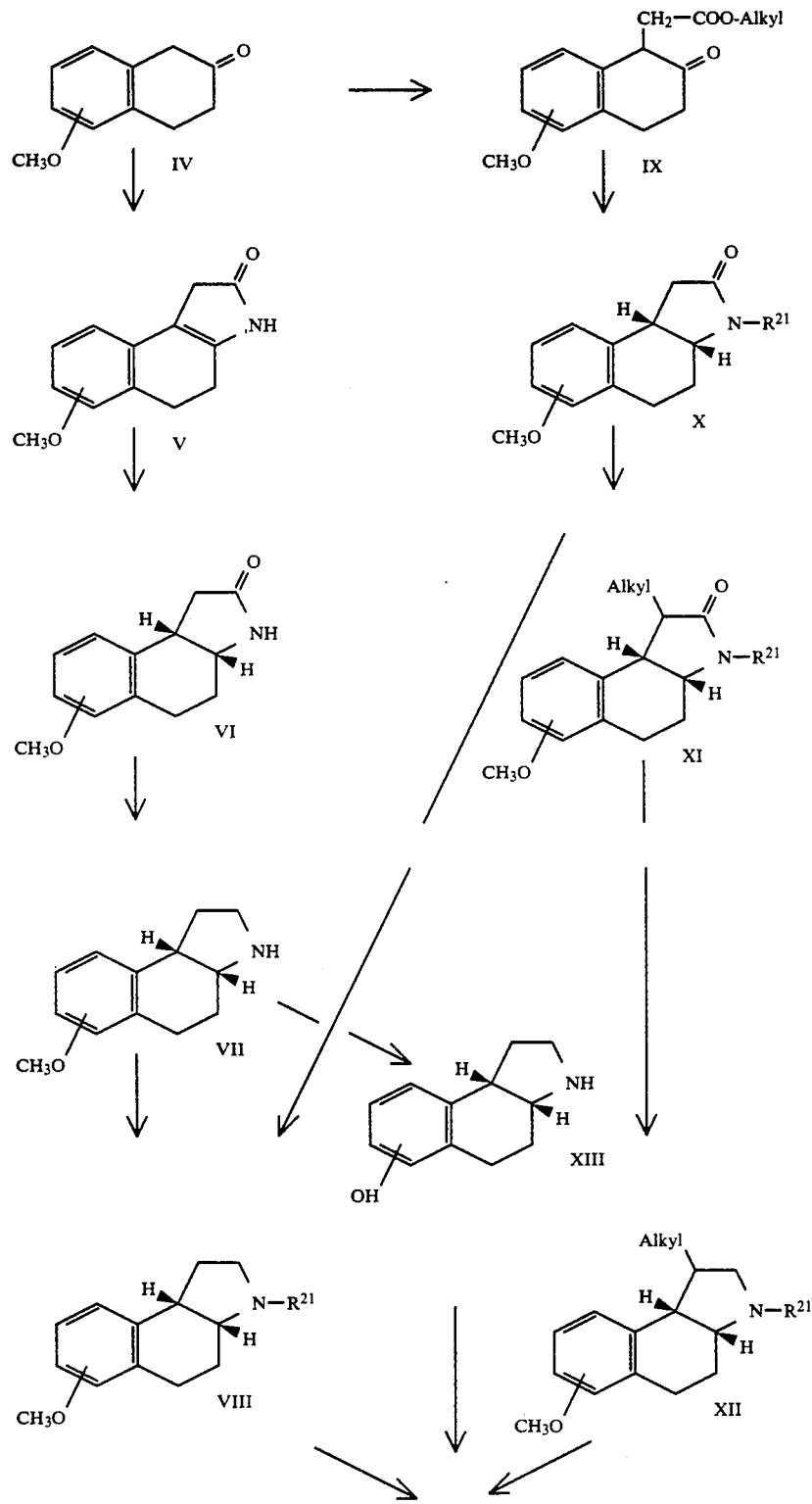

The reduction of the double bond is conveniently effected using triethylsilane and trifluoroacetic acid in an organic solvent which is inert under the reaction conditions, for example in a chlorinated hydrocarbon such as methylene chloride; thereby in addition to the compound of formula VI there can also result the corresponding trans isomer, although only in a relatively small amount (about 5-10%). The reduction of the double bond can, however, also be carried out by catalytic hydrogenation, for example, in the presence of Raney nickel; thereby the cis compound of formula VI results exclusively.

VI→VII

The reduction of the oxo group to the methylene group is conveniently effected with a complex metal hydride in an organic solvent which is inert under the reaction conditions, for example, with lithium aluminum hydride in tetrahydrofuran.

VII→VIII

The N-substitution is conveniently effected with a chloride or bromide of the formula $R^{21}$-Cl or $R^{21}$-Br in the presence of a base, such as, potassium carbonate and an alkali metal iodide, such as, sodium iodide in an organic solvent which is inert under the reaction conditions, for example, in a ketone such as acetone, methyl ethyl ketone or the like. The reaction can also be effected, for example, in toluene or the like in the presence of an organic base such as triethylamine or the like.

The N-acylation can also be effected by first acylating the nitrogen atom, for example, using cyclopentylacetyl chloride, cyclopentylpropionyl chloride, propionyl chloride or the like and then reducing the acylation product using lithium aluminum hydride or the like.

When the substituent $R^{21}$, which is introduced, contains a phthalimido group, then this can be cleaved and the free amino group can be subsequently acylated in an analogous manner to that described above in connection with process variants b) and c). A phthalimido group present in an introduced residue $R^{21}$ can also be reduced. Reduction with zinc in acetic acid yields a 1-oxo-isoindol-2-yl compound and catalytic hydrogenation, for example, over Pd/C in glacial acetic acid, yields a mixture of a 1-oxoiso-indolin2-yl compound and a corresponding 1,3-dioxo-octahydro-cis-isoindol-2-yl compound.

In the event that $R^2$ in the end product contains a phenyl group which is mono- or disubstituted by methoxy, as in the case of 4-(3,4-dimethoxybenzoyl)butyl or 5-(3,4-dimethoxybenzoyl)pentyl, then the corresponding N-substitution is effected only after the ether cleavage, that is, the sequence VII→XIII→II is carried out in place of the sequence VII→VIII→II.

VII→XIII

The ether cleavage is conveniently effected using hydrobromic acid in water or using boron tribromide in methylene chloride or using pyridine hydrochloride.

XIII→II

The N-substitution is conveniently effected with a corresponding bromide, such as, 5-bromo-3',4'-dimethoxyvalero-phenone, 6-bromo-(3,4-dimethoxyphenyl)-hexan-1-one or the like in the presence of a base, such as, triethylamine or the like in an inert organic solvent, such as, toluene or the like.

IV→IX

The methoxytetralone of formula IV is first converted—analogously to that described in step IV→V—into an enamine and this is then reacted with an alkyl bromoacetate.

IX→X

The compound of formula IX is reacted with an amine of the formula $R^{21}$-$NH_2$, whereupon the product obtained is reduced, conveniently by hydrogenation in the presence of Raney-nickel. The reduction can, however, also be effected using triethylsilane and trifluoroacetic acid, whereby, in addition to the compound of formula X, there can also result to a lesser extent the corresponding trans isomer.

X→VIII

The reduction of the oxo group to the methylene group is effected analogously to that described in step VI→VII.

X→XI

The alkylation in the 1-position is conveniently effected with a corresponding alkyl halide such as methyl iodide after deprotonization with a strong base such as lithium diisopropylamide.

XI→XII

The reduction of the oxo group to the methylene group is effected analogously to that described in step VI→VII.

VIII or XII→II

The ether cleavage is conveniently effected with hydrogen bromide in water or using bromine tribromide in methylene chloride or using pyridine hydrochloride.

The preparation of the compounds of formula III or the corresponding trans isomers or cis-trans isomeric mixtures is effected analogously to that of the compounds of formula I or the corresponding trans isomers or cis-trans isomeric mixtures, that is, in analogy to the foregoing Reaction Scheme and to process variant a) described previously.

As mentioned earlier, the compounds of formula I as well as corresponding trans isomers or cis-trans isomeric mixtures and their pharmaceutically usable or acceptable acid addition salts possess valuable pharmacodynamic properties. They have the capacity to inhibit the enzyme acetylcholine esterase and thereby to increase the acetylcholine level in the brain. They are therefore suitable for the treatment or prophylaxis of cognitive disorders and senile dementia, especially Alzheimer's disease, and for improving memory capacity.

The determination of the acetylcholine esterase inhibition was effected according to the method of Ellmann et al., Biochem. Pharmacol. 7 (1961) 88, and/or according to the method of Johnson et al., Analytical Biochemistry 64 (1975), 229. The following Table contains, for representative compounds of formula I and for the standard preparation physostigmin, data concerning the IC 50 values for acetylcholine esterase inhibition in nM/l as well as data concerning their toxicity, LLD, that is, "lowest lethal dose" in mg/kg, whereby route of administration and kind of animal are given.

| Compound | IC 50 | LLD |
|---|---|---|
| Physostigmin | 18 | 1 sc rat |
| A | 22 | 30 sc rat |
| B | 30 | 30 sc rat |
| C | 16 | 30 ip rat |
| D | 1.4 | 3 ip rat |
| E | 0.4 | 10 sc rat |
| F | 108 | 30 sc rat |
| G | 350 | 125 po mouse |

-continued

| Compound | IC 50 | LLD |
|---|---|---|
| H | 488 | 100 sc rat |

A = (+)-cis-3-(-Cyclohexylethyl)-2,3,3a,4,5,9b-hexahydro-1H-benzo[e]indol-6-yl dimethylcarbamate hydrochloride
B = (−)-cis-3-(-Cyclohexylethyl)-2,3,3a,4,5,9b-hexahydro-1H-benzo[e]indol-6-yl dimethylcarbamate hydrochloride
C = rac-cis-3-(-Cyclohexylethyl)-2,3,3a,4,5,9b-hexahydro-1H-benzo[e]indol-6-yl dimethylcarbamate hydrochloride
D = rac-cis-2,3,3a,4,5,9b-Hexahydro-3-(4-phthalimidobutyl)-1H-benzo[e]indol-6-yl dimethylcarbamate hydrochloride
E = rac-cis-2,3,3a,4,5,9b-Hexahydro-3-(6-phthalimidohexyl)-1H-benzo[e]indol-6-yl dimethylcarbamate hydrochloride
F = rac-cis-2,3,3a,4,5,9b-Hexahydro-3-(2-morpholinoethyl)-1H-benzo[e]indol-6-yl dimethylcarbamate dihydrochloride
G = rac-cis-2,3,3a,4,5,9b-Hexahydro-3-propyl-1H-benzo[e]indol-9-yl dimethylcarbamate hydrochloride
H = 2,3,3aα,4,5,9bα-Hexahydro-1α-methyl-3-propyl-1H-benzo[e]indol-6-yl dimethylcarbamate hydrochloride The IC 50 values for additional compounds of formula I of the invention are:

(+)-3-(2-Cyclohexylethyl)-cis-2,3,3a,4,5,9b-hexahydro-1H-benzo[e]indol-6-yl methylcarbamate: 18;
(+)-3-(2-cyclohexylethyl)-cis-2,3,3a,4,5,9b-hexahydro-1H-benzo[e]indol-6-yl ethylcarbamate: 2460;
(+)-3-(2-cyclohexylethyl)-cis-2,3,3a,4,5,9b-hexahydro-1H-benzo[e]indol-6-yl propylcarbamate: 2.6;
rac-3-(2-cyclohexylethyl)-cis-2,3,3a,4,5,9b-hexahydro-1H-benzo[e]indol-6-yl butylcarbamate: 793;
(+)-3-(2-cyclohexylethyl)-cis-2,3,3a,4,5,9b-hexahydro-1H-benzo[e]indol-6-yl ethylmethylcarbamate: 3.5;
rac-3-cyclohexylmethyl-cis-2,3,3a,4,5,9b-hexahydro-1H-benzo[e]indol-6-yl dimethylcarbamate: 36;
rac-3-(3-cyclohexylpropyl)-cis-2,3,3a,4,5,9b-hexahydro-1H-benzo[e]indol-6-yl dimethylcarbamate: 19;
rac-3-(4-cyclohexylbutyl)-cis-2,3,3a,4,5,9b-hexahydro-1H-benzo[e]indol-6-yl dimethylcarbamate: 35;
rac-3-(2-cyclopentylethyl)-cis-2,3,3a,4,5,9b-hexahydro-1H-benzo[e]indol-6-yl dimethylcarbamate: 30;
rac-3-(3-methylbutyl)-cis-2,3,3a,4,5,9b-hexahydro-1H-benzo[e]indol-6-yl dimethylcarbamate: 67;
rac-3-phenethyl-cis-2,3,3a,4,5,9b-hexahydro-1H-benzo[e]indol-6-yl dimethylcarbamate: 47;
rac-3-propyl-cis-2,3,3a,4,5,9b-hexahydro-1H-benzo[e]indol-6-yl dimethylcarbamate: 40;
rac-3-(3-phenylpropyl)-cis-2,3,3a,4,5,9b-hexahydro-1H-benzo[e]indol-6-yl dimethylcarbamate: 36;
rac-3-(3-morpholin-4-yl-propyl)-cis-2,3,3a,4,5,9b-hexahydro-1H-benzo[e]indol-6-yl dimethylcarbamate: 63;
rac-3-(2-piperidin-1-yl-ethyl)-cis-2,3,3a,4,5,9b-hexahydro-1H-benzo[e]indol-6-yl dimethylcarbamate: 31;
rac-3-[5-(1,3-dioxo-isoindolin-2-yl)-pentyl]-cis-2,3,3a,4,5,9b-hexahydro-1H-benzo[e]indol-6-yl dimethylcarbamate: 2.7;
rac-3-[4-(1-oxo-isoindolin-2-yl)-butyl]-cis-2,3,3a,4,5,9b-hexahydro-1H-benzo[e]indol-6-yl dimethylcarbamate: 8.6;
rac-3-[5-(1-oxo-isoindolin-2-yl)-pentyl]-cis-2,3,3a,4,5,9b-hexahydro-1H-benzo[e]indol-6-yl dimethylcarbamate: 4.5;
rac-3-[6-(1-oxo-isoindolin-2-yl)-hexyl]-cis-2,3,3a,4,5,9b-hexahydro-1H-benzo[e]indol-6-yl dimethylcarbamate: 2.9;
rac-3-(3-benzoyl-propyl)-cis-2,3,3a,4,5,9b-hexahydro-1H-benzo[e]indol-6-yl dimethylcarbamate: 8.3;
rac-3-(4-benzoyl-butyl)-cis-2,3,3a,4,5,9b-hexahydro-1H-benzo[e]indol-6-yl-dimethylcarbamat: 612;
rac-3-[4-(3,4-Dimethoxy-benzoyl)-butyl]-cis-2,3,3a,4,5,9b-hexahydro-1H-benzo[e]indol-6-yl dimethylcarbamate: 1.4;
rac-3-[5-(3,4-dimethoxy-benzoyl)-pentyl]-cis-2,3,3a,4,5,9b-hexahydro-1H-benzo[e]indol-6-yl dimethylcarbamate: 1.2;
rac-3-[4-(4,4-dimethyl-2,6-dioxo-piperidin-1-yl)-butyl]-cis-2,3,3a,4,5,9b-hexahydro-1H-benzo[e]indol-6-yl dimethylcarbamate: 13;
rac-3-[5-(4,4-dimethyl-2,6-dioxo-piperidin-1-yl)-pentyl]-cis-2,3,3a,4,5,9b-hexahydro-1H-benzo[e]indol-6-yl dimethylcarbamate: 11;
rac-3-[6-(4,4-dimethyl-2,6-dioxo-piperidin-1-yl)-hexyl]-cis-2,3,3a,4,5,9b-hexahydro-1H-benzo[e]indol-6-yl dimethylcarbamate: 8;
rac-3-[3-(4-fluoro-benzoyl)-propyl]-cis-2,3,3a,4,5,9b-hexahydro-1H-benzo[e]indol-6-yl dimethylcarbamate: 6.8;
rac-N-[4-(6-dimethylcarbamoyloxy)-cis-2,3,3a,4,5,9b-hexahydro-1H-benzo[e]indol-3-yl)-butyl]-4-methanesulfonylbenzamide: 6.7;
rac-N-[5-(6-dimethylcarbamoyloxy)-cis-2,3,3a,4,5,9b-hexahydro-1H-benzo[e]indol-3-yl)-pentyl]-4-methanesulfonylbenzamide: 5.1;
rac-N-[6-(6-dimethylcarbamoyloxy)-cis-2,3,3a,4,5,9b-hexahydro-1H-benzo[e]indol-3-yl)-hexyl]-4-methanesulfonylbenzamide: 5.6;
rac-N-[4-(6-dimethylcarbamoyloxy)-cis-2,3,3a,4,5,9b-hexahydro-1H-benzo[e]indol-3-yl)-butyl]-benzamide: 16;
rac-N-[5-(6-dimethylcarbamoyloxy)-cis-2,3,3a,4,5,9b-hexahydro-1H-benzo[e]indol-3-yl)-pentyl]-benzamide: 15.2;
rac-N-[6-(6-dimethylcarbamoyloxy)-cis-2,3,3a,4,5,9b-hexahydro-1H-benzo[e]indol-3-yl)-hexyl]-benzamide: 11;
rac-cis-(3-cyclopentylpropyl)-2,3,3a,4,5,9b-hexahydro-1H-benzo[e]indol-6-yl dimethylcarbamate: 14;
rac-cis-3-cyclopentyl-2,3,3a,4,5,9b-hexahydro-1H-benzo[e]indol-6-yl dimethylcarbamate: 95;
rac-3-(4-aminobutyl)-2,3,3a,4,5,9b-hexahydro-1H-cis-benzo[e]indol-6-yl dimethylcarbamate: 267;
rac-3-(5-aminopentyl)-2,3,3a,4,5,9b-hexahydro-1H-cis-benzo[e]indol-6-yl dimethylcarbamate: 111;
rac-3-(6-aminohexyl)-2,3,3a,4,5,9b-hexahydro-1H-cis-benzo[e]indol-6-yl dimethylcarbamate: 8;
rac-3-benzyl-2,3,3a,4,5,9b-hexahydro-1H-cis-benzo[e]indol-6-yl dimethylcarbamate: 49;
rac-3-[5-(1,3-dioxo-octahydro-cis-isoindol-2-yl)pentyl]-2,3,3a,4,5,9b-hexahydro-1H-cis-benzo[e]indol-6-yl dimethylcarbamate: 7.8; and
(+)-trans-3-(2-cyclohexylethyl)-2,3,3a,4,5,9b-hexahydro-1H-benzo[e]indol-6-yl dimethylcarbamate: 22.

Furthermore, the compounds of formula I have affinity for sigma receptors, determined according to Weber et al., Proc. Natl. Acad. Sci. USA 83 (1986), 8784) and in part also for muscarinic receptors, determined according to Watson et al., Pharmacol. Exp. Ther. 237 (1986), 419 and according to Eberlein et al., Trends Pharmacol. Science 10 (1989), 50. From the following binding profile it will be evident that compound A shows on the one hand affinity to sigma receptors and on the other hand preferential affinity for muscarinic receptors of the M2 type:

| Receptor | Radioligand | Percentage inhibition at concentration of | |
|---|---|---|---|
| | | $10^{-7}$ M | $10^{-5}$ M |
| Sigma | [3H]-DTG | 62.1 | 100.7 |
| M1 | [3H]-Pirenzepine | 2.2 | 87.9 |
| M2 | [3H]-AFDX 384 | 31.3 | 94.8 |

Thus, compound A has antagonistic properties to muscarinic receptors, because in micromolar concentrations it antagonizes a contraction of a preparation of guinea pig plexus myentericus induced by muscarinic agonists (according to Kilbinger et al., Eur. J. Pharmacol. 103 (1984) 313).

The compound in accordance with the invention and their pharmaceutically acceptable acid addition salts can be used as medicaments, for example, in the form of pharmaceutical preparations. The pharmaceutical preparations can be administered orally, for example, in the form of tablets, coated tablets, drageés, hard and soft gelatin capsules, solutions, emulsions or suspensions. The administration can, however, also be effected rectally, for example, in the form of suppositories, or parenterally, for example, in the form of injection solutions.

As mentioned earlier, medicaments containing a compound in accordance with the invention or a pharmaceutically acceptable acid addition salt thereof are also an object of the invention, as is a process for the preparation of such medicaments which comprises bringing one or more compounds in accordance with the invention and/or pharmaceutically acceptable acid addition salts thereof and, if desired, one or more other therapeutically active substances into a galenical form together with one or more therapeutically inert excipients.

Lactose, corn starch or derivatives thereof, talc, stearic acid or its salts and the like can be used for example, as excipients for the preparation of tablets, coated tablets, drageés and hard gelatin capsules.

Suitable excipients for soft gelatin capsules are, for example, vegetable oils, waxes, fats, semi-solid and liquid polyols and the like.

Suitable excipients for the preparation of solutions and syrups are, for example, water, polyols, saccharose, invert sugar, glucose and the like.

Suitable excipients for injection solutions are, for example, water, alcohols, polyols, glycerol, vegetable oils and the like.

Suitable excipients for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, coating agents or antioxidants. They can also contain other therapeutically valuable substances.

In accordance with the invention, the compounds of the invention and pharmaceutically acceptable acid addition salts thereof can be used for the treatment or prophylaxis of cognitive disorders and senile dementia, especially Alzheimer's disease and for the improvement of memory capacity. The dosages utilized can vary within wide limits and will, of course, be fitted to the individual requirements in each particular case. In general, in the case of oral administration a daily dosage of about 1 to 200 mg should be appropriate, although the upper limit just given can also be exceeded when this is shown to be indicated.

Finally, the use of the compounds of the invention and of pharmaceutically acceptable acid addition salts thereof for the preparation of medicaments for the treatment or prophylaxis of cognitive disorders and senile dementia, especially Alzheimer's disease, and for the improvement of memory capacity is also an object of the invention.

In the following Examples, further illustrate the invention, all temperatures are given in degrees Celsius.

EXAMPLE 1 a) 439 g (2.49 mol) of 5-methoxy-2-tetralone and 227 ml (3.67 mol) of pyrrolidine were dissolved in 3 l of toluene. After the addition of 16.4 g (0.09 mol) of p-toluenesulfonic acid monohydrate the mixture was boiled for 4 hours, whereby the resulting water was removed continuously using a water separator. Thereupon, the toluene was distilled off in a vacuum. The residue was dissolved in 1 l of tetrahydrofuran, whereupon a solution of 500 g (2.70 mol) of iodoacetamide in 2.5 l of tetrahydrofuran was added dropwise at room temperature. The mixture was boiled at reflux for 30 minutes, then cooled to room temperature and stirred for a further 12 hours. The solid was filtered off and washed with tetrahydrofuran. There were obtained 475 g (89%) of 1,3,4,5-tetrahydro-6-methoxy-2H-benzo[e]indol-2-one as white crystals with m.p. 220°–222°.

b) 313 g (1.45 mol) of 1,3,4,5-tetrahydro-6-methoxy-2H-benzo[e]indol-2-one were suspended in 3 l of methylene chloride. After the addition of 690 ml (4.33 mol) of triethylsilane 500 ml (6.53 mol) of trifluoroacetic acid were slowly added dropwise at 0°, whereupon the mixture was stirred at room temperature for 3 hours, then cooled with an ice-ethanol bath, made alkaline with about 830 ml of 28% sodium hydroxide solution, poured into water and extracted with methylene chloride. The organic phase was washed with saturated sodium chloride solution and dried with sodium sulphate. After distillation of the solvent in a vacuum the residue was suspended in ice-cold ether. The solid was filtered off, rinsed with ether and dried. There were obtained 210 g (67%) of rac-cis-1,3,3a,4,5,9b-hexahydro-6-methoxy-2-benzo[e]indol-2-one as white crystals with m.p. 192°–194°.

c) A suspension of 25 g (0.66 mol) of lithium aluminum hydride in 2 l of tetrahydrofuran was treated portionwise with 71.5 g (0.33 mol) of rac-cis-1,3,3a,4,5,9b-hexahydro-6-methoxy-2H-benzo[e]indol-2-one. The mixture was boiled at reflux overnight, cooled to about −10° and then hydrolyzed by the successive dropwise addition of 25 ml of water, 25 ml of 15 percent sodium hydroxide solution and 75 ml of water. The solid residue was filtered off and rinsed with methylene chloride. The organic phases were concentrated. The residue was dissolved in methylene chloride and the solution was dried with sodium sulphate. After distillation of the solvent in a vacuum and crystallization in a refrigerator there were obtained 64.0 g (96%) of rac-cis-2,3,3a,4,5,9b-hexahydro-6-methoxy-1H-benzo[e]indole as grey crystals.

A small sample was dissolved in ethanol and treated with ethanolic HCl. After concentration and recrystallization from ethanol there was obtained rac-cis-2,3,3a,4,5,9b-hexahydro-6-methoxy-1H-benzo[e]indole hydrochloride with a m.p. of 226°–231°.

d) A suspension of 24.1 g (0.12 mol) of rac-cis-2,3,3a,4,5,9b-hexahydro-6-methoxy-1H-benzo[e]indole, 28.3 g (0.15 mol) of 2-cyclohexylethyl bromide, 26.3 g (0.19 mol) of potassium carbonate and 6.22 g (0.04 mol) of sodium iodide in 550 ml of ethyl methyl ketone was boiled at reflux for 3 days. The solid was filtered off and the solvent was distilled in a vacuum. The residue was dissolved in ethyl acetate, whereupon the solution was washed with water and sodium chloride solution and concentrated. After chromatography over silica gel (ethyl acetate-methylene chloride 1:2) there were obtained 16.1 g (43%) of rac-cis-3-(2-cyclohexylethyl)-2,3,3a,4,5,9b-hexahydro-6-methoxy-1H-benz[e]indole as a beige oil.

MS: m/e (% basis peak): 313 (M+,11), 217 (21), 216 (100), 108 (13), 44 (13).

e) 16.1 g (0.05 mol) of rac-cis-3-(2-cyclohexylethyl)-2,3,3a,4,5,9b-hexahydro-6-methoxy-1H-benz[e]indole were boiled at 120° for 3 hours with 270 ml of 48 percent aqueous hydrobromic acid. After distilling off the hydrobromic acid in a vacuum the residue was dissolved in methylene chloride/water. After extraction with methylene chloride at pH 8 the solvent was distilled off in a vacuum. After chromatography over silica gel (methylene chloridemethanol 10:1) there were obtained 10.3 g (67%) of rac-cis-3-(2-cyclohexylethyl)-2,3,3a,4,5,9b-hexahydro-1H-benzo[e]indol-6-ol as a beige oil.

A small sample was dissolved in ethanol and treated with ethanolic HCl. After concentration and recrystallization from ethanol there was obtained rac-cis-3-(2-cyclohexylethyl)-2,3,3a,4,5,9b-hexahydro-1H-benzo[e]indol-6-ol hydrochloride with m.p. 223°-224°.

f) A suspension of 2.00 g (0.006 mol) of rac-cis-3-(2-cyclohexylethyl)-2,3,3a,4,5,9b-hexahydro-1H-benzo[e]indol-6-ol in 160 ml of toluene was treated with 2 ml (0.014 mol) of triethylamine, 0.88 g (0.007 mol) of 4-dimethylaminopyridine and 0.7 ml (0.007 mol) of dimethylcarbamoyl chloride and then boiled under reflux for 4 hours. After cooling the mixture was poured into a saturated aqueous sodium hydrogen carbonate solution. After extraction with methylene chloride and chromatography over silica gel with ethyl acetate/hexane 1:2 there were obtained 2.40 g of rac-cis-3-(2-cyclohexylethyl)-2,3,3a,4,5,9b-hexahydro-1H-benzo[e]indol-6-yl dimethylcarbamate as an oil.

MS: m/e (% basis peak): 370 (M+,7), 274 (18), 273 (100), 72 (60).

The oil obtained was dissolved in ethanol and treated with ethanolic HCl. After distillation there were obtained 2.34 g (94%) of rac-cis-3-(2-cyclohexylethyl)-2,3,3a,4,5,9b-hexahydro-1H-benzo[e]indol-6-yl dimethylcarbamate hydrochloride as a beige foam.

EXAMPLE 2 a) A solution of 6.98 g (0.023 mol) of rac-cis-3-(2-cyclohexylethyl)-2,3,3a,4,5,9b-hexahydro-1H-benzo[e]indol-6-ol in 70 ml of methylene chloride was mixed with a solution of 5.80 g (0.017 mol) of (−)-2,2'-(1,1'-binaphthyl)phosphoric acid in 70 ml of ethanol and 70 ml of methylene chloride. After distilling off the solvent in a vacuum the residue was recrystallized five times from ethanol and then suspended in aqueous ammonia solution. Extraction with ether gave 2.53 g (36%) of (+)-cis-3-(2-cyclohexylethyl)-2,3,3a,4,5,9b-hexahydro-1H-benzo[e]indol-6-ol as white crystals with m.p. 130°-133°,$[\alpha]_D^{20}=65.9°$(MeOH, c=1%).

A small sample was dissolved in ethanol and treated with ethanolic HCl. After concentration and recrystallization from ethanol there was obtained (+)-cis-3-(2-cyclohexylethyl)-2,3,3a,4,5,9b-hexahydro-1H-benzo[e]indol-6-ol hydrochloride as white crystals with m.p. 199°-200°,$[\alpha]_D^{20}=+35.7°$(MeOH, c=1%).

b) A suspension of 2.53 g (0.008 mol) of (+)-cis-3-(2-cyclohexylethyl)-2,3,3a,4,5,9b-hexahydro-1H-benzo[e]indol-6-ol in 100 ml of toluene was treated with 1.4 ml (0.01 mol) of triethylamine, 1.24 g (0.01 mol) of 4-dimethylaminopyridine and 0.93 ml (0.01 mol) of dimethylcarbamoyl chloride. The mixture was boiled under reflux for 4 hours. After distilling of the solvent in a vacuum the residue was dissolved in methylene chloride. The solution was extracted with water and saturated aqueous sodium chloride solution. The extracts were dried with sodium sulphate and concentrated. Chromatography over silica gel with ethyl acetate/n-hexane/methylene chloride 1:1:1 gave 2.49 g of an oil which was dissolved in ethanol and treated with 2.3 ml of 8.8M ethanolic HCl. After concentration the residue was dissolved in methylene chloride. After filtration the solvent was distilled off in a vacuum. The residue was suspended in ethyl acetate. After filtration and drying at 60° in a vacuum there were obtained 2.37 g (69%) of (+)-cis-3-(2-cyclohexylethyl)-2,3,3a,4,5,9b-hexahydro-1H-benzo[e]indol-6-yl dimethylcarbamate hydrochloride as colorless crystals with m.p. 207°.

EXAMPLE 3 a) A solution of 14.1 g (0.04 mol) of rac-cis-3-(2-cyclohexylethyl)-2,3,3a,4,5,9b-hexahydro-1H-benzo[e]indol-6-ol in 150 ml of methylene chloride was mixed with a solution of 9.81 g (0.028 mol) of (+)-2,2'-(1,1'-binaphthyl)phosphoric acid in 150 ml of ethanol and 150 ml of methylene chloride. After distilling of the solvent in a vacuum the residue was recrystallized five times from ethanol and then suspended in aqueous ammonia solution. Extraction with ether gave 2.09 g (14%) of (−)-cis-3-(2-cyclohexylethyl)-2,3,3a,4,5,9b-hexahydro-1H-benzo[e]indol-6-ol as white crystals with m.p. 130°-133°,$[\alpha]_D^{20}=-63.4°$(MeOH, c=1%).

A small sample was dissolved in ethanol and treated with ethanolic HCl. After concentration of the solution and recrystallization of the residue from ethanol there was obtained (−)-cis-3-(2-cyclohexylethyl)-2,3,3a,4,5,9b-hexahydro-1H-benzo[e]indol-6-ol hydrochloride as white crystals with m.p. 199°-200° C., $[\alpha]_D^{20}=-33.7°$(MeOH, c=1%).

b) A suspension of 1.78 g (0.006 mol) of (−)-cis-3-(2-cyclohexylethyl)-2,3,3a,4,5,9b-hexahydro-1H-benzo[e]indol-6-ol in 100 ml of toluene was treated with 1 ml (0.007 mol) of triethylamine, 0.87 g (0.007 mol) of 4-dimethylaminopyridine and 0.66 ml (0.007 mol) of dimethylcarbamoyl chloride and boiled under reflux for 24 hours. After distilling off the solvent in a vacuum the residue was dissolved in methylene chloride, whereupon the solution was extracted with water and sodium chloride solution. The extracts were dried with sodium sulphate and concentrated. Chromatography over silica gel with methylene chloride/methanol 20:1 gave 1.12 g of an oil which was dissolved in ethanol and treated with ethanolic HCl. After concentration and recrystallization from ethyl acetate there was obtained 0.70 g (29%) of (−)-cis-3-(2-cyclohexylethyl)-2,3,3a,4,5,9b-hexahydro-1H-benzo[e]indol-6-yl dimethylcarabamate hydrochloride as colorless crystals with m.p. 206°.

EXAMPLE 4 a) A solution of 1.00 g (0.005 mol) of rac-cis-2,3,3a,4,5,9b-hexahydro-6-methoxy-1H-benzo[e]indole in 60 ml of ethyl methyl ketone was treated with 0.86 g (0.006 mol) of potassium carbonate, 0.29 g (0.002 mol) of sodium iodide and 1.40 g (0.005 mol) of N-(4-bromobutyl)phthalimide. The mixture was boiled under reflux for 24 hours and, after cooling, treated with water. The mixture was extracted with ethyl acetate, the extracts were dried with sodium sulphate and the solvent was distilled off in a vacuum. Chromatography over silica gel with methylene chloride/methanol 20:1 gave 2.10 g (quant.) of crude rac-cis-N-[4-(1,2,3a,4,5,9b-hexahydro-6-methoxy-3H-benzo[e]indol-3-yl)butyl]phthalimide as pale yellow crystals. A small sample was recrystallized from ethyl acetate/ether and then exhibited a m.p. of 103°–105°.

b) A solution of 2.00 g (0.005 mol) of rac-cis-N-[4-(1,2,3a,4,5,9b-hexahydro-6-methoxy-3H-benzo[e]indol-3-yl)butyl]phthalimide in 100 ml of methylene chloride was treated dropwise with a solution of 2.4 ml (0.025 mol) of boron tribromide in 100 ml of methylene chloride, whereupon the mixture was stirred at room temperature for 1.5 hours. 32 ml (0.065 mol) of 2N sodium hydroxide solution were added dropwise while cooling with an ice bath. The mixture was poured into water, whereupon an aqueous sodium hydrogen carbonate solution was added until a pH of 8 had been reached. The mixture was extracted with methylene chloride, the extracts were dried over sodium sulphate and the solvent was distilled off in a vacuum. Chromatography over silica gel with methylene chloride/methanol 20:1 yielded an oil which was dissolved in ethanol and treated with ethanolic HCl. Distillation of the solvent and recrystallization from methanol gave 0.3 g (14%) of rac-N-[4-(cis-1,2,3a,4,5,9b-hexahydro-6-hydroxy-3H-benzo[e]indol-3-yl)butyl]phthalimide hydrochloride as white crystals with m.p. 258°–260° (dec.).

c) A mixture of 0.12 g (0.28 mol) of rac-N-[4-(cis-1,2,3a, 4,5,9b-hexahydro-6-hydroxy-3H-benzo[e]indol-3-yl)butyl]phthalimide hydrochloride, 0.03 ml (0.34 mmol) of dimethylcarbamoyl chloride, 0.05 ml (0.34 mmol) of triethylamine and 0.042 g (0.34 mmol) of 4-dimethylaminopyridine in 10 ml of toluene was boiled under reflux for 4 hours and then poured into water. The mixture was extracted with toluene, the extracts were dried with sodium sulphate and the solvent was distilled off in a vacuum. The residue was chromatographed over silica gel with methylene chloride/methanol (20:1) and then dissolved in ethanol. The solution was treated with ethanolic HCl and concentrated. The residue was dissolved in methylene chloride, ether was added thereto, the solvent was distilled off and there was obtained 0.11 g (79%) of rac-cis-2,3,3a,4,5,9b-hexahydro-3-(4-phthalimidobutyl)-1H-benzo[e]indol-6-yl dimethylcarbamate hydrochloride as a foam.

MS: m/e (% basis peak): 461 (M+, 8) 457 (2), 274 (19), 273 (100), 216 (4), 200 (3), 160 (10), 130 (2), 72 (57).

EXAMPLE 5 a) A solution of 1.00 g (0.005 mol) of rac-cis-2,3,3a,4,5,9b-hexahydro-6-methoxy-1H-benzo[e]indole in 60 ml of ethyl methyl ketone was treated with 0.85 g (0.006 mol) of potassium carbonate, 0.28 g (0.002 mol) of sodium iodide and 1.60 g (0.005 mol) of N-(6-bromohexyl)phthalimide. The mixture was boiled under reflux for 24 hours, cooled, treated with water and extracted with ethyl acetate. The extracts were dried with sodium sulphate, whereupon the solvent was distilled off in a vacuum. Chromatography of the residue over silica gel with methylene chloride/methanol (20:1) gave 1.90 g of an oil which was dissolved in methylene chloride. After the addition of ethanolic HCl and distillation of the solvent there were obtained 2.00 g (87%) of rac-cis-N-[6-(1,2,3a,4,5,9b-hexahydro-6-methoxy-3H-benzo[e]indol-3-yl)hexyl]phthalimide hydrochloride.

MS: m/e (% basis peak): 432 (M+, 6), 217 (15), 216 (100), 185 (4), 160 (7).

b) A solution of 1.80 g (0.004 mol) of rac-cis-N-[6-(1,2,3a, 4,5,9b-hexahydro-6-methoxy-3H-benzo[e]indol-3-yl)hexyl]phthalimide hydrochloride in 100 ml of methylene chloride was treated dropwise with a solution of 1.8 ml (0.019 mol) of boron tribromide in 10 ml of methylene chloride. The mixture was stirred at room temperature for 1.5 hours, subsequently treated dropwise with 25 ml (0.05 mol) of 2N sodium hydroxide solution while cooling with an ice bath and then poured into water, whereupon aqueous sodium hydrogen carbonate solution was added until a pH of 8 had been reached. The mixture was extracted with chloroform, the extracts were dried over sodium sulphate and the solvent was distilled off in a vacuum. The residue was chromatographed over silica gel with methylene chloride/methanol (20:1). The oil obtained was dissolved in ethanol and treated with ethanolic HCl. Distillation of the solvent and recrystallization from methanol gave 0.93 g (53%) of rac-cis-N-[6-(1,2,3a,4,5,9b-hexa-hydro-6-hydroxy-3H-benzo[e]indol-3-yl)-hexyl]phthalimide hydrochloride as white crystals with m.p. 218°.

c) A mixture of 0.30 g (0.66 mmol) of rac-cis-N-[6-(1,2,3a, 4,5,9b-hexahydro-6-hydroxy-3H-benzo[e]indol-3-yl)-hexyl]phthalimide hydrochloride, 0.06 ml (0.66 mmol) of dimethylcarbamoyl chloride, 0.19 ml (1.32 mmol) of triethylamine and 0.08 g (0.66 mmol) of 4-dimethylaminopyridine in 10 ml of toluene was boiled under reflux for 24 hours and then poured into saturated aqueous sodium hydrogen carbonate solution. The mixture was extracted with methylene chloride, the extracts were dried with sodium sulphate and the solvent was distilled off in a vacuum. The residue was chromatographed over silica gel with methylene chloride/methanol (20:1) and dissolved in methylene chloride. The solution was treated with ethanolic HCl and concentrated. The residue was dissolved in methylene chloride, ether was added thereto and the solvent was distilled off. There was obtained 0.12 g (32%) of rac-cis-2,3,3a,4,5,9b-hexahydro-3-(6-phthalimidohexyl)-1H-benzo[e]indol-6-yl dimethylcarbamate hydrochloride as a foam.

MS: m/e (% basis peak): 489 (M+,7), 396 (2), 274 (19), 273 (100), 201 (2), 160 (8), 72 (64).

EXAMPLE 6 a) 28 g (0.16 mol) of 5-methoxy-2-tetralone and 12.5 g (14.5 ml, 0.175 mol) of pyrrolidine were dissolved in 150 ml of toluene. The mixture was boiled on a water separator for 2 hours, cooled, treated with 31.7 g (0.19 mol) of ethyl bromoacetate and boiled under reflux for 2 hours. The mixture was then concentrated, dissolved in 150 ml of ethanol/water (5:1) and again boiled under reflux for 2 hours. The solvent was distilled off in a vacuum and the residue was dissolved in ethyl acetate. The solution was washed with water and saturated sodium chloride solution, dried with MgSO$_4$, filtered and concentrated. The residue was dissolved in ether, treated with active charcoal and recrystallized. There were obtained 18.4 g of ethyl rac-1,2,3,4-tetrahydro-5-methoxy-2-oxo-1-napthylacetate as white crystals. A further 10.3 g of white crystals could be obtained from the mother liquors by chromatography over silica gel with cyclohexane/ethyl acetate (4:1). Total yield: 28.7 g (68%) of white crystals with m.p. 36°-40°.

b) A solution of 6.30 g (0.024 mol) of ethyl rac-1,2,3,4-tetrahydro-5-methoxy-2-oxo-1-napthylacetate in 100 ml of toluene was treated with 3.1 ml (0.024 mol) of 4-(2-aminoethyl)morpholine, whereupon the mixture was boiled on a water separator for 20 hours. After concentration the residue was hydrogenated with 1 g of Raney-nickel in 100 ml of ethanol at 120° and 180 bar. The product was chromatographed over silica gel with methylene chloride/methanol (9:1). There were obtained 6.80 g (86%) of oily rac-cis-1,3,3a, 4,5,9b-hexahydro-6-methoxy-3-(2-morpholinoethyl)-2H-benzo[e]indol-2-one.

MS: m/e (% basis peak): 330 (M+,3), 299 (1), 160 (3), 149 (4), 113 (23), 100 (100).

c) 1.0 g (27.1 mmol) of lithium aluminum hydride was suspended in 20 ml of tetrahydrofuran under argon. After the dropwise addition of a solution of 6.8 g (0.021 mol) of rac-cis-1,3,3a,4,5,9b-hexahydro-6-methoxy-3-(2-morpholinoethyl)-2H-benzo[e]indol-2-one in 20 ml of tetrahydrofuran the mixture was boiled under reflux for 1 hour and then cautiously treated dropwise firstly with 5 ml of ethyl acetate and then with saturated aqueous $Na_2SO_4$ solution until a complete white precipitate had formed. After filtration and concentration of the filtrate the residue was dissolved in 100 ml of ethanol. The solution was treated dropwise with 7 ml (0.041 mol) of 21 percent ethanolic HCl solution and stirred at room temperature for 4 hours, whereby crystals separated. Recrystallization of these crystals from ethanol gave 6.35 g (79%) of rac-cis-2,3,3a, 4,5,9-hexahydro-6-methoxy-3-(2-morpholinoethyl)-1H-benzo[e]indole hydrochloride as white crystals with m.p. 125°-155° (dec.).

d) 6.28 g (0.016 mol) of rac-cis-2,3,3a,4,5,9b-hexahydro-6-methoxy-3-(2-morpholinoethyl)-1H-benzo[e]indole hydrochloride were dissolved in 0.5 l of 48 percent aqueous HBr, boiled under reflux for 4 hours and then concentrated, whereupon the residue was dissolved in water. The solution was neutralized by adding firstly solid $Na_2SO_3$ and then saturated aqueous $NaHCO_3$ solution. The mixture was extracted three times with $CH_2Cl_2$, the organic phase was washed with saturated aqueous $NaHCO_3$ and NaCl solutions, dried with $Na_2SO_4$, filtered, the filtrate was concentrated and the residue was chromatographed over 0.27 kg of silica gel with methylene chloride/methanol (4:1). The product (4.8 g) was dissolved in 150 ml of ethanol. 6 ml (0.035 mol) of 21 percent ethanolic HCl solution were added dropwise thereto and the mixture was stirred at room temperature for 4 hours, whereby crystals separated. Recrystallization from ethanol gave 4.97 g (82%) of rac-cis-2,3,3a,4,5,9b-hexahydro-3-(2-morpholinoethyl)-1H-benzo[e]indol-6-ol dihydrochloride as white crystals with m.p. 230°-275° (dec.).

e) 1.00 g (0.003 mol) of rac-cis-2,3,3a,4,5,9b-hexahydro-3-(2-morpholinoethyl)-1H-benzo[e]indol-6-ol dihydrochloride dissolved in 50 ml of water was neutralized with 5.6 ml of 1N sodium hydroxide solution (5.6 mmol, 2.1 eq.). The mixture was extracted with ether, the organic phase was washed with saturated aqueous $NaHCO_3$ and NaCl solutions, dried with $Na_2SO_4$, filtered and the filtrate was concentrated. The oily residue was dissolved in 50 ml of toluene. 0.30 g (0.41 ml, 0.003 mol) of triethylamine, 3.25 mg (266 μmol, 0.1 eq.) of 4-dimethylaminopyridine and 0.27 ml (0.003 mol) of dimethylcarbamoyl chloride were added thereto in succession. The mixture was boiled under reflux for 2 hours, poured into water and extracted with $CH_2Cl_2$. The organic phase was washed with saturated aqueous $NaHCO_3$ and NaCl solutions, dried with $Na_2SO_4$, filtered, the filtrate was concentrated and the residue was chromatographed on 220 g of silica gel with methylene chloride/methanol (9:1). The resulting oil (0.8 g) was dissolved in 10 ml of ethanol. 0.92 ml (0.0045 mol) of 4.89N ethanolic HCl solution was added dropwise thereto and precipitation was effected with ethyl acetate. The crystals were filtered off, dissolved in hot ethanol and treated with active charcoal. After filtration, concentration and recrystallization from ethanol/ethyl acetate there was obtained 0.57 g (48%) of rac-cis-2,3,3a,4,5,9b-hexahydro-3-(2-morpholinoethyl)-1H-benzo[e]indol-6-yl dimethylcarbamate dihydrochloride as white crystals with m.p. 170°-220° (dec.).

EXAMPLE 7 a) A solution of 15.0 g (0.057 mol) of ethyl 1,2,3,4-tetrahydro-5-methoxy-2-oxo-1-naphthyl acetate in 250 ml of toluene was treated with 9.45 ml (0.114 mol) of propylamine, whereupon the mixture was boiled on a water separator for 17 hours. After concentration and threefold recrystallization there were obtained 4.4 g of white crystals. Chromatography of the mother liquors over silica gel with ether/hexane (2:1) and recrystallization gave an additional 2.45 g of material. Total yield: 6.85 g, m.p. 81°-83°.

6.80 g (0.026 mol) of the product obtained were hydrogenated with 1.5 g of raney-nickel in 400 ml of ethanol at 120° and 140 bar for 15 hours. The product was chromatographed over silica gel with hexane/ether (1:1). There were obtained 5.20 g of oily rac-cis-1,3,3a,4,5,9b-hexahydro-6-methoxy-3-propyl-2H-benzo[e]indol-2-one.

b) 2.73 g (0.027 mol) of diisopropylamine were dissolved in 150 ml of dry tetrahydrofuran under argon. 16.7 ml of 1.61M butyllithium in hexane (0.027 mol) were added dropwise at −78°, whereupon the mixture was stirred at 0° for 15 minutes, again cooled to −78° and treated dropwise with a solution of 6.40 g (0.025 mol) of rac-cis-1,3,3a,4,5,9b-hexahydro-6-methoxy-3-propyl-2H-benzo[e]indol-2-one in 100 ml of tetrahydrofuran. The temperature of the yellow solution was allowed to rise to 0°, the solution was again cooled to −78° and then a solution of 3.83 g (0.027 mol) of methyl iodide in 30 ml of tetrahydrofuran was added dropwise thereto. The temperature of the mixture was allowed to rise to 0° and the mixture was stirred at this temperature for 3 hours. Then, 10 ml of a saturated aqueous $NH_4Cl$ solution were cautiously added dropwise. The mixture was extracted with ethyl acetate, whereupon the organic phase was washed with water, dried with $MgSO_4$, filtered and concentrated. The residue was chromatographed over 150 g of silica gel with hexane/ether (1:1) and there were obtained 4.8 g (71%) of rac-1,3,3aα,4,5,-9bα-hexahydro-6-methoxy-1α-methyl-3-propyl-2H-benzo[e]indol-2-one as a pale yellow oil.

c) 1.33 g (0.0035 mol) of lithium aluminum hydride were added to a solution of 4.8 g (0.018 mol) of rac-1,3,3aα,4,5,9bα-hexahydro-6-methoxy-1α-methyl-3- propyl-2H-benzo[e]indol-2-one in 100 ml of tetrahydrofuran under argon. The mixture was boiled under reflux for 2 hours and then treated cautiously at 5°–10° firstly with 10 ml of a saturated aqueous NH₄Cl solution and then with 50 ml of water and finally extracted with ethyl acetate. The organic phase was dried with MgSO₄, filtered and concentrated, whereupon the residue was chromatographed over 130 g of silica gel with methylene chloride/methanol (49:1). There were obtained 4.35 g (95%) of rac-2,3,3aα,4,5,9bα-hexahydro-6-methoxy-1α-methyl-3-propyl-1H-benzo[e]indole as a pale yellow oil.

d) 4.35 g (0.017 mol) of rac-2,3,3aα,4,5,9bα-hexahydro-6-methoxy-1α-methyl-3-propyl-1H-benzo[e]indole were boiled under reflux in 150 ml of 48 percent aqueous HBr for 1.5 hours, whereupon the mixture was concentrated. The residue was neutralized with 50 ml of water, 5 ml of 2N aqueous NaOH solution and 50 ml of saturated NaHCO₃ solution and extracted three times with 100 ml of CH₂Cl₂ each time. The combined organic phases were dried over MgSO₄, filtered and concentrated. The brown residue (4.8 g) was dissolved in 10 ml of ethanol and 30 ml of ethyl acetate, whereupon 3.7 ml (21.5 mmol) of 5.8N ethanolic HCl solution were added dropwise. The mixture was stirred at room temperature for 4 hours, whereby crystals separated. The crystals were filtered off under suction washed with ethyl acetate and ether and dried in a vacuum (2.7 g). A further 1.1 g could be obtained from the mother liquor by crystallization. The total amount was then dissolved in methanol, whereupon the solution was treated with active charcoal, filtered and concentrated. The residue was recrystallized twice from methanol/ethyl acetate and there were obtained 2.65 g (56%) of rac-2,3,3aα,4,5,9bα-hexahydro-1α-methyl-3-propyl-1H-benzo[e]indol-6-ol hydrochloride with m.p. 201°–203°.

e) 1 g (0.0035 mol) of rac-2,3,3aα,4,5,9bα-hexahydro-1α-methyl-3-propyl-1H-benzo[e]indol-6-ol hydrochloride dissolved in 50 ml of water was neutralized with 3.7 ml of 1N sodium hydroxide solution, whereupon the mixture was extracted with ether. The organic phase was washed with saturated aqueous NaHCO₃ and NaCl solutions, dried over Na₂SO₄, filtered and concentrated. The oily residue was diluted with 50 ml of toluene, whereupon 0.38 g (0.52 ml, 0.004 mol) of triethylamine and 43.3 mg (355 μmol, 0.1 eq.) of 4-dimethylaminopyridine were added in succession and then 0.34ml (0.004 mol) of dimethylcarbamoyl chloride was added dropwise. The mixture was boiled under reflux for 2 hours, then cooled and poured into water, whereupon the mixture was extracted with CH₂Cl₂. The organic phase was washed with saturated aqueous NaHCO₃ and NaCl solutions, dried with Na₂SO₄, filtered and concentrated. The residue was chromatographed over 220 g of silica gel with methylene chloride/methanol (9:1). The resulting oil (1.11 g) was dissolved in 10 ml of ethanol, whereupon there was added dropwise 0.75 ml (3.7 mmol) of 4.89N ethanolic HCl solution and then ethyl acetate until the solution was turbid. Subsequently, the mixture was stirred at room temperature for 4 hours and at 0° for 1 hour. The separated crystals were filtered off under suction, washed with ethyl acetate and dried at 150°/0.02 Torr for 3 hours. There were obtained 1.14 g (91%) of rac-2,3,3aα,4,5,9bα-hexahydro-1α-methyl-3-propyl-1H-benzo[e]indol-6-ol dimethylcarbamate hydrochloride as white crystals with m.p. 240°–247°.

EXAMPLE 8 a) 8.81 g (0.05 mol) of 8-methoxy-2-tetralone and 3.91 g (4.55 ml, 0.055 mol) of pyrrolidine were dissolved in 50 ml of toluene. The mixture was boiled on a water separator for 2 hours, cooled, treated with 10.2 g (0.06 mol) of ethyl bromoacetate, then boiled under reflux for a further 2 hours and finally concentrated. The residue was dissolved in 60 ml of ethanol/water (5:1), whereupon the solution was boiled under reflux for 2 hours. Then, the solvent was distilled off in a vacuum. A solution of the residue in ethyl acetate was washed with water and saturated sodium chloride solution, dried with MgSO₄, filtered and concentrated. The residue was chromatographed over silica gel with cyclohexane/ethyl acetate (4:1). There were obtained 12.0 g (92%) of oily ethyl rac-1,2,3,4-tetrahydro-8-methoxy-2-oxo-1-naphthyl acetate.

b) A solution of 11.76 g (0.045 mol) of ethyl rac-1,2,3,4-tetrahydro-8-methoxy-2-oxo-1-naphthyl acetate in 100 ml of toluene was treated with 7.4 ml (0.09 mol) of propylamine. The mixture was boiled on a water separator for 20 hours and then concentrated. The residue was hydrogenated with 4 g of Raney-nickel in 200 ml of ethanol at 120° and 140 bar. The product was chromatographed over silica gel with cyclohexane/ethyl acetate (1:1). There were obtained 10.1 g (87%) of oily rac-cis-1,3,3a,4,5,9b-hexahydro-9-methoxy-3-propyl-2H-benzo[e]indol-2-one. A sample was recrystallized from hexane and gave white crystals with m.p. 74°–76°.

c) 1.44 g (0.038 mol) of lithium aluminum hydride were suspended in 20 ml of tetrahydrofuran under argon, whereupon a solution of 9.83 g (0.038 mol) of rac-cis-1,3,3a,4,5,9b-hexahydro-9-methoxy-3-propyl-2H-benzo[e]indol-2-one in 50 ml of tetrahydrofuran was added dropwise. The mixture was boiled under reflux for 1 hour and then, after cooling, cautiously treated dropwise firstly with 10 ml of ethyl acetate and then with saturated aqueous Na₂SO₄ solution until a complete white precipitate had formed. After filtration and concentration of the filtrate there was obtained rac-cis-2,3,3a,4,5,9b-hexahydro-9-methoxy-3-propyl-1H-benzo[e]indole as an oil which was used in the next step without further purification.

d) 8.58 g (0.035 mol) of rac-cis-2,3,3a,4,5,9b-hexahydro-9-methoxy-3-propyl-1H-benzo[e]indole were boiled under reflux for 4 hours in 0.5 l of 48 percent aqueous HBr. The mixture was poured into an ice-cold aqueous solution of 200 g (5 mol) of NaOH. Solid NaHCO₃ was added thereto and the mixture was extracted three times with CH₂Cl₂. The combined organic phases were washed with saturated aqueous NaHCO₃ and NaCl solutions, dried with Na₂SO₄, filtered and concentrated. The residue was chromatographed over silica gel with ethyl acetate. The product was crystallized in hexane. There were obtained 6.4 g (80%) of rac-cis-2,3,3a,4,5,9b-hexahydro-3-propyl-1H-benzo[e]indol-9-ol as white crystals with m.p. 130°–132°.

6.2 g (0.027 mol) thereof were dissolved in 220 ml of ethyl acetate/ethanol (10:1), whereupon 6 ml (0.035 mol) of a 5.87M ethanolic HCl solution were added dropwise and the mixture was stirred at 0° for 4 hours. There were obtained 6.18 g (82%) of rac-cis-2,3,3a,4,5,9b-hexahydro-3-propyl-1H-benzo[e]indol-9-ol hydrochloride as white crystals with m.p. 207°–213°.

e) A mixture of 1.10 g (0.004 mol) of rac-cis-2,3,3a,4,5,9b-hexahydro-3-propyl-1H-benzo[e]indol-9- ol hydrochloride, 0.61 g (0.005 mol) of dimethylcarbamoyl chloride, 1.4 ml (0.01 mol) of triethylamine and 0.61 g (0.005 mol) of 4-dimethylaminopyridine in 40 ml of toluene was boiled under reflux for 4 hours and then poured into a saturated aqueous sodium hydrogen carbonate solution, whereupon the mixture was extracted with methylene chloride. The extract was dried with sodium sulphate, filtered and evaporated in a vacuum. The residue was purified by chromatography over silica gel with methylene chloride/methanol (99:1) and over aluminum oxide with methylene chloride and dissolved in ethanol. After the addition of ethanolic HCl the solvent was distilled off. There were obtained 1.20 g (86%) of rac-cis-2,3,3a,4,5,9b-hexahydro-1H-benzo[e]indol-9-yl dimethylcarbamate hydrochloride as a foam.

MS: m/e (% basis peak): 302 (M+,9) 273 (51), 72 (100), 42 (18).

EXAMPLE 9 a) 4.0 g (0.01525 mol) of ethyl 1,2,3,4-tetrahydro-5-methoxy-2-oxo-1-naphthylacetate were dissolved in 80 ml of toluene, 1.98 ml (0.01525 mol) of aminomethylcyclohexane were added thereto and the mixture was boiled for 23 hours on a water separator. After concentration the residue was hydrogenated with 1.5 g of Raney-nickel in 150 ml of ethanol at 120° and 140 bar for 10 hours. After chromatography over silica gel with cyclohexane/ethyl acetate 3:1 the product was dissolved in hot isopropyl ether and crystallized at room temperature. There were obtained 3.82 g (80%) of rac-cis-3-cyclohexylmethyl-1,3,3a,4,5,9b-hexahydro-6-methoxy-2H-benzo[e]indol-2-one as white crystals with m.p. 136°-137°.

b) 0.92 g (0.02412 mol) of lithium aluminum hydride was suspended in 40 ml of THF under argon. A solution of 3.78 g (0.01206 mol) of rac-cis-3-cyclohexylmethyl-1,3,3a,4,5,9b-hexahydro-6-methoxy-2H-benzo[e]indol-2-one in 40 ml of THF was added dropwise thereto and the mixture was boiled under reflux for 2 hours. Then, 0.9 ml of water, 0.9 ml of 4N sodium hydroxide solution and 2.7 ml of water were cautiously added dropwise thereto in succession, whereupon the mixture was boiled at reflux until a complete white precipitate had resulted. After the addition of dry $Na_2SO_4$, filtration and concentration there was obtained an oil which was chromatographed over silica gel with cyclohexane/ethyl acetate 4:1. There were obtained 3.53 g (98%) of oily rac-cis-3-cyclohexylmethyl-2,3,3a,4,5,9b-hexahydro-6-methoxy-1H-benzo[e]indole.

MS: m/e (% basis peak)=299 ($C_{20}H_{29}NO^+$, 5), 216 (100), 185 (8), 150 (10), 144 (7), 115 (14).

c) 3.46 g (0.01155 mol) of rac-cis-3-cyclohexylmethyl-2,3,3a,4,5,9b-hexahydro-6-methoxy-1H-benzo[e]indole were dissolved in 0.13 l of 48% aqueous HBr and boiled under reflux for 5 hours. The mixture was poured into an ice-cold aqueous solution of 46.3 g (1.16 mol) of NaOH, whereupon, after the addition of solid $NaHCO_3$, the mixture was extracted three times with $CH_2Cl_2$. The organic phase was washed with saturated aqueous $NaHCO_3$ and NaCl solutions, dried with $Na_2SO_4$ and then filtered, whereupon the filtrate was concentrated. By chromatography of the residue over silica gel with cyclohexane/ethyl acetate 4:1 there were obtained 3.38 g (100%) of oily rac-cis-3-cyclohexylmethyl-2,3,3a,4,5,9b-hexahydro-1H-benzo[e]indol-6-ol.

0.49 g (0.00171 mol) of the oil obtained was dissolved in 15 ml of methanol. 0.35 ml (0.00173 mol) of 4.93N ethanolic HCl solution was added dropwise thereto and the mixture was concentrated. The hydrochloride remaining as the residue was crystallized from ethanol/ether. Yield: 0.47 g (85%) of white crystals with m.p. 195°-197°.

d) 2.78 g (0.00973 mol) of rac-cis-3-cyclohexylmethyl-2,3,3a,4,5,9b-hexahydro-1H-benzo[e]indol-6-ol were dissolved in 50 ml of toluene. 1.97 g (2.71 ml, 0.01948 mol) of triethylamine and 120 mg (980 mmol, 0.1 eq.) of 4-dimethylaminopyridine were added thereto in succession and then 1.79 ml (0.01948 mol) of dimethyl chloroformamide were added dropwise thereto. The mixture was boiled under reflux for 2 hours, then cooled, poured into water and extracted with toluene. The organic phase was washed with water, dried with $Na_2SO_4$, filtered and concentrated. By chromatography of the residue over 220 g of silica gel with cyclohexane/ethyl acetate 1:1 there were obtained 3.3 g (95%) of oily rac-cis-3-cyclohexylmethyl-2,3,3a,4,5,9b-hexahydro-1H-benzo[e]indol-6-yl dimethylcarbamate.

3.24 g (0.00909 mol) of the oil obtained were dissolved in 30 ml of ethanol. 1.83 ml (9.12 mmol) of 4.93N ethanolic HCl solution were added dropwise thereto and the mixture was concentrated. The hydrochloride remaining as the residue was crystallized from acetonitrile/ether. Yield: 2.99 g (82%) of white crystals of m.p. 192°-194°.

EXAMPLE 10 a) 4.0 g (0.01525 mol) of ethyl 1,2,3,4-tetrahydro-5-methoxy-2-oxo-1-naphthylacetate were dissolved in 80 ml of toluene, 2.29 ml (0.016 mol) of 3-phenylpropylamine were added thereto and the mixture was boiled for 20 hours on a water separator. After concentration the residue was hydrogenated with 1.5 g of Raney-nickel in 150 ml of ethanol at 120° and 140 bar for 10 hours. The product was chromatographed over silica gel with cyclohexane/ethyl acetate 2:1. There were obtained 3.13 g (61%) of oily rac-cis-3-(3-cyclohexyl-propyl)-1,3,3a,4,5,9b-hexahydro-6-methoxy-2H-benzo[e]indol-2-one.

MS: m/e (% basis peak)=341 ($C_{22}H_{31}NO_2^+$, 92), 258 (52), 245 (26), 230 (100), 173 (72), 158 (52), 144 (23), 128 (19), 115 (31).

b) 0.38 g (0.010 mol) of lithium aluminum hydride was suspended in 40 ml of THF under argon. A solution of 3.26 g (0.00955 mol) of rac-cis-3-(3-cyclohexylpropyl)-1,3,3a,4,5,9b-hexahydro-6-methoxy-2H-benzo[e]indol-2-one in 30 ml of THF was added dropwise thereto and the mixture was boiled under reflux for 2 hours. Then, 10 ml of ethyl acetate and a saturated aqueous $Na_2SO_4$ solution were cautiously added dropwise thereto in succession until a complete white precipitate had resulted. After filtration and concentration there was obtained an oil which was chromatographed over silica gel with cyclohexane/ethyl acetate 1:1. There were obtained 2.64 g (84%) of oily rac-cis-3-(3-cyclohexylpropyl)-2,3,3a,4,5,9b-hexahydro-6-methoxy-1H-benzo[e]indole.

MS: m/e (% basis peak)=327 ($C_{22}H_{33}NO^+$, 10), 216 (100), 185 (5,5), 159 (7), 144 (4,5).

c) 2.62 g (0.008 mol) of rac-cis-3-(3-cyclohexylpropyl)-2,3,3a,4,5,9b-hexahydro-6-methoxy-1H-benzo[e]indole were dissolved in 0.09 of 48% aqueous HBr and boiled under the reflux for 5 hours. The mixture was poured into an ice-cold aqueous solution of 32 g (0.8 mol) of NaOH, whereupon, after the addition of solid $NaHCO_3$, the mixture was extracted three times with $CH_2Cl_2$. The organic phase was washed with saturated aqueous NaHCO$_3$ and NaCl solutions, dried with Na$_2$SO$_4$, filtered and concentrated. By chromatography of the residue over silica gel with cyclohexane/ethyl acetate 1:1 there was obtained 0.92 g (37%) of oily rac-cis-3-(3-cyclohexyl-propyl)-2,3,3a,4,5,9b-hexahydro-1H-benzo[e]indol-6-ol.

0.201 g of the oil obtained was dissolved in 1 ml of ethanol. 0.135 ml (0.673 mol) of 5N ethanolic HCl solution and then ethyl acetate were added dropwise thereto until the solution became turbid. Then, it was stirred at room temperature for 1 hour and at 0° for 1 hour. The separated crystals were filtered off under suction, washed with ethyl acetate and dried at 150°/0.02 Torr for 2 hours. There was obtained 0.20 g (89%) of the hydro-chloride as white crystals with m.p. 216°–221°.

d) 0.67 g (0.00214 mol) of rac-cis-3-(3-cyclohexyl-propyl)-2,3,3a,4,5,9b-hexahydro-1H-benzo[e]indol-6-ol was dissolved in 20 ml of toluene. 0.277 g (0.31 ml, 0.00224 mol) of triethylamine and 26 mg (214 mmol, 0.1 eq.) of 4-dimethylaminopyridine were added thereto in succession and then 0.21 ml (0.00224 mol) of dimethyl chloroformamide was added dropwise thereto. The mixture was boiled under reflux for 5 hours, then cooled, poured into water and extracted with CH$_2$Cl$_2$. The organic phase was washed with saturated aqueous NaHCO$_3$ and NaCl solutions, dried with Na$_2$SO$_4$, filtered and concentrated. By chromatography of the residue over 220 g of silica gel with CH$_2$Cl$_2$/MeOH 9:1 there was obtained 0.787 g of an oil which was dissolved in about 5 ml of ethanol. 0.42 ml (2.1 mmol) of 5N ethanolic HCl solution and then ethyl acetate were added dropwise thereto until the solution became turbid, whereupon it was stirred at room temperature for 16 hours. The separated crystals were filtered off under suction, recrystallized and dried at 100°/0.02 Torr for 3 hours. There was obtained 0.55 g (61%) of rac-cis-3-(3-cyclohexyl-propyl)-2,3,3a,4,5,9b-hexahydro-1H-benzo[e]indol-6-yl dimethylcarbamate hydrochloride as white crystals with m.p. 158°–163°.

EXAMPLE 11 a) 5.0 g (0.0191 mol) of ethyl 1,2,3,4-tetrahydro-5-methoxy-2-oxo-1-naphthylacetate were dissolved in 100 ml of toluene, 3.0 ml (0.0191 mol) of 4-phenyl-butylamine were added thereto and the mixture was boiled for 16 hours on a water separator. After concentration the residue was hydrogenated with 2.0 g of Raney-nickel in 200 ml of ethanol at 120° and 140 bar for 10 hours. The product was chromatographed over silica gel with n-hexane/ethyl acetate 3:1. There were obtained 5.60 g (82.5%) of oily rac-cis-3-(4-cyclohexyl-butyl)-1,3,3a,4,5,9b-hexahydro-6-methoxy-2H-benzo[e]indol-2-one.

MS: m/e (% basis peak)=355 (C$_{23}$H$_{33}$NO$_2^+$, 60), 272 (16), 258 (11), 244 (12), 230 (60), 173 (40), 159 (30), 115 (25), 83 (18), 55 (100), 41 (83).

b) 0.79 g (0.0208 mol) of lithium aluminum hydride was suspended in 20 ml of THF under argon. A solution of 5.60 g (0.01575 mol) of rac-cis-3-(4-cyclohexyl-butyl)-1,3,3a,4,5,9b-hexahydro-6-methoxy-2H-benzo[e]indol-2-one in 60 ml of THF was added dropwise thereto and the mixture was boiled under reflux for ½ hour. 10 ml of THF/water 4:1, 4 ml of 15% aqueous NaOH solution and 2 ml of water were cautiously added dropwise thereto in succession, whereupon the mixture was boiled under reflux for 15 minutes until a complete white precipitate had resulted. After filtration, concentration and chromatography of the residue over silica gel with n-hexane/ethyl acetate 1:1 there were obtained 5.0 g (93%) of oily rac-cis-3-(4-cyclohexyl-butyl)-2,3,3a,4,5,9b-hexahydro-6-methoxy-1H-benzo[e]indole.

c) 5.0 g (0.0146 mol) of rac-cis-3-(4-cyclohexyl-butyl)-2,3,3a,4,5,9b-hexahydro-6-methoxy-1H-benzo[e]indole were dissolved in 0.171 of 48% aqueous HBr and boiled under reflux for 5 hours. The mixture was poured onto ~200 g of ice and treated with 200 ml of 28% aqueous NaOH solution. The mixture was extracted three times with ethyl acetate, whereupon the organic phase was washed with saturated sodium chloride solution, dried with MgSO$_4$, filtered and concentrated. By chromatography of the residue over silica gel with n-hexane/ethyl acetate 1:1 there were obtained 4.3 g (90%) of oily rac-cis-3-(4-cyclohexyl-butyl)-2,3,3a,4,5,9b-hexahydro-1H-benzo[e]indol-6-ol.

1.0 g (0.00305 mol) of the oil obtained was dissolved in 50 ml of ethanol. 0.74 ml (3.36 mmol) of 4.56N ethanolic HCl solution was added dropwise thereto, the mixture was cooled to 0° and treated with 100 ml of ether. The separated crystals were filtered off under suction, washed with cold ether and dried at 150°/0.05 Torr for 1 hour. There was obtained 0.98 g (88%) of the hydrochloride as white crystals with m.p. 228°–230°.

d) 3.30 g (0.01008 mol) of rac-cis-3-(4-cyclohexyl-butyl)-2,3,3a,4,5,9b-hexahydro-1H-benzo[e]indol-6-ol were dissolved in 70 ml of 1,2-dichloroethane. 3.05 g (4.2 ml, 0.0301 mol) of triethylamine and 330 mg (2.70 mmol, 0.27 eq.) of 4-dimethylaminopyridine were added thereto in succession and then 2.8 ml (0.03024 mol) of dimethyl chloroformamide were added dropwise thereto. The mixture was boiled under reflux for 1 hour, then cooled, poured into water and extracted with CH$_2$Cl$_2$. The organic phase was washed with saturated aqueous sodium chloride solution, dried with MgSO$_4$, filtered and concentrated, whereupon the residue was chromatographed over silica gel with n-hexane/ethyl acetate 1:1. The oil obtained (3.2 g) was dissolved in 100 ml of ether. 1.85 ml (8.83 mmol) of 4.78N ethanolic HCl solution were added dropwise thereto and the oily suspension was sonicated for 15 minutes in an ultrasonics bath. Then, it was stirred at room temperature for 1 hour and the separated crystals were filtered off under suction. After recrystallization from 120 ml of hot ethyl acetate and drying at 100°/0.02 Torr for 3 hours there were obtained 2.90 g (83%) of rac-cis-3-(4-cyclohexyl-butyl)-2,3,3a,4,5,9b-hexahydro-1H-benzo[e]indol-6-yl dimethylcarbamate hydrochloride as white crystals with m.p. 145°–147°.

EXAMPLE 12 a) 5.0 g (0.0246 mol) of rac-cis-2,3,3a,4,5,9b-hexahydro-6-methoxy-1H-benzo[e]indole were dissolved in 100 ml of CH$_2$Cl$_2$, 4.1 ml (0.0295 mol) of triethylamine were added thereto and a solution of 4.3 ml (0.0295 mol) of 3-cyclopentylacetyl chloride in 40 ml of CH$_2$Cl$_2$ was added dropwise thereto at 15° under argon. The mixture was stirred at room temperature for ½ hour, then poured into water and extracted with CH$_2$Cl$_2$. The organic phase was washed with saturated aqueous NaHCO$_3$ and NaCl solutions, dried with MgSO$_4$, filtered and concentrated. By chromatography of the residue over silica gel with n-hexane/ethyl acetate 3:1 there were obtained 6.50 g (84%) of pale yellow oily rac-cis-3-(cyclopentylacetyl)-2,3,3a,4,5,9b-hexahydro-6-methoxy-1H-benzo[e]indole.

MS: m/e (% basis peak)=313 ($C_{20}H_{27}NO_2^+$, 28) 245 (26), 186 (34), 173 (16), 160 (17), 115 (13), 87 (100).

b) 1.02 g (0.0269 mol) of lithium aluminum hydride were suspended in 30 ml of THF under argon. A solution of 6.5 g (0.0207 mol) of rac-cis-3-(cyclopentylacetyl)-2,3,3a,4,5,9b-hexahydro-6-methoxy-1H-benzo[e]indole in 80 ml of THF was added dropwise thereto and the mixture was boiled under reflux for 1 hour. 10 ml of THF/water 9:1, 2 ml of a 4N aqueous NaOH solution and 2 ml of water were cautiously added dropwise thereto in succession, whereupon the mixture was boiled under reflux for 15 minutes until a complete white precipitate had resulted. After filtration and concentration there was obtained an oil which was dissolved in 100 ml of ethanol. 5.1 ml (0.0245 mol) of 4.78N ethanolic HCl solution were added dropwise thereto, the mixture was stirred for 15 minutes and concentrated. The residue crystallized from 100 ml of hot ethyl acetate. There were obtained 5.87 g (86%) of rac-cis-3-(2-cyclopentyl-ethyl)-6-methoxy-2,3,3a,4,5,9b-hexahydro-1H-benzo[e]indole hydrochloride as white crystals with m.p. 185°–187° (dec.).

c) 5.80 g (0.0173 mol) of rac-cis-3-(2-cyclopentylethyl)-6-methoxy-2,3,3a,4,5,9b-hexahydro-1H-benzo[e]indole hydrochloride were dissolved in 0.18 l of 48% aqueous HBr and boiled under reflux for 5 hours. The mixture was poured on to ~200 g of ice and treated with 200 ml of 28% aqueous NaOH solution. The mixture was extracted three times with ethyl acetate, whereupon the organic phase was washed with saturated sodium chloride solution, dried with $MgSO_4$, filtered and concentrated. By chromatography of the residue over silica gel with ethyl acetate there were obtained 4.20 g (85%) of oily rac-cis-3-(2-cyclopentylethyl)-2,3,3a,4,5,9b-hexahydro-1H-benzo[e]indol-6-ol.

1.2 g (0.0042 mol) of the yellowish oil were dissolved in 25 ml of ethanol. 1.05 ml (0.00505 mol) of 4.8N ethanolic HCl solution were added dropwise thereto and the white suspension was treated with 50 ml of ether. The mixture was stirred at 0° for 1 hour. The separated crystals were filtered off under suction, washed with ether and dried at 150°/0.02 Torr for 2 hours. There were obtained 1.20 g (89%) of the hydrochloride as white crystals with m.p. 205°–207° (dec.).

d) 3.0 g (0.0105 mol) of rac-cis-3-(2-cyclopentylethyl)-2,3,3a,4,5,9b-hexahydro-1H-benzo[e]indol-6-ol were dissolved in 100 ml of 1,2-dichloroethane. 3.2 g (4.4 ml, 0.0315 mol) of triethylamine and 300 mg (0.00446 mol, 0.25 eq.) of 4-dimethylaminopyridine were added thereto in succession and then 3.1 ml (0.0315 mol) of dimethyl chloroformamide were added dropwise thereto. The mixture was boiled under reflux for 1.5 hours, then cooled, poured into water and extracted with $CH_2Cl_2$. The organic phased was washed with saturated aqueous sodium chloride solution, dried with $MgSO_4$, filtered and concentrated. By chromatography of the residue over silica gel with ethyl acetate/n-hexane 1:1 there were obtained 3.2 g of an oil which was dissolved in 60 ml of ethyl acetate. 2.1 ml (0.010 mol) of 4.78N ethanolic HCl solution were added dropwise thereto, whereupon crystals separated upon cooling to 0°. The crystals were filtered off under suction and dried at 130°/0.02 Torr for 1.5 hours. There were obtained 2.93 g (83%) of rac-cis-3-(2-cyclopentyl-ethyl)-2,3,3a,4,5,9b-hexahydro-1H-benzo[e]indol-6-yl dimethylcarbamate hydrochloride as white crystals with m.p. 178°–180° (dec.).

EXAMPLE 13 a) 4.06 g (0.020 mol) of rac-cis-2,3,3a,4,5,9b-hexahydro-6-methoxy-1H-benzo[e]indole were dissolved in 80 ml of $CH_2Cl_2$, 3.35 ml (0.024 mol) of triethylamine were added thereto and a solution of 3.7 ml (0.024 mol) of 3-cyclopentylpropionyl chloride in 40 ml of $CH_2Cl_2$ was added dropwise thereto at 20° under argon. The mixture was stirred at room temperature for 1 hour, then poured into water and extracted with $CH_2Cl_2$. The organic phase was washed with saturated aqueous $NaHCO_3$ and NaCl solutions, dried with $MgSO_4$, filtered and concentrated. By chromatography of the residue over silica gel with n-hexane/ethyl acetate 1:1 there were obtained 4.75 g (72.5%) of rac-cis-3-(3-cyclopentyl-propionyl)-2,3,3a,4,5,9b-hexahydro-6-methoxy-1H-benzo[e]indole as a pale yellow, oily material.

MS: m/e (% basis peak)=327 ($C_{21}H_{29}NO_2^+$, 32), 258 (20), 245 (43), 186 (42), 159 (23), 115 (21), 100 (41), 87 (100).

b) 0.71 g (0.0187 mol) of lithium aluminum hydride was suspended in 20 ml of THF under argon. A solution of 4.7 g (0.01435 mol) of rac-cis-3-(3-cyclopentyl-propionyl)-2,3,3a,4,5,9b-hexahydro-6-methoxy-1H-benzo[e]indole in 50 ml of THF was added dropwise thereto and the mixture was boiled under reflux for ½ hour. 10 ml of THF/water 4:1, 4 ml of a 15% aqueous NaOH solution and 2 ml of water were cautiously added dropwise thereto in succession, whereupon the mixture was boiled under reflux for 10 minutes until a complete white precipitate had resulted. After filtration and concentration there was obtained an oil which was chromatographed over silica gel with n-hexane/ethyl acetate 1:1. There were obtained 4.40 g (98%) of rac-cis-3-(3-cyclopentylpropyl)-2,3,3a,4,5,9b-hexahydro-6-methoxy-1H-benzo[e]indole as a yellowish, oily material.

MS: m/e (% basis peak)=313 ($C_{21}H_{31}NO^+$, 6,8), 216 (100), 185 (7), 159 (6), 144 (3), 128 (3), 115 (4), 101 (5).

c) 4.40 g (0.014 mol) of rac-cis-3-(3-cyclopentyl-propyl)-2,3,3a,4,5,9b-hexahydro-6-methoxy-1H-benzo[e]indole were dissolved in 0.16 l of 48% aqueous HBr and boiled under reflux for 17 hours. The mixture was poured on to ~200 g of ice and treated with 180 ml of 28% aqueous NaOH solution. The mixture was extracted three times with $CH_2Cl_2$, whereupon the organic phase was washed with water, dried with $MgSO_4$, filtered and concentrated. By chromatography of the residue over silica gel with n-hexane/ethyl acetate 1:1 there were obtained 3.1 g (74%) of rac-cis-3-(3-cyclopentyl-propyl)-2,3,3a,4,5,9b-hexahydro-1H-benzo[e]indol-6-ol as an oily material.

3.0 g (0.010 mol) of the yellowish oil were dissolved in 40 ml of ethanol. 2.4 ml (11.0 mmol) of 4.56N ethanolic HCl solution were added dropwise thereto, the white suspension was treated with 100 ml of ether and stirred at 0° for 1 hour. The separated crystals were filtered off under suction, washed with ether and dried at 150°/0.05 Torr for 1 hour. There were obtained 2.95 g (88%) of the hydrochloride as white crystals with m.p. 206°–209° (dec.).

d) 2.0 g (0.00668 mol) of rac-cis-3-(3-cyclopentyl-propyl)-2,3,3a,4,5,9b-hexahydro-1H-benzo[e]indol-6-ol were dissolved in 40 ml of 1,2-dichloroethane. 2.03 g (2.8 ml, 0.020 mol) of triethylamine and 200 mg (1.64 mmol, 0.25 eq.) of 4-dimethylaminopyridine were added thereto in succession and then 1.8 ml (0.020 mol)

of dimethyl chloroformamide were added dropwise thereto. The mixture was boiled under reflux for 1.5 hours, then cooled, poured into water and extracted with CH$_2$Cl$_2$. The organic phase was washed with saturated aqueous sodium chloride solution, dried with MgSO$_4$, filtered and concentrated. By chromatography of the residue over silica gel with n-hexane/ethyl acetate 1:1 there were obtained 1.9 g of an oil which was dissolved in 80 ml of ether. 1.2 ml (5.64 mmol) of 4.78N ethanolic HCl solution were added dropwise thereto and the oily suspension was sonicated for 20 minutes in an ultrasonics bath. The separated crystals were filtered off under suction and recrystallized from 100 ml of hot ethyl acetate. After drying at 100°/0.010 Torr for 2 hours there were obtained 1.90 g (91%) of rac-cis-3-(3-cyclopentyl-propyl)-2,3,3a,4,5,9b-hexahydro-1H-benzo[e]indol-6-yl dimethylcarbamate hydrochloride as white crystals with m.p. 127°–130° (dec.).

EXAMPLE 14 a) 4.6 g (0.01755 mol) of ethyl 1,2,3,4-tetrahydro-5-methoxy-2-oxo-1-naphthylacetate were dissolved in 80 ml of toluene, 2.04 ml (0.01755 mol) of 3-methyl-butylamine were added thereto and the mixture was boiled for 24 hours on a water separator. After concentration the residue was hydro-genated with 1.8 g of Raney-nickel in 200 ml of ethanol at 120° and 140 bar for 10 hours. The material obtained was chromatographed over silica gel with cyclohexane/ethyl acetate 3:1. The product was dissolved in hot isopropyl ether and crystallized at room temperature. There were obtained 2.84 g (56%) of rac-cis-1,3,3a,4,5,9b-hexahydro-6-methoxy-3-(3-methyl-butyl)-2H-benzo[e]indol-2-one as white crystals with m.p. 81°–82° and 0.79 g (16%) of oily material from the mother liquors.

b) 0.98 g (0.02593 mol) of lithium aluminum hydride was suspended in 50 ml of THF under argon. A solution of 3.61 g (0.01297 mol) of rac-cis-1,3,3a,4,5,9b-hexahydro-6-methoxy-3-(3-methyl-butyl)-2H-benzo[e]indol-2-one in 50 ml of THF was added dropwise thereto and the mixture was boiled under reflux for 2 hours. 1.0 ml of water, 1.0 ml of a 4N aqueous NaOH solution and 3.0 ml of water were cautiously added dropwise thereto in succession, whereupon the mixture was boiled at reflux until a complete white precipitate had resulted. After the addition of dry Na$_2$SO$_4$, filtration and concentration there was obtained an oil which was chromatographed over silica gel with cyclohexane/ethyl acetate 1:1. There were obtained 3.23 g (94%) of oily rac-cis-2,3,3a,4,5,9b-hexahydro-6-methoxy-3-(3-methyl-butyl)-1H-benzo[e]indole.

MS: m/e (% basis peak)=273 (C$_{18}$H$_{27}$NO$^+$, 10), 216 (100), 185 (9), 159 (8), 144 (3), 128 (3), 101 (6).

c) 3.19 g (0.01167 mol) of rac-cis-2,3,3a,4,5,9b-hexahydro-6-methoxy-3-(3-methyl-butyl)-1H-benzo[e]indole were dissolved in 0.13 l of 48% aqueous HBr and boiled under reflux for 5 hours. The mixture was poured into an ice-cold aqueous solution of 46.3 g (1.16 mol) of NaOH. Solid NaHCO$_3$ was added thereto and the mixture was extracted three times with CH$_2$Cl$_2$. The organic phase was washed with saturated aqueous NaHCO$_3$ and NaCl solutions, dried with Na$_2$SO$_4$, filtered and concentrated. The product obtained by chromatography of the residue over silica gel with cyclohexane/ethyl acetate 2:1 was dissolved in hot n-hexane and crystallized at room temperature. There were obtained 2.52 g (75%) of rac-cis-2,3,3a,4,5,9b-hexahydro-3-(3-methyl-butyl)-1H-benzo[e]indol-6-ol as white crystals with m.p. 70°–72° and 0.59 g (16%) of oily material from the mother liquors.

0.40 g (0.00154 mol) of the crystals obtained were dissolved in 40 ml of ethanol. 0.32 ml (0.00158 mol) of 4.93N ethanolic HCl solution was added dropwise thereto and the mixture was concentrated. The hydrochloride was crystallized from hot ethanol. Yield: 0.37 g (81%), as white crystals with m.p. 215°–217°.

d) 2.71 g (0.01045 mol) of rac-cis-2,3,3a,4,5,9b-hexahydro-3-(3-methyl-butyl)-1H-benzo[e]indol-6-ol were dissolved in 60 ml of toluene. 2.1 g (2.90 ml, 0.0208 mol) of triethylamine and 128 mg (1045 mmol, 0.1 eq.) of 4-dimethylaminopyridine were added thereto in succession and then 1.92 ml (0.02088 mol) of dimethyl chloroformamide were added dropwise thereto. The mixture was boiled under reflux for 2 hours, then cooled, poured into water and extracted with toluene. The organic phase was washed with water, dried with Na$_2$SO$_4$, filtered and concentrated. By chromatography of the residue over silica gel with ethyl acetate there were obtained 2.91 g (84%) of oily rac-cis-2,3,3a, 4,5,9b-hexahydro-3-(3-methylbutyl)-1H-benzo[e]indol-6-yl dimethylcarbamate.

2.60 g (0.00786 mol) of the oil obtained were dissolved in 30 ml of ethanol. 1.60 ml (7.89 mmol) of 4.93N ethanolic HCl solution were added dropwise thereto and the mixture was concentrated. The hydrochloride was crystallized from acetonitrile/ether. Yield: 2.62 g (91%), white crystals with m.p. 206°–209°.

EXAMPLE 15 a) 4.0 g (0.01525 mol) of ethyl 1,2,3,4-tetrahydro-5-methoxy-2-oxo-1-naphthylacetate were dissolved in 80 ml of toluene, 2.02 ml (0.016 mol) of 2-phenylethylamine were added thereto and the mixture was boiled for 20 hours on a water separator. After concentration the residue was hydrogenated with 1.5 g of Raney-nickel in 150 ml of ethanol at 70° and 80 bar for 10 hours. The product was chromatographed over silica gel with cyclohexane/ethyl acetate 1:1. The product was crystallized in hexane/ethyl acetate. There were obtained 3.13 g (64%) of rac-cis-1,3,3a,4,5,9b-hexahydro-6-methoxy-3-phenethyl-2H-benzo[e]indol-2-one as white crystals with m.p. 89°–90°.

b) 0.3557 g (0.00936 mol) of lithium aluminum hydride was suspended in 40 ml of THF under argon. A solution of 3.01 g (0.00936 mol) of rac-cis-1,3,3a,4,5,9b-hexahydro-6-methoxy-3-phenethyl-2H-benzo[e]indol-2-one in 40 ml of THF was added dropwise thereto and the mixture was boiled under reflux for 2 hours. 10 ml of ethyl acetate and a saturated aqueous Na$_2$SO$_4$ solution were cautiously added dropwise thereto in succession until a complete white precipitate had resulted. After filtration and concentration there were obtained 2.9 g (100%) of oily rac-cis-2,3,3a,4,5,9b-hexahydro-6-methoxy-3-phenethyl-1H-benzo[e]indole.

c) 2.88 g (0.00936 mol) of rac-cis-2,3,3a,4,5,9b-hexahydro-6-methoxy-3-phenethyl-1H-benzo[e]indole were dissolved in 0.106 l of 48% aqueous HBr and boiled under reflux for 5 hours. The mixture was poured into an ice-cold aqueous solution of 37.4 g (0.936 mol) of NaOH. Then, solid NaHO$_3$ was added thereto and the mixture was extracted three times with CH$_2$Cl$_2$. The organic phase was washed with saturated aqueous NaHCO$_3$ and NaCl solutions, dried with Na$_2$SO$_4$, filtered and concentrated. By chromatography of the residue over silica gel with cyclo-hexane/ethyl acetate 1:1 there were obtained 2.69 g (98%) of oily rac-cis- 2,3,3a,4,5,9b-hexahydro-3-phenethyl-1H-benzo[e]indol-6-ol.

A portion of the oil obtained was dissolved in 1 ml of ethanol and 10 ml of ethyl acetate. 5N ethanolic HCl solution was added dropwise thereto and the mixture was stirred at room temperature for 1 hour and at 0° for 1 hour. The separated crystals were filtered off under suction and washed with ethyl acetate. After recrystallization the crystals were dried at 150°/0.02 Torr for 2 hours. The hydrochloride was obtained as white crystals with m.p. 270°–271°.

d) 2.69 g (0.00917 mol) of rac-cis-2,3,3a,4,5,9b-hexahydro-3-phenethyl-1H-benzo[e]indol-6-ol were dissolved in 90 ml of toluene. 0.974 g (1.34 ml, 0.00963 mol) of triethylamine and 112 mg (917 mmol, 0.1 eq.) of 4-dimethylaminopyridine were added thereto in succession and then 0.88 ml (0.00963 mol) of dimethyl chloroformamide were added dropwise thereto. The mixture was boiled under reflux for 5 hours, then cooled, poured into water and extracted with $CH_2Cl_2$. The organic phase was washed with saturated aqueous $NaHCO_3$ and NaCl solutions, dried with $Na_2SO_4$, filtered and concentrated. By chromatography of the residue over silica gel with dichloromethane/isopropyl alcohol and crystallization of the product in hexane/ethyl acetate there were obtained 3.08 g (92%) of rac-cis-2,3,3a,4,5,9b-hexahydro-3-phenethyl-1H-benzo[e]indol-6-yl dimethylcarbamate as yellowish crystals with m.p. 98°–102°.

2.59 g (0.00711 mol) of these crystals were dissolved in 10 ml of ethanol and 40 ml of ethyl acetate. 1.64 ml (0.00746 mol) of 4.56N ethanolic HCl solution were added dropwise thereto. The mixture was then stirred at room temperature for 1 hour and at 0° for 1 hour. The separated crystals were filtered off under suction, recrystallized and dried at 120°/0.02 Torr for 3 hours. There were obtained 2.32 g (81%) of the hydrochloride as white crystals with m.p. 222°–226°.

EXAMPLE 16 a) 2.35 g (0.0116 mol) of rac-cis-2,3,3a,4,5,9b-hexahydro-6-methoxy-1H-benzo[e]indole were dissolved in 40 ml of $CH_2Cl_2$, 2.80 ml (0.0201 mol) of triethylamine were added thereto and a solution of 1.1 ml (0.0127 mol) of propionyl chloride in 10 ml of $CH_2Cl_2$ was added dropwise thereto at 25° under argon. The mixture was stirred at room temperature for 1 hour, then poured into water and extracted with $CH_2Cl_2$. The organic phase was dried with $MgSO_4$, filtered and concentrated. By chromatography of the residue over silica gel with ether/ethyl acetate 1:1 there were obtained 3.0 g (99.7%) of rac-cis-2,3,3a,4,5,9b-hexahydro-6-methoxy-3-propionyl-1H-benzo[e]indole as a pale yellow, oily material which crystallized overnight; m.p. 81°.

b) 0.90 g (0.0232 mol) of lithium aluminum hydride was suspended in 40 ml of THF under argon. A solution of 3.0 g (0.0116 mol) of rac-cis-2,3,3a,4,5,9b-hexahydro-6-methoxy-3-propionyl-1H-benzo[e]indole in 50 ml of THF was added dropwise thereto and the mixture was boiled under reflux for 1 hour. 25 ml of a saturated aqueous $NH_4Cl$ solution was cautiously added dropwise thereto, the mixture was filtered and the filtrate was extracted with ethyl acetate. The organic phase was washed with water, dried with $MgSO_4$, filtered and concentrated. By chromatography of the residue over silica gel with $CH_2Cl_2$/MeOH 49:1 there were obtained 2.65 g (93%) of rac-cis-2,3,3a,4,5,9b-hexahydro-6-methoxy-3-propyl-1H-benzo[e]indole as a colorless, oily material.

c) 2.65 g (0.0108 mol) of rac-cis-2,3,3a,4,5,9b-hexahydro-6-methoxy-3-propyl-1H-benzo[e]indole were dissolved in 0.151 of 48% aqueous HBr and boiled under reflux for 1 hour. The mixture was concentrated and the residue was taken up in $CH_2Cl_2$ and extracted with a mixture of saturated $NaHCO_3$ solution (100 ml) and a 2N NaOH solution (20 ml). The extracts were dried with $MgSO_4$, filtered and concentrated. The pale rose oil (2.5 g) was dissolved in 40 ml of methanol. 2.05 ml (11.89 mmol) of 5.8N ethanolic HCl solution were added dropwise thereto and the mixture was stirred at room temperature for 1 hour and at 0° for 1 hour. The separated crystals were filtered off under suction and washed with ethyl acetate. After working-up the mother liquors there were obtained a total of 2.4 g (83%) of rac-cis-2,3,3a,4,5,9b-hexahydro-3-propyl-1H-benzo[e]indol-6-ol hydrochloride as white crystals with m.p. 242°–244°.

d) 0.68 g (0.00293 mol) of rac-cis-2,3,3a,4,5,9b-hexahydro-3-propyl-1H-benzo[e]indol-6-ol hydrochloride was dissolved in 40 ml of toluene. 0.31 g (0.43 ml, 0.00308 mol) of triethylamine and 40 mg (0.3 mmol, 0.1 eq.) of 4-dimethylamino-pyridine were added thereto in succession and then 0.28 ml (0.00308 mol) of dimethyl chloroformamide was added dropwise thereto. The mixture was boiled under reflux for 2 hours, then cooled, poured into water and extracted with toluene. The organic phase was washed with water, dried with $Na_2SO_4$, filtered and concentrated. By chromatography of the residue over silica gel with ethyl acetate/ethanol 9:1 there was obtained 0.72 g (0.00238 mol, 81%) of an oil which was taken up in 30 ml of ethanol. 0.48 ml (2.37 mmol) of 4.93N ethanolic HCl solution was added dropwise thereto and the mixture was concentrated. The residue was recrystallized in ethanol/ether and the rac-cis-2,3,3a,4,5,9b-hexahydro-3-propyl-1H-benzo[e]indol-6-yl dimethylcarbamate hydrochloride was dried at 120°/0.02 Torr for 1 hour. Yield: 0.69 g (85%), white crystals with m.p. 168°–170°.

EXAMPLE 17 a) 4.0 g (0.01525 mol) of ethyl 1,2,3,4-tetrahydro-5-methoxy-2-oxo-1-naphthylacetate were dissolved in 80 ml of toluene, 2.29 ml (0.016 mol) of 3-phenylpropylamine were added thereto and the mixture was boiled for 20 hours on a water separator. After concentration the residue was hydrogenated with 1.5 g of Raney-nickel in 150 ml of ethanol at 70° and 80 bar for 10 hours. The product was chromatographed over silica gel with cyclohexane/ethyl acetate 1:1. There were obtained 4.02 g (76%) of oily rac-cis-1,3,3a,4,5,9b-hexahydro-6-methoxy-3-(3-phenyl-propyl)-2H-benzo[e]indol-2-one.

MS: m/e (% basis peak)=335 ($C_{22}H_{25}NO_2^+$, 52), 231 (100), 230 (49), 183 (31), 159 (32), 158 (42), 144 (16), 115 (25), 91 (55).

b) 0.457 g (0.01204 mol) of lithium aluminum hydride was suspended in 40 ml of THF under argon. A solution of 4.04 g (0.01204 mol) of rac-cis-1,3,3a,4,5,9b-hexahydro-6-methoxy-3-(3-phenyl-propyl)-2H-benzo[e]indol-2-one in 40 ml of THF was added dropwise thereto and the mixture was boiled under reflux for 2 hours. 10 ml of ethyl acetate and a saturated aqueous $Na_2SO_4$ solution were cautiously added dropwise thereto in succession until a complete white precipitate had resulted. After filtration and concentration there was obtained an oil which was chromatographed over silica gel with cyclohexane/ethyl acetate 3:1. There were obtained 3.46 g (89%) of oily rac-cis-2,3,3a,4,5,9b-hexahydro-6-methoxy-3-(3-phenyl-propyl)-1H-benzo[e]indole.

MS: m/e (% basis peak)=321 ($C_{22}H_{27}NO^+$, 10), 216 (100), 185 (7), 159 (7), 144 (3), 115 (5.5), 91 (16).

c) 3.45 g (0.0107 mol) of rac-cis-2,3,3a,4,5,9b-hexahydro-6-methoxy-3-(3-phenyl-propyl)-1H-benzo[e]indole were dissolved in 0.121 l of 48% aqueous HBr and boiled under reflux for 5 hours. The mixture was poured into an ice-cold aqueous solution of 42.8 g (1.07 mol) of NaOH. After the addition of solid $NaHCO_3$ the mixture was extracted three times with $CH_2Cl_2$. The organic phase was washed with saturated aqueous $NaHCO_3$ and NaCl solutions, dried with $Na_2SO_4$, filtered and concentrated. By chromatography over silica gel with cyclohexane/ethyl acetate 1:1 and crystallization in hexane/ethyl acetate there were obtained 2.53 g (77%) of rac-cis-2,3,3a,4,5,9b-hexahydro-3-(3-phenyl-propyl)-1H-benzo[e]indol-6-ol as whitish crystals with m.p. 98°–100°. The mother liquor was concentrated and the residue was chromatographed over silica gel with cyclohexane/ethyl acetate 1:1. There was obtained an additional 0.62 g of oily material (2.12 mmol, 19%); total yield: 96%.

The oil obtained (0.62 g, 2.12 mmol) was dissolved in 1 ml of ethanol and 10 ml of ethyl acetate. 0.42 ml (2.12 mmol) of 5N ethanolic HCl solution was added dropwise thereto and the mixture was stirred at room temperature for 1 hour and at 0° for 1 hour. The separated crystals were filtered off under suction and washed with ethyl acetate. After recrystallization the crystals were dried at 150°/0.02 Torr for 2 hours. There was obtained 0.38 g (55%) of the hydrochloride as white crystals with m.p. 180°–183°.

d) 2.5 g (0.00813 mol) of rac-cis-2,3,3a,4,5,9b-hexahydro-3-(3-phenyl-propyl)-1H-benzo[e]indol-6-ol were dissolved in 50 ml of 1,2-dichloroethane. 2.46 g (3.4 ml, 0.0244 mol) of triethylamine and 250 mg (2.05 mmol, 0.25 eq.) of 4-dimethylaminopyridine were added thereto in succession and then 2.2 ml (0.0244 mol) of dimethyl chloroformamide were added dropwise thereto. The mixture was boiled under reflux for 1 hour, then cooled, poured into water and extracted with $CH_2Cl_2$. The organic phase was washed with saturated aqueous $NaHCO_3$ and NaCl solutions, dried with $Na_2SO_4$, filtered and concentrated, whereupon the residue was chromatographed over silica gel with ethyl acetate.

The oil obtained (3.0 g) was taken up in 60 ml of ethyl acetate. 1.90 ml (8.66 mmol) of 4.56N ethanolic HCl solution were added dropwise thereto. Then, the mixture was stirred at room temperature for 2 hours and at 0° for 1 hour. The separated crystals were filtered off under suction, washed with ether and dried at 120°/0.02 Torr for 1 hour. There were obtained 2.80 g (85%) of rac-cis-2,3,3a,4,5,9b-hexahydro-3-(3-phenyl-propyl)-1H-benzo[e]indol-6-yl dimethylcarbamate hydrochloride as white crystals with m.p. 173°–176°.

EXAMPLE 18 a) 4.0 g (0.01525 mol) of ethyl 1,2,3,4-tetrahydro-5-methoxy-2-oxo-1-naphthylacetate were dissolved in 80 ml of toluene, 2.22 ml (0.01525 mol) of N-(3-aminopropyl)-morpholine were added thereto and the mixture was boiled for 43 hours on a water separator. After concentration the residue was hydrogenated with 1.5 g of Raney-nickel in 150 ml of ethanol at 120° and 140 bar for 10 hours. The product was chromatographed over silica gel with ethyl acetate/methanol 5:1, dissolved in hot isopropyl ether and crystallized at room temperature. There were obtained 3.58 g (68%) of rac-cis-1,3,3a,4,5,9b-hexahydro-6-methoxy-3-(3-morpholin-4-yl-propyl)-2H-benzo[e]indol-2-one as white crystals with m.p. 65°–67° and 0.93 g (18%) of oily material from the mother liquors.

b) 0.99 g (0.02595 mol) of lithium aluminum hydride was suspended in 50 ml of THF under argon. A solution of 4.47 g (0.01298 mol) of rac-cis-1,3,3a,4,5,9b-hexahydro-6-methoxy-3-(3-morpholin-4-yl-propyl)-2H-benzo[e]indol-2-one in 50 ml of THF was added dropwise thereto and the mixture was boiled under reflux for 2 hours. 1.0 ml of water, 1.0 ml of a 4N aqueous NaOH solution and 3.0 ml of water were cautiously added dropwise thereto in succession, whereupon the mixture was boiled at reflux until a complete white precipitate had resulted. After the addition of dry $Na_2SO_4$, filtration and concentration there was obtained an oil which was chromatographed over silica gel with ethyl acetate/methanol 1:1. There were obtained 3.79 g (88%) of oily rac-cis-2,3,3a,4,5,9b-hexahydro-6-methoxy-3-(3-morpholin-4-yl-propyl)-1H-benzo[e]indole.

MS: m/e (% basis peak)=330 ($C_{20}H_{30}N_2O_2^+$, 18), 243 (33), 228 (46), 216 (95), 202 (51), 160 (19), 159 (19), 127 (52), 112 (35), 100 (100).

c) 3.75 g (0.01135 mol) of rac-cis-2,3,3a,4,5,9b-hexahydro-6-methoxy-3-(3-morpholin-4-yl-propyl)-1H-benzo[e]indole were dissolved in 0.13 l of 48% aqueous HBr and boiled under reflux for 5 hours. The mixture was poured into an ice-cold aqueous solution of 46.3 g (1.16 mol) of NaOH. After the addition of solid $NaHCO_3$ the mixture was extracted three times with $CH_2Cl_2$. The organic phase was washed with saturated aqueous $NaHCO_3$ and NaCl solutions, dried with $Na_2SO_4$, filtered and concentrated. By chromatography over silica gel with methanol there were obtained 3.20 g (89%) of oily rac-cis-2,3,3a,4,5,9b-hexahydro-3-(3-morpholin-4-yl-propyl)-1H-benzo[e]indol-6-ol.

0.39 g (0.00123 mol) of the oil obtained were dissolved in 50 ml of ethanol. 0.50 ml (0.002475 mol) of 4.93N ethanolic HCl solution was added dropwise thereto and the mixture was concentrated. The dihydrochloride was crystallized from ethanol/ether. Yield: 0.37 g (77%), white crystals with m.p. 219°–221°.

d) 3.37 g (0.01065 mol) of rac-cis-2,3,3a,4,5,9b-hexahydro-3-(3-morpholin-4-yl-propyl)-1H-benzo[e]indol-6-ol were dissolved in 60 ml of toluene. 2.155 g (2.97 ml, 0.0214 mol) of triethyl-amine and 130 mg (1065 mmol, 0.1 eq.) of 4-dimethylaminopyridine were added thereto in succession and then 1.96 ml (0.0213 mol) of dimethyl chloroformamide were added dropwise thereto. The mixture was boiled under reflux for 2 hours, then cooled, poured into water and extracted with toluene. The organic phase was washed with water, dried with $Na_2SO_4$, filtered and concentrated. By chromatography of the residue over silica gel with methanol there were obtained 3.66 g (89%) of oily rac-cis-2,3,3a,4,5,9-hexahydro-3-(3-morphin-4-yl-propyl)-1H-benzo[e]indol-6-yl dimethylcarbamate.

3.61 g (0.01017 mol) of the oil obtained were dissolved in 40 ml of ethanol. 4.17 ml (20.56 mmol) of 4.93N ethanolic HCl solution were added dropwise thereto and the mixture was concentrated. The dihydrochloride was crystallized from ethanol/ether. Yield: 3.90 g (91%), white crystals with m.p. 233°–235°.

EXAMPLE 19 a) 4.0 g (0.01525 mol) of ethyl 1,2,3,4-tetrahydro-5-methoxy-2-oxo-1-naphthylacetate were dissolved in 250 ml of toluene, 4.05 ml (0.0305 mol) of 2-piperidinoethylamine and 0.13 g of p-toluenesulphonic acid monohydrate were added thereto and the mixture was boiled for 4 hours on a water separator. After concentration the residue was hydrogenated with 1.3 g of Raney-nickel in 500 ml of ethanol at 120° and 140 bar for 10 hours. The product was chromatographed over silica gel with $CH_2Cl_2$/MeOH 49:1. There were obtained 4.45 g (89%) of oily rac-cis-1,3,3a,4,59b-hexahydro-6-methoxy-3-(2-piperidinoethyl)-2H-benzo[e]indol-2-one.

b) 1.0 g (0.0268 mol) of lithium aluminum hydride was suspended in 50 ml of THF under argon. A solution of 4.4 g (0.0134 mol) of rac-cis-1,3,3a,4,59b-hexahydro-6-methoxy-3-(2-piperidinoethyl)-2H-benzo[e]indol-2-one in 100 ml of THF was added dropwise thereto and the mixture was boiled under reflux for 1 hour. 25 ml of a saturated aqueous $NH_4Cl$ solution was cautiously added dropwise thereto, the mixture was filtered and the filtrate was extracted with ethyl acetate. The organic phase was washed with water, dried with $MgSO_4$, filtered and concentrated. There were obtained 3.8 g (90%) of rac-cis-2,3,3a,4,5,9b-hexahydro-6-methoxy-3-(2-piperidinoethyl)-1H-benzo[e]indole as a colorless oil.

c) 3.8 g (0.0121 mol) of rac-cis-2,3,3a,4,5,9b-hexahydro-6-methoxy-3-(2-piperidinoethyl)-1H-benzo[e]indole were dissolved in 0.351 of 48% aqueous HBr and boiled under reflux for 5 hours. The mixture was concentrated and the residue was taken up in $CH_2Cl_2$ and extracted with a mixture of 100 ml of saturated $NaHCO_3$ solution and 20 ml of 2N NaOH solution. The extracts were dried with $MgSO_4$, filtered and concentrated. The foam (3.8 g) remaining as the residue was dissolved in 50 ml of ethanol. The mixture was filtered, 4.8 ml (27.84 mmol) of 5.8N ethanolic HCl solution were added dropwise thereto and the mixture was stirred at room temperature for 1 hour and at 0° for 1 hour. The separated crystals were filtered off under suction and washed with ethyl acetate. There were obtained 4.3 g (95%) of rac-cis-2,3,3a,4,5,9b-hexahydro-3-(2-piperidinoethyl)-1H-benzo[e]indol-6-ol dihydrochloride as white crystals with m.p. 265°-267°.

d) 1.0 g (0.00268 mol) of rac-cis-2,3,3a,4,5,9b-hexahydro-3-(2-piperidinoethyl)-1H-benzo[e]indol-6-ol dihydrochloride was dissolved in a dilute aqueous NaOH solution and extracted with ethyl acetate. The organic phase was washed with water, dried over $Na_2SO_4$, filtered and concentrated. The residue was dissolved in 40 ml of toluene, whereupon 0.28 g (0.39 ml, 0.0279 mol) of triethylamine and 35 mg (0.28 mmol, 0.1 eq.) of 4-dimethylaminopyridine were added in succession and then 0.26 ml (0.0279 mol) of dimethyl chloroformamide was added dropwise. The mixture was boiled under reflux for 2 hours, then cooled, poured into water and extracted with toluene. The organic phase was washed with water, dried with $Na_2SO_4$, filtered and concentrated. By chromatography of the residue over silica gel with ethyl acetate/ethanol 1:1 there was obtained 0.82 g (82%) of oily rac-cis-2,3,3a,4,5,9b-hexahydro-3-(2-piperidinoethyl)-1H-benzo[e]indol-6-yl dimethylcarbamate.

0.76 g (0.00205 mol) of the oil obtained was dissolved in 30 ml of ethanol. 0.83 ml (4.09 mmol) of 4.93N ethanolic HCl solution was added dropwise thereto, the mixture was concentrated and the residue was recrystallized from ethanol/ether. The crystals were filtered off under suction, washed with ether and dried at 120°/0.02 Torr for 1 hour. There was obtained 0.84 g (92%) of the dihydrochloride as white crystals with m.p. 183°-185°.

EXAMPLE 20 a) 10.67 g (52.5 mmol) of rac-cis-2,3,3a,4,5,9b-hexahydro-6-methoxy-1H-benzo[e]indole were treated with 250 ml of toluene, 14.5 g (63 mmol) of N-(4-bromobutyl)-3,3-dimethylglutarimide and 6.9 g (9.5 ml; 68.2 mmol) of triethylamine and stirred in an oil bath overnight at an oil bath temperature of 115°. After cooling the separated precipitate was filtered off under suction and washed with toluene, whereupon the filtrate was evaporated. The resulting brown oil (20.7 g) was filtered over a 20-fold amount of silica gel with ethyl acetate. The resulting base (12.6 g of brownish oil) was converted into the hydrochloride in the usual manner and there were obtained 11.9 g (23%) of rac-cis-1-[4-(6-methoxy-2,3,3a,4,5,9b-hexahydro-1H-benzo[e]indol-3-yl)-butyl]-4,4-dimethyl-piperidine-2,6-dione hydrochloride in the form of yellow crystals of m.p. 115°-116°.

b) 8.8 g (22.1 mmol) of rac-cis-1-[4-(6-methoxy-2,3,3a,4,5,9b-hexahydro-1H-benzo[e]indol-3-yl)-butyl]-4,4-dimethyl-piperidine-2,6-dione hydrochloride were mixed well with 100 g of pyridine hydrochloride and stirred under an argon atmosphere in an oil bath for 4 hours at an oil bath temperature of 180°. After cooling the mixture was treated with ice-water, whereupon the brown solution was made alkaline with ammonium hydroxide solution and then extracted with methylene chloride. The organic phase was washed with water, dried over magnesium sulphate and evaporated. The brown oily product obtained (9.8 g) was chromatographed on a 30-fold amount of silica gel. The uniform eluates obtained in a thinlayer chromatogram using methylene chloride/ethyl acetate 1:1 were pooled and evaporated. The oil obtained crystallized after treatment with hexane. There were obtained 5.5 g (65%) of rac-cis-1-[4-(6-hydroxy-2,3,3a,4,5,9b-hexahydro-1H-benzo[e]indol-3-yl)-butyl]-4,4-dimethyl-piperidine-2,6-dione in the form of yellowish crystals of m.p. 131°-132°.

c) 5.0 g (13.0 mmol) of rac-cis-1-[4-(6-hydroxy-2,3,3a,4,5,9b-hexahydro-1H-benzo[e]indol-3-yl)-butyl]-4,4-dimethyl-piperidine-2,6-dione were dissolved in 250 ml of toluene. The solution was treated with 2.76 g (3.8 ml, 27 mmol) of triethyl-amine and 1.68 g (1.43 ml, 16 mmol) of dimethylcarbamoyl chloride and 250 mg of 4-dimethylaminopyridine and stirred under an argon atmosphere overnight in an oil bath at an oil bath temperature of 110°. After cooling the organic phase was washed in succession with water, sodium bicarbonate solution and water, dried over magnesium sulphate and evaporated. The resulting brown oil (6.5 g) was chromatographed over a 30-fold amount of silica gel. The uniform eluates obtained in a thin-layer chromatogram using methylene chloride/ethyl acetate 1:1 were pooled and evaporated. The yellow oily base obtained (4.0 g) was converted into the hydrochloride in the usual manner, whereby there were obtained 4.0 g (62%) of rac-cis-3-[4-(4,4-dimethyl-2,6-dioxo-piperidin-1-yl)-butyl]-2,3,3a,4,5,9b-hexahydro-1H-benzo[e]indol-6-yl dimethylcarbamate hydrochloride as yellowish crystals of m.p. 190°-192° (dec.).

EXAMPLE 21 a) In an analogous manner to that described in Example 20a), rac-cis-1-[5-(6-methoxy-2,3,3a,4,5,9b-hexahydro-1H-benzo[e]indol-3-yl)pentyl]-4,4-dimethylpiperidine-2,6-dione was obtained by reacting rac-cis-2,3,3a,5,9b-hexahydro-6-methoxy-1H-benzo[e]indole with N-(5-bromopentyl)-3,3-dimethylglutarimide and was isolated in the form of the hydrochloride as yellowish crystals of m.p. 112°–114° (dec.); yield 59%.

b) In an analogous manner to that described in Example 20b), from 9.2 g (21.6 mmol) of rac-cis-1-[5-(6-methoxy-2,3,3a,4,5,9b-hexahydro-1H-benzo[e]indol-3-yl)pentyl]-4,4-dimethylpiperidine-2,6-dione using pyridine hydrochloride there were obtained 7.9 g of rac-cis-1-[5-(6-hydroxy-2,3,3a,4,5,9b-hexahydro-1H-benzo[e]indol-3-yl)pentyl]-4,4-dimethylpiperidine-2,6-dione; yellowish crystals of m.p. 133°–134° after crystallization from t-butyl methyl ether/hexane.

c) 5.0 g (12.54 mmol) of rac-cis-1-[5-(6-hydroxy-2,3,3a,4,5,9b-hexahydro-1H-benzo[e]indol-3-yl)pentyl]-4,4-dimethylpiperidine-2,6-dione were dissolved in 250 ml of toluene, treated with 2.67 g (3.7 ml; 26.4 mmol) of triethylamine, 1.62 g (1.4 ml, 15.4 mmol) of dimethylcarbamoyl chloride and 250 mg of 4-dimethylaminopyridine and stirred overnight in an oil bath at an oil bath temperature of 110°. After cooling the organic phase was washed in succession with water, sodium bicarbonate solution and water, dried over magnesium sulphate and evaporated. The brown oil obtained (6.3 g) was chromatographed over a 30-fold amount of silica gel with methylene chloride/ethyl acetate 1:1 and the purified base (5.9 g of pale yellow oil) was converted into the hydrochloride in the usual manner. After crystallization from ethyl acetate/ether there were obtained 5.1 g (80%) of rac-cis-3-[5-(4,4-dimethyl-2,6-dioxopiperidin-1-yl)pentyl]-2,3,3a,4,5,9b-hexahydro-1H-benzo[e]indol-6-yl dimethylcarbamate hydrochloride in the form of yellowish crystals of m.p. 133°–135° (dec.).

EXAMPLE 22 a) In an analogous manner to that described in Example 20a), from rac-cis-2,3,3a,4,5,9b-hexahydro-6-methoxy-1H-benzo[e]indole by reaction with N-(6-bromo-hexyl)-3,3-dimethylglutarimide there was obtained rac-cis-1-[6-(6-methoxy-2,3,3a,4,5,9b-hexahydro-1H-benzo[e]indol-3-yl)-hexyl]-4,4-dimethylpiperidine-2,6-dione; m.p. of the hydrochloride 99°–101°, yellowish crystals, yield 72%.

b) In an analogous manner to that described in Example 20b), from 9.2 g (21.56 mmol) of rac-cis-1-[6-(6-methoxy-2,3,3a,4,5,9b-hexahydro-1H-benzo[e]indol-3-yl)-hexyl]-4,4-dimethyl-piperidine-2,6-dione using pyridine hydrochloride there were obtained 7.9 g of (89%) rac-cis-1-[6-(6-hydroxy-2,3,3a,4,5,9b-hexahydro-1H-benzo[e]indol-3-yl)-hexyl]-4,4-dimethylpiperidine-2,6-dione; yellowish crystals of m.p. 98.5°–99° after crystallization from ether/hexane.

c) 5.0 g (12.12 mmol) of rac-cis-1-[6-(6-hydroxy-2,3,3a,4,5,9b-hexahydro-1H-benzo[e]indol-3-yl)hexyl]-4,4-dimethyl-piperidine-2,6-dione were dissolved in 200 ml of toluene, whereupon the solution was treated with 2.57 g (3.55 ml, 25.45 mmol) of triethylamine, 1.56 g (1.33 ml, 14.53 mmol) of dimethylcarbamoyl chloride and 250 mg of 4-dimethylamino-pyridine and stirred in an oil bath under an argon atmosphere overnight at an oil bath temperature of 110°. After cooling the organic phase was washed in succession with water, sodium bicarbonate solution and water, dried over magnesium sulphate and evaporated. The brown oil obtained (6.0 g) was chromatographed on a 30-fold amount of silica gel. After concentration of the elutes obtained using methylene chloride/ethyl acetate 1:1 there were obtained 3.0 g of yellowish rac-cis-3-[6-(4,4-dimethyl-2,6-dioxopiperidin-1-yl)hexyl]-2,3,3a,4,5,9b-hexahydro-1H-benzo[e]indol-6-yl dimethylcarbamate, which was converted into the hydrochloride in the usual manner. There were obtained 3.0 g (48%) of hydrochloride in the form of yellowish crystals of m.p. 144.5°–146°.

EXAMPLE 23

A suspension of 2.00 g (0.0067 mol) of (+)-cis-3-(2-cyclohexylethyl)-2,3,3a,4,5,9b-hexahydro-1H-benzo[e]indol-6-ol in 100 ml of acetonitrile was treated with 1.9 ml (0.013 mol) of triethylamine and 1.6 ml (0.027 mol) of methyl isocyanate. The mixture was boiled under reflux for 5 hours and the poured into aqueous sodium hydrogen carbonate solution, whereupon the mixture was extracted with methylene chloride. After drying the organic phase with sodium sulphate and distillation of the solvent the residue was chromatographed over silica gel with methylene chloride/methanol 20:1. The oil obtained was dissolved in ethanol and treated with an equimolar amount of ethanolic HCl. After concentration the residue was dissolved in methylene chloride, treated with active charcoal and sodium sulphate, filtered and the solvent was distilled off. The residue was suspended in ethyl acetate, filtered off and dried in a vacuum. There were obtained 1.58 g (60%) of (+)-cis-3-(2-cyclohexylethyl)-2,3,3a,4,5,9b-hexahydro-1H-benzo[e]indol-6-yl methylcarbamate hydrochloride with m.p. 209°–212°.

MS: m/e (% basis peak)=356 (M+, 9), 299 (4), 259 (100), 202 (66), 171 (6).

EXAMPLE 24

A suspension of 2.00 g (0.0067 mol) of (+)-cis-3-(2-cyclohexylethyl)-2,3,3a,4,5,9b-hexahydro-1H-benzo[e]indol-6-ol in 100 ml of acetonitrile was treated with 1.9 ml (0.013 mol) of triethylamine and 2.1 ml (0.027 mol) of ethyl isocyanate. The mixture was boiled under reflex for 20 hours and then poured into aqueous sodium hydrogen carbonate solution, whereupon the mixture was extracted with methylene chloride. After drying the organic phase with sodium sulphate and distillation of the solvent the residue was chromatographed over silica gel with methylene chloride/methanol 20:1. The oil obtained was dissolved in ethanol and treated with an equimolar amount of ethanolic HCl. After concentration the residue was dissolved in methylene chloride, treated with active charcoal and sodium sulphate, filtered and the solvent was distilled off in a vacuum. The residue was suspended in ethyl acetate, filtered off and dried in a vacuum. There were obtained 1.39 g (51%) of (+)-cis-3-(2-cyclohexylethyl)-2,3,3a,4,5,9b-hexahydro-1H-benzo[e]indol-6-yl ethylcarbamate hydro-chloride with m.p. 133°–136°.

MS: m/e (% basis peak)=370 (M+, 4), 299 (4), 273 (71), 202 (100), 171 (9), 145 (8).

EXAMPLE 25

A suspension of 2.00 g (0.0067 mol) of (+)-cis-3-(2-cyclohexylethyl)-2,3,3a,4,5,9b-hexahydro-1H-benzo[e]indol-6-ol in 100 ml of acetonitrile was treated with 1.9 ml (0.013 mol) of triethylamine and 2.6 ml (0.027 mol) of propyl isocyanate. The mixture was boiled under reflux for 20 hours and then poured into aqueous sodium hydrogen carbonate solution, whereupon the mixture was extracted with methylene chloride. After drying the organic phase with sodium sulphate and distillation of the solvent the residue was chromatographed over silica gel with methylene chloride/methanol 20:1. The oil obtained was dissolved in ethyl acetate and treated with an equimolar amount of ethanolic HCl. After drying with sodium sulphate and concentration to a volume of about 30 ml 1.78 g (63%) of (+)-cis-3-(2-cyclohexylethyl)-2,3,3a,4,5,9b-hexahydro-1H-benzo[e]indol-6-yl propylcarbamate hydrochloride with m.p. 125°–131° could be obtained by filtration.

MS: m/e (% basis peak)=384 (M+, 6), 287 (64), 202 (100), 171 (7).

EXAMPLE 26

A suspension of 2.00 g (0.0067 mol) of rac-cis-3-(2-cyclohexylethyl)-2,3,3a,4,5,9b-hexahydro-1H-benzo[e]indol-6-ol in 100 ml of acetonitrile was treated with 1.9 ml (0.013 mol) of triethylamine and 3.0 ml (0.027 mol) of butyl isocyanate. The mixture was boiled under reflux for 20 hours and then poured into aqueous sodium hydrogen carbonate solution, whereupon the mixture was extracted with methylene chloride. After drying the organic phase with sodium sulphate and distillation of the solvent the residue was chromatographed over silica gel with methylene chloride/methanol 20:1. The oil obtained was dissolved in methanol and treated with an equimolar amount of ethanolic HCl. After drying with sodium sulphate, concentration to a volume of about 30 ml and filtration there were obtained 1.11 g (38%) of rac-cis-3-(2-cyclohexylethyl)-2,3,3a,4,5,9b-hexahydro-1H-benzo[e]indol-6-yl butylcarbamate hydrochloride with m.p. 192°–194°.

MS: m/e (% basis peak)=398 (M+, 5), 301 (69), 202 (100).

EXAMPLE 27

A suspension of 2.00 g (0.0067 mol) of (+)-cis-3-(2-cyclohexylethyl)-2,3,3a,4,5,9b-hexahydro-1H-benzo[e]indol-6-ol in 100 ml of toluene was treated with 1.1 ml (0.008 mol) of triethyl-amine, 1.00 g (0.008 mol) of 4-dimethylaminopyridine and 1.00 g (0.008 mol) of ethylmethyl chloroformamide. The mixture was boiled under reflux for 4 hours and then poured into aqueous sodium hydrogen carbonate solution and extracted with methylene chloride. After drying the organic phase with sodium sulphate and distillation of the solvent the residue was chromatographed over silica gel with methylene chloride/methanol 20:1. The oil obtained was dissolved in ethyl acetate and treated with an equimolar amount of ethanolic HCl. After drying with sodium sulphate, concentration to a volume of about 25 ml and filtration there were obtained 24.9 g (88%) of (+)-cis-3-(2-cyclohexylethyl)-2,3,3a,4,5,9b-hexahydro-1H-benzo[e]indol-6-yl ethylmethylcarbamate hydrochloride with m.p. 181°–184°.

MS: m/e (% basis peak)=384 (M+, 9), 287 (100), 200 (3), 86 (24).

EXAMPLE 28 a) A solution of 1.00 g (0.005 mol) of rac-cis-2,3,3a,4,5,9b-Hexahydro-6-methoxy-1H-benzo[e]indole in 60 ml of ethyl methyl ketone was treated with 0.86 g (0.006 mol) of potassium carbonate, 0.29 g (0.002 mol) of sodium iodide and 1.50 g (0.005 mol) of N-(5-bromopentyl)phthalimide. The mixture was heated under reflux for 24 hours and, after cooling, treated with water. The mixture was extracted with ethyl acetate, the extracts were dried with sodium sulphate and the solvent was distilled off in a vacuum. Chromatography over silica gel with methylene chloride/methanol 20:1 gave 1.97 g (95%) of rac-N-[5-(cis-1,2,3a,4,5,9b-hexahydro-6-methoxy-3H-benzo[e]indol-3-yl)pentyl]phthalimide.

MS: m/e (% basis peak)=418 (M+, 7), 216 (100), 185 (7). M.p. of the hydrochloride 158°–160°.

b) A solution of 15.0 g (0.036 mol) of rac-N-[5-(cis-1,2,3a,4,5,9b-hexahydro-6-methoxy-3H-benzo[e]indol-3-yl)pentyl]phthalimide in 120 ml of methylene chloride was treated dropwise with a solution of 17.3 ml (0.179 mol) of boron tribromide in 60 ml of methylene chloride, whereupon the mixture was stirred at 0° for 2 hours. A solution of 20.4 g (0.51 mol) of sodium hydroxide in 70 ml of water was added dropwise while cooling with an ice bath. The mixture was poured into water, whereupon aqueous sodium hydrogen carbonate solution was added until a pH of 8 had been reached. The mixture was extracted with methylene chloride, the extracts were dried over sodium sulphate and the solvent was distilled off in a vacuum. Chromatography over silica gel with ethyl acetate yielded 3.1 g (21%) of rac-N-[5-(cis-1,2,3a,4,5,9b-hexahydro-6-hydroxy-3H-benzo[e]indol-3-yl)pentyl]phthalimide as a brown oil. A small sample was converted with ethanolic HCl into the hydrochloride, m.p. 246°–248°.

MS: m/e (% basis peak)=404 (M+, 7), 202 (100), 160 (6), 145 (5).

c) A mixture of 2.50 g (0.006 mol) of rac-N-[5-(cis-1,2,3a,4,5,9b-hexahydro-6-hydroxy-3H-benzo[e]indol-3-yl)pentyl]phthalimide, 0.68 g (0.007 mol) of dimethylcarbamoyl chloride, 1.0 ml (0.007 mol) of triethylamine and 0.91 g (0.007 mol) of 4-dimethylaminopyridine in 100 ml of toluene was boiled under reflux for 4 hours and then poured into aqueous sodium hydrogen carbonate solution. The mixture was extracted with toluene, the extracts were dried with sodium sulphate and the solvent was distilled off in a vacuum. The residue was chromatographed over silica gel with ethyl acetate and there were obtained 2.39 g (81%) of rac-3-[5-(1,3-dioxo-isoindolin-2-yl)pentyl]-2,3,3a,4,5,9b-hexahydro-1H-cis-benzo[e]indol-6-yl dimethylcarbamate as a yellow oil. 0.6 g of this oil was converted with ethanolic HCl into the corresponding hydrochloride.

MS: m/e (% basis peak)=475 (M+, 7), 273 (100), 160 (7), 72 (50).

EXAMPLE 29 a) A solution of 8.55 g (0.02 mol) of rac-cis-N-[4-(1,2,3a,4,5,9b-hexahydro-6-methoxy-3H-benzo[e]indol-3-yl)butyl]phthalimide in 250 ml of acetic acid was treated with 3.88 g (0.06 mol) of zinc powder. The mixture was boiled under reflux for 1.25 hours and the acetic acid was then distilled off. The residue was taken up in ethyl acetate and extracted with water and saturated sodium chloride solution. The organic phase was dried with sodium sulphate and concentrated, whereupon the residue was chromatographed over silica gel with ethyl acetate/methanol 9:1. There were obtained 1.19 g (14%) of rac-2-[4-(6-methoxy-2,3,3a,4,5,9b-hexahydro-1H-cis-benzo[e]indol-3-yl)butyl]isoindolin-1-one as a yellow foam.

MS: m/e (% basis peak)=390 (M+, 12), 216 (100), 202 (19), 146 (14), 91 (10).

b) A solution of 1.14 g (0.003 mol) of rac-2-[4-(6-methoxy-2,3,3a,4,5,9b-hexahydro-1H-cis-benzo[e]indol-3-yl)butyl] isoindolin-1-one in 30 ml of methylene chloride was treated dropwise with 0° with a solution of 1.4 ml (0.015 mol) of boron tribromide in 10 ml of methylene chloride, whereupon the mixture was stirred at 0° for 1.5 hours. A solution of 1.65 g (0.04 mol) of sodium hydroxide in 20 ml of water was added dropwise while cooling with an ice bath, whereupon the mixture was stirred for a further 30 minutes. Then, the mixture was poured into aqueous sodium bicarbonate solution and extracted with methylene chloride. The organic phase was dried with sodium sulphate and concentrated. Chromatography of the residue over silica gel with CH$_2$Cl$_2$/MeOH 9:1 yielded 0.61 g (55%) of rac-3-[4-(1-oxo-isoindolin-2-yl)butyl]-2,3,3a,4,5,9b-hexahydro-1H-cis-benzo[e]indol-6-ol as a white foam. 0.10 g of this was treated with 0.5 ml of 8.6 molar ethanolic hydrochloric acid and concentrated. The residue was dissolved in methylene chloride. After drying with Na$_2$SO$_4$ and concentration there was obtained 0.08 g of hydrochloride as a white foam.

MS: m/e (% basis peak)=376 (M+, 8), 202 (100), 188 (18), 171 (6), 146 (12).

c) A mixture of 0.50 g (0.0013 mol) of rac-3-[4-(1-oxo-isoindolin-2-yl)butyl]-2,3,3a,4,5,9b-hexahydro-1H-cis-benzo[e]indol-6-ol, 0.15 ml (0.0016 mol) of dimethylcarbamoyl chloride, 0.49 ml (0.0035 mol) of triethylamine and 0.20 g (0.0016 mol) of 4-dimethylaminopyridine in 30 ml of toluene was boiled under reflux for 2 hours. The solvent was distilled off in a vacuum, the residue was dissolved in methylene chloride and extracted with water and saturated aqueous sodium chloride solution. After drying with sodium sulphate, concentration and chromatography over silica gel with methylene chloride/methanol 9:1 there were obtained 560 mg of yellow oil which was treated with 2 ml of 8.6 molar ethanolic hydrochloric acid. The mixture was concentrated, the residue was dissolved with methylene chloride, dried with sodium sulphate, filtered and the solvent was distilled off. There were obtained 455 mg (71%) of rac-3-[4-(1-oxo-indolin-2-yl)butyl]-2,3,3a,4,5,9b-hexahydro-1H-cis-benzo[e]indol-6-yl dimethylcarbamate hydrochloride as a white foam.

MS: m/e (% basis peak)=447 (M+, 16), 273 (100), 259 (14), 146 (15), 72 (75).

EXAMPLE 30 a) A solution of 3.10 g (0.007 mol) of rac-N-[5-(cis-1,2,3a,4,5,9b-hexahydro-3H-benzo[e]indol-3-yl)pentyl]phthalimide in 100 ml of glacial acetic acid was treated with 1.0 g of 10% palladium/charcoal and hydrogenated at 60° for 6 hours at 20 bar hydrogen pressure. The acetic acid was distilled off and the residue was taken up in methylene chloride. The solution was washed with 2N sodium hydroxide solution, dried with sodium sulphate and concentrated. Chromatography over silica gel with ethyl acetate/methanol 19:1 yielded 0.80 g (27%) of rac-cis-2-[5-(6-methoxy-2,3,3a,4,5,9b-hexahydro-1H-benzo[e]indol-3-yl)pentyl]isoindolin-1-one as a yellow oil [MS: m/e (% basis peak)=404 (M+, 6), 216 (100), 202 (8), 185 (6), 146 (7)] as well as 1.64 g (55%) of rac-2-[5-(6-methoxy-2,3,3a,4,5,9b-hexahydro-1H-cis-benzo[e]indol-6-yl)pentyl]octahydro-cis-isoindole-1,3-dione as a yellow oil [MS: m/e (% basis peak)=424 (M+, 7), 216 (100), 185 (5)].

b) A mixture of 0.8 g (0.002 mol) of rac-cis-2-[5-(6-methoxy-2,3,3a,4,5,9b-hexahydro-1H-benzo[e]indol-3-yl)pentyl]isoindolin-1-one an 8.0 g (0.07 mol) of pyridine hydrochloride was treated with 3 drops of dimethylformamide and stirred at 180° for 2 hours. After cooling the mixture was poured into aqueous sodium hydrogen carbonate solution and extracted with ethyl acetate to which about 1% methanol had been added. After drying with sodium sulphate, concentration and chromatography over silica gel with methylene chloride/methanol/ammoniacal water 110:8:1 there was obtained 0.5 g (65%) of rac-2-[5-(6-hydroxy-2,3,3a,4,5,9b-hexahydro-1H-cis-benzo[e]indol-3-yl)pentyl]isoindolin-1-one. 120 mg of this were converted into the hydrochloride.

MS: m/e (% basis peak)=390 (M+, 7), 202 (100), 188 (9), 146 (19).

c) A mixture of 0.33 g (0.0008 mol) of rac-2-[5-(6-hydroxy-2,3,3a,4,5,9b-hexahydro-1H-cis-benzo[e]indol-3-yl)pentyl]isoindolin-1-one, 0.09 ml (0.001 mol) of dimethylcarbamoyl chloride, 0.14 ml (0.001 mol) of triethylamine and 0.12 g (0.001 mol) of 4-dimethylaminopyridine in 10 ml of toluene was boiled under reflux for 3 hours and then poured into aqueous sodium hydrogen carbonate solution, whereupon the mixture was extracted with methylene chloride. After drying with sodium sulphate and concentration the residue was chromatographed over silia gel with methylene chloride/methanol/ammoniacal water 110:8:1. The resulting colorless oil was treated with ethanolic HCl, whereupon the solution was dried with sodium sulphate and concentrated. There was obtained 0.3 g (71%) of rac-3-[5-(1-oxo-isoindolin-2-yl)pentyl]-2,3,3a,4,5,9b-hexahydro-1H-cis-benzo[e]indol-6-yl dimethylcarbamate hydrochloride as a white foam.

MS: m/e (% basis peak)=461 (M+, 3), 389 (2), 273 (54), 146 (19), 72 (100).

EXAMPLE 31 a) A mixture of 1.50 g (0.0035 mol) of rac-2-[5-(6-methoxy-2,3,3a,4,5,9b-hexahydro-1H-cis-benzo[e]indol-6-yl)pentyl]octahydro-cis-isoindole-1,3-dione and 15.0 g (0.13 mol) of pyridine hydrochloride was treated with 6 drops of dimethylformamide and stirred at 180° for 2 hours. After cooling the mixture was poured into aqueous sodium hydrogen carbonate solution and extracted with methylene chloride. After drying with sodium sulphate, concentration and chromatography over silica gel with methylene chloride/methanol/ammoniacal water 110:8:1 there was obtained 0.66 g (69%) of rac-2-[5-(6-hydroxy-2,3,3a,4,5,9b-hexahydro-1H-cis-benzo[e]indol-3-yl)pentyl]octahydro-cis-isoindole-1,3-dione. A small sample was converted into the hydrochloride.

MS: m/e (% basis peak)=410 (M+, 8) 202 (100), 171 (6), 81 (10).

b) A mixture of 0.50 g (0.001 mol) of rac-2-[5-(6-hydroxy-2,3,3a,4,5,9b-hexahydro-1H-cis-benzo[e]indol-3-yl)pentyl]octahydro-cis-isoindole-1,3-dione, 0.14 ml (0.0015 mol) of dimethylcarbamoyl chloride, 0.2 ml (0.0015 mol) of triethylamine and 0.18 g (0.0015 mol) of 4-dimethylaminopyridine in 20 ml of toluene was boiled under reflux for 3 hours and then poured into aqueous sodium hydrogen carbonate solution and extracted with methylene chloride. After drying and concentration the residue was chromatographed over silica gel with ethyl acetate/methanol 9:1. The colorless oil obtained was treated with ethanolic HCl and the solution was dried with sodium sulphate and concentrated. There was obtained 0.5 g (85%) of rac-3-[5-(1,3-dioxo-octahydro-cis-isoindol-2-yl)pentyl]-2,3,3a,4,5,9b-hexahydro-1H-cis-benzo[e]indol-6-yl dimethylcarbamate hydrochloride as a white foam.

MS: m/e (% basis peak)=481 (M+, 8), 273 (100), 200 (5), 72 (90).

EXAMPLE 32 a) A solution of 9.72 g (0.024 mol) of rac-cis-N-[6-(1,2,3a, 4,5,9b-hexahydro-6-methoxy-3H-benzo[e]indol-3-yl)hexyl]phthalimide in 200 ml of acetic acid was treated with 4.70 g (0.072 mol) of zinc powder. The mixture was boiled under reflux for 1.25 hours and the acetic acid was then distilled off. The residue was taken up in ethyl acetate and extracted with water and saturated sodium chloride solution. The organic phase was dried with sodium sulphate and concentrated, whereupon the residue was chromatographed over silica gel with ethyl acetate/methanol 9:1. There was obtained 0.98 g (10%) of rac-2[6-(6-methoxy-2,3,3a,4,5,9b-hexahydro-1H-cis-benz[e]indol-3-yl)hexyl]isoindolin-1-one as a yellow oil.

MS: m/e (% basis peak)=418 (M+, 10), 216 (100), 146 (20).

b) A solution of 0.92 g (0.002 mol) of rac-2-[6-(6-methoxy-2,3,3a,4,5,9b-hexahydro-1H-cis-benz[e]indol-3-yl)hexyl]isoindolin-1-one in 30 ml of methylene chloride was treated dropwise at 0° with a solution of 1.06 ml (0.012 mol) of boron tribromide in 10 ml of methylene chloride, whereupon the mixture was stirred at 0° for 2 hours. A solution of 1.23 g (0.03 mol) of sodium hydroxide in 20 ml of water was added dropwise while cooling with an ice bath, whereupon the mixture was stirred for a further 30 minutes. Then, the mixture was poured into aqueous sodium hydrogen carbonate solution and extracted with methylene chloride. Drying with sodium sulphate, concentration and chromatography over silica gel with methylene chloride/methanol 14:1 yielded 0.41 g (46%) of rac-3-[6-(1-oxo-isoindolin-2yl)hexyl]-2,3,3a,4,5,9b-hexahydro-1H-cis-benzo[e]indol-6-ol as a white foam.

MS: m/e (% basis peak)=404 (M+, 7), 202 (100), 121 (41).

c) A mixture of 0.41 g (0.001 mol) of rac-3-[6-(1-oxo-isoindolin-2yl)hexyl]-2,3,3a,4,5,9b-hexahydro-1H-cis-benzo[e]indol-6-ol, 0.11 ml (0.0012 mol) of dimethylcarbamoyl chloride, 0.31 ml (0.0022 mol) of triethylamine and 0.15 g (0.0012 mol) of 4-dimethylaminopyridine in 50 ml of toluene was boiled under reflux for 1.5 hours. The solvent was distilled off in a vacuum, the residue was dissolved in methylene chloride and extracted with water and saturated aqueous sodium chloride solution. After drying with sodium sulphate, concentration and chromatography over silica gel with methylene chloride/methanol 19:1 there was obtained 0.39 g of crude product which was treated with 0.18 ml of 8.6 molar ethanolic hydrochloric acid. The solution was concentrated, the residue was dissolved in methylene chloride, the solution was treated with sodium sulphate and active charcoal, filtered and the solvent was distilled off. There was thus obtained 0.3 g (58%) of rac-3-[6(1-oxo-isoindolin-2-yl)hexyl]-2,3,3a,4,5,9b-hexahydro-1H-cis-benzo[e]indol-6-yl dimethylcarbamate hydrochloride as a beige foam.

MS: m/e (% basis peak)=475 (M+, 7), 274 (18), 273 (100), 146 (10), 72 (54).

EXAMPLE 33 a) A solution of 5.00 g (0.025 mol) of rac-cis-2,3,3a,4,5,9b-hexahydro-6-methoxy-1H-benzo[e]indole, 4.5 g (0.025 mol) of γ-chlorobutyrophenone and 6.9 ml (0.05 mol) of triethylamine in 150 ml of toluene was boiled under reflux for 2 days. Filtration, concentration and chromatography over silica gel with ethyl acetate/hexane 1:1 gave 3.18 g (37%) of rac-4-(6-methoxy-2,3,3a,4,5,9b-hexahydro-1H-cis-benzo[e]indol-3-yl)-1-phenylbutan-1-one as a brown oil. A sample was converted with ethanolic hydrochloric acid into the hydrochloride. M.p. of the hydrochloride 178°–182°.

MS: m/e (% basis peak)=349 (M+, 8), 229 (34), 216 (100), 214 (19), 185 (8), 159 (8), 147 (8), 105 (19), 77 (17), 71 (14).

b) A solution of 2.41 g (0.007 mol) of rac-4-(6-methoxy-2,3,3a,4,5,9b-hexahydro-1H-cis-benzo[e]indol-3-yl)-1-phenylbutan-1-one in 100 ml of 48% hydrobromic acid was boiled under reflux for 2 hours. After concentration the residue was taken up in methylene chloride and water. The aqueous phase was treated with 2N sodium hydroxide solution until a pH value of 14 had been reached. Then, the mixture was extracted once with saturated aqueous ammonium chloride solution and once with saturated aqueous sodium hydrogen carbonate solution. After drying the organic phase with sodium sulphate and concentration the residue was chromatographed over silica gel with ethyl acetate. The solid obtained was dissolved in a mixture of ethanol and methylene chloride, treated with 0.8 ml of 8.8M aqueous hydrobromic acid and the solvent was distilled off. There were obtained 21 g (73%) of rac-4-(6-hydroxy-2,3,3a,4,5,9b-hexahydro-1H-cis-benzo[e]indol-3-yl)-1-phenylbutanone hydrobromide as brown crystals. A sample was recrystallized from ethanol/ether and showed a m.p. of 217°–220°.

MS: m/e (% basis peak)=335 (M+, 7), 215 (41), 202 (100), 171 (8), 145 (9), 105 (16).

c) A mixture of 1.00 g (0.003 mol) of rac-4-(6-hydroxy-2,3,3a,4,5,9b-hexahydro-1H-cis-benzo[e]indol-3-yl)-1-phenylbutanone hydrobromide, 0.33 ml (0.0036 mol) of dimethylcarbamoyl chloride, 1.0 ml (0.007 mol) of triethylamine and 0.44 g (0.0036 mol) of 4-dimethylaminopyridine in 30 ml of toluene was boiled under reflux for 3 hours. The solvent was distilled off in a vacuum, the residue was dissolved in methylene chloride and the solution was extracted with water and saturated aqueous sodium chloride solution. After drying the organic phase with sodium sulphate, concentration and chromatography over silica gel with ethyl acetate/methanol 19:1 there was obtained 0.92 g of yellow oil which was dissolved in ethanol. The solution was treated with 0.36 ml of 8.8M aqueous hydrobromic acid and concentrated. The residue was dissolved in hot ethanol and treated with active charcoal. After filtration while hot the solvent was distilled off and the residue was suspended in ethyl acetate. After filtration there was obtained 0.87 g (74%) of rac-3-(4-oxo-4-phenylbutyl)-2,3,3a,4,5,9b-hexahydro-1H-cis-benzo[e]indol-6-yl-dimethylcarbamate hydrobromide as beige crystals with m.p. 183°–186°.

MS: m/e (% basis peak)=406 (M+, 4), 286 (33), 273 (100), 147 (14), 105 (21), 72 (91).

EXAMPLE 34 a) A solution of 8.00 g (0.039 mol) of rac-cis-2,3,3a,4,5,9b-Hexahydro-6-methoxy-1H-benzo[e]indole, 9.49 g (0.039 mol) of 5-bromo-1-phenylpentan-1-one and 10.9 ml (0.079 mol) of triethylamine in 240 ml of toluene was boiled under reflux for 2 days. The solvent was distilled off in a vacuum, the residue was taken up in methylene chloride and the solution was extracted with water and saturated sodium chloride solution. Drying of the organic phase over sodium sulphate, concentration and chromatography over silica gel with ethyl acetate gave 9.7 g (68%) of rac-5-(6-methoxy-2,3,3a,4,5,9b-hexahydro-1H-cis-benzo[e]indol-3-yl)-1-phenylpentan-1-one as a brown oil. A sample was converted with ethanolic hydrochloric acid into the hydrochloride. M.p. of the hydrochloride 145°–150°.

MS (hydrochloride): m/e (% basis peak)=363 (M+, 12), 216 (100), 185 (7), 159 (5), 105 (9).

b) A suspension of 9.50 g (0.026 mol) of rac-5-(6-methoxy-2,3,3a,4,5,9b-hexahydro-1H-cis-benzo[e]indol-3-yl)-1-phenylpentan-1-one in 200 ml of 48% hydrobromic acid was boiled under reflux for 2 hours. After concentration the residue was taken up in methylene chloride. The aqueous phase was treated with 2N sodium hydroxide solution until a pH value of 14 had been reached. Then, the mixture was extracted with saturated aqueous ammonium chloride solution. Drying of the organic phase with sodium sulphate, concentration and chromatography over silica gel with ethyl acetate yielded 8.43 g (92%) of rac-3-(5-oxo-5-phenylpentyl)-2,3,3a,4,5,9b-hexahydro-1H-cis-benzo[e]indol-6-ol as brown crystals. A sample was converted with 8.8N aqueous hydrobromic acid into the hydrobromide. M.p. of the hydro-bromide: 261°–264°.

MS (hydrobromide): m/e (% basis peak)=349 (M+, 9), 202 (100), 171 (5), 145 (7), 105 (13), 77 (8).

c) A mixture of 4.0 g (0.011 mol) of rac-3-(5-oxo-5-phenylpentyl)-2,3,3a,4,5,9b-hexahydro-1H-cis-benzo[e]indol-6-ol, 1.3 ml (0.014 mol) of dimethylcarbamoyl chloride, 1.9 ml (0.014 mol) of triethylamine and 1.68 g (0.014 mol) of 4-dimethylaminopyridine in 120 ml of toluene was boiled under reflux for 3 hours. The solvent was distilled off in a vacuum, the residue was dissolved in methylene chloride and the solution was extracted with water and saturated aqueous sodium chloride solution. After drying the organic phase with sodium sulphate, concentration and chromatography over silica gel with ethyl acetate/methanol 19:1 there were obtained 3.9 g of yellow oil which was dissolved in ethanol. The solution was treated with 1.8 ml of 8.6M ethanolic HCl, treated with active charcoal and concentrated. The residue was suspended in ethyl acetate and filtered. There were obtained 3.64 g (70%) of rac-3-(5-oxo-5-phenylpentyl)-2,3,3a,4,5,9b-hexahydro-1H-cis-benz[e]indol-6-yl dimethylcarbamate hydrochloride as an amorphous powder.

MS: m/e (% basis peak)=420 (M+, 8), 273 (100), 200 (3), 105 (17), 77 (11), 72 (70).

EXAMPLE 35 a) A solution of 10.0 g (0.049 mol) of rac-cis-2,3,3a,4,5,9b-hexahydro-6-methoxy-1H-benzo[e]indole in 250 ml of 48% hydrobromic acid was boiled under reflux for 2 hours. The hydrobromic acid was distilled off, the residue was dissolved in a mixture of 30 ml of methanol, 500 ml of methylene chloride and about 200 ml of water and the solution was treated with 2N sodium hydroxide solution until a pH value of 10–11 had been reached. Subsequently, saturated aqueous ammonium chloride solution and hydrochloric acid were added thereto until a pH value of 7.5 had been reached. The mixture was extracted twice with 200 ml of a 20% solution of methanol in methylene chloride each time and four times with 150 ml of chloroform each time. After drying the extracts with sodium sulphate and concentration the residue was dissolved in 200 ml of methanol and the product was precipitated by the addition of ether. Filtration gave 9.57 g of rac-2,3,3a,4,5,9b-hexahydro-1H-cis-benzo[e]indol-6-ol (partly as the hydrochloride).

MS: m/e (% basis peak)=189 (M+, 100), 172 (16), 145 (35), 131 (15), 115 (15), 68 (15), 56 (48).

b) A suspension of 3.0 g (0.016 mol) of rac-2,3,3a,4,5,9b-hexahydro-1H-cis-benzo[e]indol-6-ol, 5.2 g (0.017 mol) of 5-bromo-3',4'-dimethoxyvalerophenone (obtainable in analogy to the procedure described in EP-A2-310126) and 2.4 ml (0.017 mol) of triethylamine in 150 ml of toluene was boiled under reflux for 22 hours. After cooling the mixture was poured into aqueous sodium hydrogen carbonate solution and extracted ethyl acetate. Chromatography over silica gel with methylene chloride/methanol 20:1 gave 0.94 g (15%) of rac-5-(6-hydroxy-2,3,3a,4,5,9b-hexahydro-1H-cis-benzo[e]indol-3-yl)-1-(3,4-dimethoxyphenyl)-pentan-1-one as a solid. A small sample was converted with ethanolic HCl into the hydrochloride; m.p. of the hydrochloride 230°–232°.

MS: m/e (% basis peak)=409 (M+, 12), 202 (100), 188 (5), 165 (5), 145 (5).

c) A mixture of 0.70 g (0.0017 mol) of rac-5-(6-hydroxy-2,3,3a,4,5,9b-hexahydro-1H-cis-benzo[e]indol-3-yl)-1-(3,4-dimethoxyphenyl)-pentan-1-one, 0.19 ml (0.002 mol) of dimethylcarbamoyl chloride, 0.28 ml (0.002 mol) of triethylamine and 0.25 g (0.002 mol) of 4-dimethylaminopyridine in 40 ml of toluene was boiled under reflux for 21 hours and then poured into aqueous sodium hydrogen carbonate solution. The mixture was extracted with ethyl acetate and chromatographed over silica gel with methylene chloride/methanol 20:1. The oil obtained was dissolved in a small amount of methanol. After the addition of an equimolar amount of ethanolic HCl the mixture was dried with sodium sulphate and concentrated. There was obtained 0.84 g (95%) of rac-3-[5-(3,4-dimethoxyphenyl)-5-oxo-pentyl]-2,3,3a,4,5,9b-hexahydro-1H-cis-benzo[e]indol-6-yl dimethylcarbamate hydrochloride as an amorphous powder.

MS: m/e (% basis peak)=480 (M+,8), 273 (100), 259 (5), 221 (5), 200 (5), 165 (11), 72 (70).

EXAMPLE 36 a) A suspension of 3.10 g (0.014 mol) of rac-2,3,3a,4,5,9b-hexahydro-1H-cis-benzo[e]indol-6-ol, 4.80 g (0.015 mol) of 6-bromo-(3,4-dimethoxyphenyl)hexan-1-one (obtainable according to EP-A-2-310126) and 3.8 ml (0.027 mol) of triethylamine in 150 ml of toluene was boiled under reflux for 16 hours and, after cooling, poured into aqueous sodium hydrogen carbonate solution, whereupon the mixture was extracted with ethyl acetate. Chromatography of the residue, which remained upon evaporation of the extract, over silica gel with methylene chloride/methanol 20:1 gave 1.6 g (17%) of rac-6-(6-hydroxy-2,3,3a,4,5,9b-hexa-hydro-1H-cis-benzo[e]indol-3-yl)-1-(3,4-dimethoxyphenyl) hexan-1-one as a brown solid. A small sample was converted with ethanolic HCl into the hydrochloride; m.p. 165°–168°.

MS: m/e (% basis peak)=423 (M+, 17), 202 (100), 165 (8), 145 (5).

b) A mixture of 1.30 g (0.003 mol) of rac-6-(6-hydroxy-2,3,3a,4,5,9b-hexahydro-1H-cis-benzo[e]indol-3-yl)-1-(3,4-dimethoxyphenyl)hexan-1-one, 0.34 g (0.0037 mol) of dimethylcarbamoyl chloride, 0.52 ml (0.0037 mol) of triethylamine and 0.45 g (0.0037 mol) of 4-dimethylaminopyridine in 80 ml of toluene was boiled under reflux for 21 hours and then poured into aqueous sodium hydrogen carbonate solution, whereupon the mixture was extracted with ethyl acetate. Chromatography of the residue, which remained upon evaporation of the extract, over silica gel with methylene chloride/methanol 20:1 gave an oil which was dissolved in 20 ml of ethanol and treated with an equimolar amount of ethanolic HCl. After concentration the residue was dissolved in methylene chloride. The solution was treated with sodium sulphate and active charcoal, filtered and the filtrate was concentrated. The residue was suspended in ether, whereupon the suspension was filtered. There was obtained 0.92 g (56%) of rac-3-[6-(3,4-dimethoxyphenyl)-6-oxohexyl]-2,3,3a,4,5,9b-hexahydro-1H-cis-benzo[e]indol-yl dimethylcarbamate hydrochloride as an amorphous powder.

MS: m/e (% basis peak)=494 (M+, 10), 273 (100), 165 (12), 72 (72).

EXAMPLE 37 a) A suspension of 2.03 g (0.01 mol) of rac-cis-2,3,3a,4,5,9b-hexahydro-6-methoxy-1H-benzo[e]indole, 2.76 g (0.02 mol) of potassium carbonate, 0.2 g (0.001 mol) of sodium iodide and 4.00 g (0.02 mol) of γ-chloro-p-fluorobutyrophenone in 40 ml of ethyl methyl ketone was boiled under reflux for 18 hours and then poured into water, whereupon the mixture was extracted at pH 8–9 with ethyl acetate. Chromatography of the residue, which remained upon evaporation of the extract, over silica gel with ethyl acetate/hexane 2:1 yielded 3.35 g (91%) of rac-1-(4-fluorophenyl)-4-(6-methoxy-2,3,3a,4,5,9b-hexahydro-1H-cis-benzo[e]indol-3-yl)butan-1-one as a colorless oil.

MS: m/e (% basis peak)=367 (M+, 9), 229 (32), 216 (100), 185 (7), 165 (7), 159 (7), 123 (18).

b) 3.3 g (0.009 mol) of rac-1-(4-fluorophenyl)-4-(6-methoxy-2,3,3a,4,5,9b-hexahydro-1H-cis-benzo[e]indol-3-yl)butan-1-one in 200 ml of 48% aqueous hydrobromic acid was boiled under reflux for 1 hour. After concentration the residue was poured into water and extracted at pH 8–9 with methylene chloride. Chromatography of the residue, which remained upon evaporation of the extract, over silica gel with methylene chloride/methanol 20:1 yielded 2.45 g (77%) of rac-1-(4-fluorophenyl)-4-(6-hydroxy-2,3,3a,4,5,9b-hexahydro-1H-cis-benzo[e]indol-3-yl)butan-1-one as a grey solid. A small sample was converted with an equimolar amount of ethanolic HCl into the hydrochloride; m.p. 232°–234°.

MS: m/e (% basis peak)=353 (M+, 8), 215 (37), 202 (100), 165 (8), 145 (11), 123 (27), 95 (17).

c) A mixture of 2.00 g (0.006 mol) of rac-1-(4-fluorophenyl)-4-(6-hydroxy-2,3,3a,4,5,9b-hexahydro-1H-cis-benzo[e]indol-3-yl)butan-1-one, 0.64 ml (0.007 mol) of dimethylcarbamoyl chloride, 1.0 ml (0.007 mol) of triethylamine and 0.85 g (0.007 mol) of 4-dimethylaminopyridine in 100 ml of toluene was boiled under reflux for 5 hours and then poured into aqueous sodium hydrogen carbonate solution, whereupon the mixture was extracted with ethyl acetate. Chromatography of the residue, which remained upon evaporation of the extract, over silica gel with methylene chloride/methanol 40:1 yielded 2.14 g of solid. This was dissolved in 15 ml of ethyl acetate, treated with 35 ml of n-hexane and cooled in a refrigerator. After filtration and drying there were obtained 1.59 g (66%) of rac-3-[4-(4-fluorophenyl)-4-oxobutyl]-2,3,3a,4,5,9b-hexahydro-1H-cis-benzo[e]indol-6-yl dimethylcarbamate as beige crystals with m.p. 95°–97°.

MS: m/e (% basis peak)=424 (M+, 1), 286 (9), 273 (41), 165 (5), 123 (23), 95 (16), 72 (100).

EXAMPLE 38

A solution of 6.40 g (0.014 mol) of rac-cis-2,3,3a,4,5,9b-hexahydro-3-(4-phthalimidobutyl)-1H-benzo[e]indol-6-yl dimethylcarbamate and 7.7 ml (0.037 mol) of hydrazine hydrate in 200 ml of ethanol was boiled under reflux for 2 hours and then stirred at room temperature overnight. After filtration the solvent was distilled off and the residue was dissolved in methylene chloride. After extraction with water and with saturated aqueous sodium chloride solution the organic phase was dried with sodium sulphate and concentrated. There were obtained 3.66 g (80%) of rac-3-(4-aminobutyl)-2,3,3a,4,5,9b-hexahydro-1H-cis-benzo[e]indol-6-yl dimethylcarbamate as a dark oil. 0.2 g of this was dissolved in ethanol, treated with 0.1 ml of 8.6M ethanolic HCl and concentrated. The residue was dissolved in methylene chloride and treated with active charcoal and sodium sulphate. After filtration and concentration the residue was again dissolved in 2 ml of methylene chloride and 20 ml of ether and then 30 ml of hexane were added thereto while stirring. After stirring for 1 hour the solid was filtered off and dried. There was obtained 0.17 g of rac-3-(4-aminobutyl)-2,3,3a,4,5,9b-hexahydro-1H-cis-benzo[e]indol-6-yl dimethylcarbamate hydrochloride as a hygroscopic solid.

MS: m/e (% basis peak)=331 (M+, 6), 273 (74), 259 (12), 216 (11), 72 (100).

EXAMPLE 39

A solution of 3.46 g (0.01 mol) of rac-3-(4-aminobutyl)-2,3,3a,4,5,9b-hexahydro-1H-cis-benzo[e]indol-6-yl dimethylcarbamate, 2.10 g (0.01 mol) of 4-(methanesulfonyl)benzoic acid, 4.00 g (0.01 mol) of 2-(1H-benzotriazol-1-yl)-1,1,3,3-tetramethyluronium hexafluorophosphate and 2.9 ml (0.021 mol) of triethylamine in 80 ml dimethylformamide was stirred at room temperature for 22 hours and then poured into aqueous sodium hydrogen carbonate solution, whereupon the mixture was extracted with methylene chloride. After drying the extract with sodium sulphate and concentration the residue was chromatographed three times over silica gel, firstly with methylene chloride/methanol 9:1, then with ethyl acetate/methanol 4:1 and finally with methylene chloride/methanol 20:1. The solid obtained was dissolved in ethyl acetate/methanol and treated with an equimolar amount of ethanolic HCl. The solution obtained was dried with sodium sulphate and filtered. Distillation of the solvent gave 2.10 g (37%) of rac-cis-3-[4-(4-methanesulfonyl-benzoylamino)-butyl]-2,3,3a,4,5,9b-hexahydro-1H-benzo[e]indol-6-yl dimethylcarbamate hydrochloride as a beige foam.

MS: m/e (% basis peak)=513 (M+, 7), 273 (100), 259 (5), 216 (7), 183 (12), 121 (5), 107 (5), 72 (65).

EXAMPLE 40

A solution of 1.79 g (0.004 mol) of rac-3-[5-(1,3-dioxoisoindolin-2-yl)pentyl]-2,3,3a,4,5,9b-hexahydro-1H-cis-benzo[e]indol-6-yl dimethylcarbamate and 0.48 ml (0.01 mol) of hydrazine hydrate in 35 ml of ethanol was boiled under reflux for 2 hours and then stirred at room temperature overnight. After filtration the solvent was distilled off and the residue was dissolved in methylene chloride. After extraction with water the organic phase was dried with sodium sulphate and concentrated. Chromatography of the residue over silica gel with methylene chloride/methanol/ammoniacal water yielded 0.9 g (69%) of rac-3-(5-aminopentyl)-2,3,3a,4,5,9b-hexahydro-1H-cis-benzo[e]indol-6-yl dimethylcarbamate as a pale yellow oil. A small sample was converted with an equimolar amount of ethanolic HCl into the bis-hydrochloride.

MS: m/e (% basis peak)=345 (M+, 6), 273 (100), 259 (14), 84 (12), 72 (73).

EXAMPLE 41

A solution of 0.60 g (0.002 mol) of rac-3-(5-aminopentyl)-2,3,3a,4,5,9b-hexahydro-1H-cis-benzo[e]indol-6-yl dimethylcarbamate, 0.35 g (0.002 mol) of 4-(methanesulfonyl)-benzoic acid, 0.66 g (0.002 mol) of 2-(1H-benzotriazol-1-yl)-1,1,3,3-tetramethyluronium hexafluorophosphate and 0.48 ml (0.003 mol) of triethylamine in 10 ml of dimethylformamide was stirred at room temperature overnight and then poured into aqueous sodium hydrogen carbonate solution, whereupon the mixture was extracted with methylene chloride. After drying the organic phase with sodium sulphate and concentration the residue was chromatographed twice over silica gel, firstly with methylene chloride/methanol/ammoniacal water 105:8:1 and then with ethyl acetate/methanol 4:1. The resulting oil (0.6 g) was converted with an equimolar amount of ethanolic HCl into the hydrochloride. There was obtained 0.57 g (58%) of rac-cis-3-[5-(4-methanesulfonylbenzoylamino)pentyl]-2,3,3a,4,5,9b-hexahydro-1H-benzo[e]indol-6-yl dimethylcarbamate hydrochloride as a white, amorphous powder.

MS: m/e (% basis peak)=527 (M+, 1), 273 (44), 200 (7), 183 (12), 121 (9), 104 (5), 72 (100).

EXAMPLE 42

A solution of 6.60 g (0.014 mol) of rac-cis-2,3,3a,4,5,9b-hexahydro-3-(6-phthalimidohexyl)-1H-benzo[e]indol-6-yl-dimethylcarbamate and 7 ml (0.035 mol) of hydrazine hydrate in 200 ml of ethanol was boiled under reflux for 4 hours and stirred at room temperature over the weekend. After filtration the solvent was distilled off and the residue was dissolved in methylene chloride. The solution was extracted with water, the organic phase was dried with sodium sulphate, filtered and the filtrate was concentrated. 0.5 g of the 4.57 g of oil obtained was chromatographed over silica gel with methylene chloride/methanol/ammoniacal water 90:10:1. The oil obtained was dissolved in ethanol and treated with ethanolic HCl. Distillation of the solvent yielded 0.4 g of rac-3-(6-aminohexyl)-2,3,3a,4,5,9b-hexahydro-1H-cis-benzo[e]indol-6-yl dimethylcarbamate bishydrochloride as a beige amorphous solid.

MS: m/e (% basis peak)=359 (M+, 4), 273 (100), 259 (8), 72 (82).

EXAMPLE 43

A solution of 2.5 g (0.007 mol) of rac-3-(6-aminohexyl)-2,3,3a,4,5,9b-hexahydro-1H-cis-benzo[e]indol-6-yl dimethylcarbamate (crude product), 1.40 g (0.007 mol) of 4-(methanesulfonyl)benzoic acid, 2.65 g (0.007 mol) of 2-(1H-benzotriazol-1-yl)-1,1,3,3-tetramethyluronium hexafluorophosphate and 1.40 g (0.014 mol) of triethylamine in 50 ml of dimethylformamide was stirred at room temperature for 20 hours and then poured into aqueous sodium hydrogen carbonate solution, whereupon the mixture was extracted with methylene chloride. After drying with sodium sulphate and concentration the residue was chromatographed twice over silica gel, firstly with methylene chloride/methanol 20:1 and then with ethyl acetate/methanol 4:1. The resulting 1.8 g of solid were dissolved in methylene chloride, whereupon 0.5 ml of 8.2N ethanolic HCl was added. After drying over sodium sulphate, filtration and concentration there were obtained 1.96 g (49%) of rac-3-[6-(4-methanesulfonyl-benzoylamino)hexyl]-2,3,3a,4,5,9b-hexahydro-1H-cis-benzo[e]indol-6-yl-dimethylcarbamate as a amorphous solid.

MS: m/e (% basis peak)=541 (M+, 3), 448 (7), 273 (100), 183 (13), 121 (6), 107 (8), 72 (90).

EXAMPLE 44 a) A mixture of 30.0 g (0.07 mol) of rac-cis-N-[4-(1,2,3a,4,5,9b-hexahydro-6-methoxy-3H-benzo[e]indol-3-yl)butyl]phthalimide and 120 g (1.0 mol) of pyridine hydrochloride was treated with 10 drops of dimethylformamide and stirred at 180° for 18 hours. After cooling the mixture was suspended in aqueous sodium hydrogen carbonate solution and extracted with methylene chloride. The undissolved residue in the aqueous phase was filtered off and suspended in methanol to which 4 drops of 6N hydrochloric acid had been added. The undissolved constituent was filtered off and taken up in a mixture of methylene chloride/methanol about 1:1. The mixture was then filtered and the filtrate was concentrated. The thus-obtained dark oil (11.2 g) was dissolved in 100 ml of dimethylformamide and 36.3 ml (0.26 mol) of triethylamine and 15.1 ml (0.13 mol) of benzoyl chloride were added thereto. After stirring at room temperature overnight the mixture was treated with 2N sodium hydroxide solution, stirred for 30 minutes, 6N hydrochloric acid was added thereto until a pH value of 1 had been reached and the mixture was then adjusted to a pH value of about 8 with sodium hydrogen carbonate. Extraction with methylene chloride yielded 4.0 g of dark oil which was chromatographed over silica gel with methylene chloride/methanol 9:1. There were obtained 1.38 g of rac-N-[4-(6-hydroxy-2,3,3a,4,5,9b-hexahydro-1H-cis-benzo[e]indol-3-yl)butyl]-benzamide as a brown oil. A small sample was converted with an equimolar amount of ethanolic HCl into the hydrochloride.

MS: m/e (% basis peak)=364 (M+, 7), 202 (100), 188 (8), 171 (7), 145 (5), 105 (19).

b) A mixture of 1.18 g (0.001 mol) of rac-N-[4-(6-hydroxy-2,3,3a,4,5,9b-hexahydro-1H-cis-benzo[e]indol-3-yl)butyl]-benzamide, 0.36 ml (0.004 mol) of dimethylcarbamoyl chloride, 0.54 ml (0.004 mol) of triethylamine and 0.48 g (0.004 mol) of 4-dimetylaminopyridine in 60 ml of toluene was heated under reflux for 17 hours and then poured into aqueous sodium hydrogen carbonate solution, whereupon the mixture was extracted with ethyl acetate. Chromatography over silica gel with methylene chloride/methanol 20:1 yielded a solid which was dissolved in 30 ml of methylene chloride and treated with an equimolar amount of ethanolic HCl. After treatment with active charcoal and sodium sulphate the mixture was filtered and the solvent was distilled off. There was obtained 0.83 g (54%) of rac-cis-3-(4-benzoylaminobutyl)-2,3,3a,4,5,9b-hexahydro-1H-benzo[e]indol-6-yl dimethylcarbamate hydrochloride as a beige amorphous solid.

MS: m/e (% basis peak)=435 (M+, 7), 273 (100), 259 (8), 105 (27), 72 (61).

EXAMPLE 45

0.05 ml (0.43 mmol) of benzoyl chloride dissolved in 2 ml of methylene chloride was added dropwise to a solution of 0.15 g (0.36 mmol) of rac-3-(5-aminopentyl)-2,3,3a,4,5,9b-hexahydro-1H-cis-benzo[e]indol-6-yl dimethylcarbamate bis-hydrochloride and 0.06 ml (0.43 mmol) of triethylamine in 10 ml of methylene chloride and the mixture was stirred at room temperature for 1 hour. Then, the solvent was distilled off and the residue was chromatographed over silica gel with methylene chloride/methanol/ammoniacal water 110:8:1. The oil obtained was dissolved in ethanol and treated with ethanolic HCl. After concentration the residue was dissolved in methylene chloride, the solution was dried with sodium sulphate, filtered and the solvent was distilled off. There was obtained 0.11 g (63%) of rac-3-(5-benzoylaminopentyl)-2,3,3a,4,5,9b-hexahydro-1H-cis-benzo[e]indol-6-yl dimethylcarbamate hydrochloride as a beige amorphous solid.

MS: m/e (% basis peak)=449 (M+, 3), 273 (66), 200 (8), 105 (44), 77 (32), 72 (100).

EXAMPLE 46

0.6 ml of benzoyl chloride dissolved in 5 ml of methylene chloride was added dropwise to a solution of 1.50 g (0.004 mol) of rac-3-(6-aminohexyl)-2,3,3a,4,5,9b-hexahydro-1H-cis-benzo[e]indol-6-yl dimethylcarbamate and 0.7 ml (0.005 mol) of triethylamine in 70 ml of methylene chloride and the mixture was stirred at room temperature for 1 hour. The mixture was poured into aqueous sodium hydrogen carbonate solution, extracted with methylene chloride and chromatographed over silica gel with methylene chloride/methanol 20:1. The 1.24 g of solid obtained were dissolved in methylene chloride and treated with an equimolar amount of ethanolic HCl. After drying with sodium sulphate, filtration and distillation of the solvent in a vacuum there were obtained 1.14 g (55%) of rac-3-(6-benzoylamino-hexyl)-2,3,3a,4,5,9b-hexahydro-1H-cis-benzo[e]indol-6-yl-dimethylcarbamate hydrochloride as an amorphous foam.

MS: m/e (% basis peak)=463 (M+, 7), 273 (100), 105 (20), 72 (48).

EXAMPLE 47 a) A mixture of 10.0 g (0.049 mol) of rac-cis-2,3,3a,4,5,9b-hexahydro-6-methoxy-1H-benzo[e]indole, 7.44 g (0.054 mol) of potassium carbonate, 2.46 g (0.016 mol) of sodium iodide and 6.1 ml (0.054 mol) of benzyl chloride in 20 ml of ethyl methyl ketone was boiled under reflux for 24 hours and then poured into aqueous sodium hydrogen carbonate solution, whereupon the mixture was extracted with ethyl acetate. Chromatography over silica gel with methylene chloride/methanol 98:2 yielded 8.77 g (60%) of rac-3-benzyl-6-methoxy-2,3,3a,4,5,9b-hexahydro-1H-cis-benzo[e]indole as a colorless oil. A small sample was converted with ethanolic HCl into the hydrochloride; m.p. 203°–206°.

MS: m/e (% basis peak)=293 (M+, 82), 264 (4), 216 (15), 202 (26), 173 (15), 159 (15), 91 (100).

b) 8.55 g (0.029 mol) of rac-3-benzyl-6-methoxy-2,3,3a, 4,5,9b-hexahydro-1H-cis-benzo[e]indole in 100 ml of 48% aqueous hydrobromic acid was boiled under reflux for 1 hour and then the hydrobromic acid was distilled off in a vacuum. The residue was suspended in 30 ml of ice-cold water, whereupon the suspension was filtered. After drying the filtrate there were obtained 9.89 g (94%) of rac-3-benzyl-2,3,3a,4,5,9b-hexahydro-1H-cis-benzo[e]indol-6-ol hydrobromide as beige crystals with m.p. 237°–239°.

MS: m/e (% basis peak)=279 (M+, 79), 202 (17), 188 (28), 159 (19), 120 (13), 91 (100).

c) A mixture of 5.25 g (0.015 mol) of rac-3-benzyl-2,3,3a, 4,5,9b-hexahydro-1H-cis-benzo[e]indol-6-ol hydrobromide, 1.65 ml (0.018 mol) of dimethylcarbamoyl chloride, 6.3 ml (0.045 mol) of triethylamine and 2.20 g (0.018 mol) of 4-dimethylaminopyridine in 250 ml of toluene was boiled under reflux for 17 hours and then poured into aqueous sodium hydrogen carbonate solution, whereupon the mixture was extracted with ethyl acetate. Chromatography over silica gel with ethyl acetate/hexane 1:2 gave an oil (4.5 g) which was dissolved in 50 ml of methylene chloride. After the addition of 1.6 ml of 8.6M ethanolic HCl, treatment with active charcoal and sodium sulphate and filtration 100 ml of ethyl acetate were added thereto and the mixture was concentrated to a volume of about 40 ml. 4.43 g (76%) of rac-3-benzyl-2,3,3a,4,5,9b-hexahydro-1H-cis-benzo[e]indol-6-yl dimethylcarbamate hydrochloride with m.p. 177°–180° crystallized.

MS: m/e (% basis peak)=350 (M+, 40), 273 (7), 259 (9), 132 (16), 120 (7), 91 (76), 72 (100).

EXAMPLE 48

A solution of 0.60 g (0.0015 mol) of rac-N-[5-(cis-1,2,3a, 4,5,9b-hexahydro-6-hydroxy-3H-benzo[e]indol-3-yl)pentyl]phthalimide, 0.31 ml (0.002 mol) of triethylamine and 0.23 ml (0.003 mol) of ethyl isocyanate was heated under reflux for 4 hours, then concentrated and poured into water, whereupon the mixture was extracted with methylene chloride. The oil, which remained upon evaporation of the extract, was chromatographed over aluminum oxide (neutral) with methylene chloride. There was obtained 0.45 g of colorless oil which was converted with an equimolar amount of ethanolic hydrochloric acid into the hydrochloride. There was obtained 0.35 g (46%) of rac-3-[5-(1,3-dioxoisoindolin-2-yl)pentyl]-2,3,3a,4,5,9b-hexahydro-1H-cis-benzo[e]indol-6-yl ethylcarbamate hydrochloride as a white amorphous powder.

MS: m/e (% basis peak)=475 (M+, 2), 404 (8), 273 (28), 202 (100), 160 (9).

EXAMPLE 49 a) 4.0 g (0.01525 mol) of ethyl 1,2,3,4-tetrahydro-5-methoxy-2-oxo-1-naphthylacetate were dissolved in 80 ml of toluene, 3.0 ml (0.0305 mol) of cyclopentylamine were added thereto and the mixture was boiled for 40 hours on a water separator. After concentration the residue was hydrogenated with 1.2 g of Raney-nickel in 500 ml of ethanol at 120° and 140 bar for 10 hours. The product was chromatographed over silica gel with cyclohexane/ether 1:1. There were obtained 2.0 g (46%) of rac-cis-3-cyclopentyl-1,3,3a,4,5,9b-hexahydro-6-methoxy-2H-benzo[e]indol-2-one as white crystals with m.p. 84°–88°.

b) 0.53 g (0.014 mol) of lithium aluminum hydride was suspended in 25 ml of THF under argon. A solution of 2.0 g (0.007 mol) of rac-cis-3-cyclopentyl-1,3,3a,4,5,9b-hexahydro-6-methoxy-2H-benzo[e]indol-2-one in 50 ml of THF was added dropwise thereto and the mixture was boiled under reflux for 1 hour. 10 ml of a saturated aqueous NH4Cl solution was cautiously added dropwise thereto and the mixture was filtered. The filtrate was extracted with ethyl acetate, the organic phase was washed with water, dried with MgSO$_4$, filtered and the filtrate was concentrated. There were obtained 1.8 g (95%) of oily rac-cis-3-cyclopentyl-2,3,3a,4,5,9b-hexahydro-6-methoxy-1H-benzo[e]indole.

c) 1.8 g (0.0066 mol) of rac-cis-3-cyclopentyl-2,3,3a,4,5,9b-hexahydro-6-methoxy-1H-benzo[e]indole were dissolved in 0.2 l of 48% aqueous HBr and boiled under reflux for 1 hour. The mixture was cooled and concentrated, whereupon 100 ml of an aqueous NaHCO$_3$ solution and a small amount of 2N NaOH solution were added thereto, the mixture was extracted three times with CH$_2$Cl$_2$ and the extracts were dried with MgSO$_4$, filtered and concentrated. The brown crystals (1.7 g) were dissolved in 30 ml of ethanol. 1.3 ml (0.0075 mol) of 5.8N ethanolic HCl solution were added dropwise thereto and the mixture was stirred at room temperature for 1 hour and at 0° for 1 hour. The separated crystals were filtered off under suction and washed with ethyl acetate. There were obtained 1.65 g (85%) of rac-cis-3-cyclo-pentyl-2,3,3a,4,5,9b-hexahydro-1H-benzo[e]indol-6-ol hydro-chloride as pale rose crystals with m.p. 256°–258°.

d) 0.5 g (0.0017 mol) of rac-cis-3-cyclopentyl-2,3,3a,4,5,9b-hexahydro-1H-benzo[e]indol-6-ol hydrochloride dissolved in 30 ml of water was neutralized with 0.6 ml of 2N sodium hydroxide solution and extracted with ether. The organic phase was washed with water, dried over Na$_2$SO$_4$, filtered and the filtrate was concentrated. The solid residue was dissolved in 5 ml of hot THF, whereupon the solution was diluted with 45 ml of toluene. Then, 0.18 g (0.25 ml, 0.0018 mol) of triethylamine, 21 mg (170 mmol, 0.1 eq.) of 4-dimethylaminopyridine and finally dropwise 0.16 ml (0.0018 mol) of dimethyl chloroformamide were added thereto in succession. The mixture was boiled under reflux for 5 hours, then cooled, poured into water and extracted with toluene. The organic phase was washed with water, dried with Na$_2$SO$_4$, filtered, the filtrate was concentrated and the residue was chromatographed over 220 g of silica gel with methanol/ethyl acetate 9:1. The oil obtained (0.49 g) was dissolved in 10 ml of ethanol. 0.3 ml (0.0015 mol) of 4.93N ethanolic HCl solution was added dropwise thereto and the mixture was concentrated. The rac-cis-3-cyclopentyl-2,3,3a, 4,5,9b-hexahydro-1H-benzo[e]indol-6-yl dimethylcarbamate hydrochloride crystallized out from ethanol/ether. Yield: 0.47 g (84%), white crystals with m.p. 215°–217°.

EXAMPLE 50 a) A suspension of 150 g (0.7 mol) of 1,3,4,5-tetrahydro-6-methoxy-2H-benzo[e]indol-2-one in 1.5 l of methylene chloride was treated with 333 ml (2.1 mol) of triethylsilane and then slowly dropwise at 0° and while stirring with 240 ml of trifluoroacetic acid. After stirring for three hours 400 ml of 20% sodium hydroxide solution were added slowly while cooling until a pH of 14 had been reached. Subsequently, the mixture was poured into water and extracted with methylene chloride. The organic phase was washed with sodium chloride solution, dried with sodium sulphate, filtered and evaporated. The residue was treated with 500 ml of ether, whereupon the solid was filtered off and dried at 50°/20 Torr. There were obtained 123 g (81%) of rac-cis-1,3,3a,4,5,9b-hexahydro-6-methoxy-2H-benzo[e]indol-2-one with m.p. 192°–194°. The material showed a Rf value of 0.14 in a thin-layer chromatogram (silica gel, ethyl acetate).

From 1 g of the material there could be isolated by chromatography on silica gel with ethyl acetate/hexane 1:2 15 mg of rac-trans-1,3,3a,4,5,9b-hexahydro-6-methoxy-2H-benzo[e]indol-2-one with m.p. 265°–270°, which showed a Rf value 0.27 in a thin-layer chromatogram (silica gel, ethyl acetate).

b) From 64.1 g of the above material there were obtained analogously to that described in Example 1c) using 22.4 g of lithium aluminum hydride 58.8 g (98%) of a grey oil which crystallized in a refrigerator; m.p. of the hydrochloride 226°–231°.

c) From a total of 337 g of the above material and a total of 394 g 2-cyclohexylethyl bromide there were obtained analogously to that described in Example 1d) in two batches a total of 626 g of a brown oil containing solid particles from which there were obtained by treatment of ethanolic HCl a total of 413 g (71%) of colorless crystals of the corresponding hydrochloride.

d) From 155 g of the above material there were obtained analogously to that described in Example 1e) 144 g of a brown oil.

e) A solution of 234 g (−)-2,2′-(1,1-binaphthyl)phosphoric acid in 2.35 l of ethanol and 1.55 l of chloroform was warmed and treated with a solution of 336 g of the material obtained according to Example 50d) in 500 ml of ethanol. 2.4 l of solvent, mainly chloroform, were then distilled off, whereupon the solution was cooled and crystallization set in. The suspension was stored in a refrigerator over the weekend and then filtered. The filter residue was washed with ethyl acetate and ether and dried at 50°/20 Torr, whereby there were obtained 463 g of colorless crystals, the enantiomeric ratio of which (according to gas chromatography after extraction of a 300 mg of sample with aqueous ammonia/ether) was 63% of the (+) enantiomer and 37% of the (−) enantiomer.

The material obtained was dissolved in 3 l of ethanol and 4.2 l of chloroform while warming. Then, 1.3 l of chloroform were distilled off, whereupon crystallization set in upon stirring overnight at room temperature. The suspension was cooled to 0° and then filtered. The filter residue was washed with ethyl acetate and ether and dried at 50°/20 Torr. There were obtained 253 g of colorless crystals; enantiomer ratio 89:11. The mother liquor was concentrated to a volume of about 2 l and there were obtained a further 200 g of colorless crystals. The two crystal fractions were combined and it was subsequently found that the enantiomer ratio of this second crystallization was 48:52.

A third crystallization (2.5 l of ethanol and 3.5 l of chloroform) yielded 288 g of crystals; enantiomer ratio 89:11.

A fourth crystallization (2.3 l of ethanol and 3.5 l of chloroform) yielded 239 g of crystals; enantiomer ratio 97:3.

A fifth crystallization (2 l of ethanol and 4 l of chloroform) yielded 229 g of crystals; enantiomer ratio 98:8:1.2.

A sixth crystallization (1.8 l of ethanol and 4.5 l of chloroform) yielded 222 g of crystals; enantiomer ratio 99:4:0.6.

A seventh crystallization (1.7 l of ethanol and 4.5 l of chloroform) yielded 217 g of crystals; enantiomer ratio 99.6:0.4.

An eighth crystallization (1.7 l of ethanol and 4.5 l of chloroform) yielded 212 g of crystals; enantiomer ratio 99.85:0.15.

The material obtained was suspended in about 5 l of ethyl acetate and extracted with a mixture of about 4 l of water and 4 l of 25% ammonium hydroxide solution. The organic phase was extracted six times with 2.5% ammonium hydroxide solution and all aqueous phases were extracted three times with ethyl acetate. The combined organic phases were dried with sodium sulphate and evaporated, and there were obtained 86.4 g (51%) of crystalline material.

f) A suspension of 70 g (0.23 mol) of the resulting material in 2 l of toluene was treated with 39 ml (0.28 mol) of triethylamine and 34.3 g (0.28 mol) of 4-dimethylaminopyridine. 25.3 ml (0.28 mol) of dimethylcarbamoyl chloride were added to the resulting homogeneous mixture. Then, the mixture was heated at reflux for 4 hours, whereupon the solvent was evaporated, the residue was taken up in ethyl acetate and the solution was extracted firstly twice with water and then with sodium chloride solution. The aqueous phases were extracted three times with ethyl acetate, whereupon the organic phases were combined, dried with sodium sulphate, filtered and evaporated. The oil (103 g) remaining as the residue was chromatographed on 3 kg of silica gel with ethyl acetate/n-hexane 1:1.

There were thus obtained as the first product 80.8 g (85%) of a colorless oil which was taken up in 200 ml of ethanol and treated with 30 ml of 8.6M ethanolic HCl while cooling in an ice bath. The pale red solution was evaporated and the residue was again taken up in 600 ml of ethanol, whereupon the solution, after treatment with 8 g of active charcoal and filtration, was evaporated. The residue was taken up in 600 ml of ethyl acetate, whereupon the solid was filtered off and dried at 50°/20 Torr. There were obtained 75 g (79%) of (+)-cis-3-(2-cyclohexylethyl)-2,3,3a,4,5,9b-hexahydro-1H-benzo[e]indol-6-yl dimethylcarbamate hydrochloride in the form of colorless crystals with m.p. 205°–207°; $[\alpha]_D^{20} = +28.97°$ (c=0.7% in methanol).

As the second product there were obtained 5.5 g of (+)-trans-3-(2-cyclohexylethyl)-2,3,3a,4,5,9b-hexahydro-1H-benzo[e]indol-6-yl dimethylcarbamate with m.p. 110°–112°; $[\alpha]_D^{20} = +7.6°$ (c=0.8% in methanol).

EXAMPLE A

Compounds in accordance with the invention and/or pharmaceutically acceptable acid addition salts thereof can be used as described hereinafter as active ingredients for the manufacture of galenical administration forms.

a) 5 mg soft gelatine capsules:

| Composition: | Per capsule |
| --- | --- |
| Active ingredient | 5.0 mg |
| Yellow wax | 8.0 mg |
| Hydrogenated soya bean oil | 8.0 mg |
| Partially hydrogenated vegetable oil | 34.0 mg |
| Soya bean oil | 110.0 mg |
| Weight of capsule content | 165.0 mg |

The active ingredient is dissolved in a warm melt of the remaining materials while taking appropriate precautions. The solution is filled by machine into soft gelatine capsules of suitable size.

b) 20 mg hard gelatine capsules:

| Composition: | Per capsule |
| --- | --- |
| Active ingredient | 20.0 mg |
| Cryst. lactose | 37.0 mg |
| Microcrystalline cellulose | 20.0 mg |
| Crospovidone | 8.5 mg |
| Modified starch | 8.5 mg |
| Talc | 4.5 mg |
| Magnesium stearate | 1.5 mg |
| Weight of capsule content | 100.0 mg |

The sieved and mixed ingredients are filled into capsules of suitable size.

c) 200 mg coated tablets:

| Composition: | Per tablet |
| --- | --- |
| Tablet care: | |
| Active ingredient | 200.0 mg |
| Microcrystalline cellulose | 23.5 mg |
| Polyvinylpyrrolidone | 12.5 mg |
| Modified starch | 12.5 mg |
| Magnesium stearate | 1.5 mg |
| Core weight | 250.0 mg |
| Coating: | |
| Hydroxypropylmethylcellulose | 3.5 mg |
| Polyethylenglycol 6000 | 0.8 mg |
| Talc | 1.3 mg |
| Yellow iron oxide | 0.8 mg |
| Titanium dioxide | 0.8 mg |
| Coating weight | 7.4 mg |

The sieved active ingredient is mixed with the microcrystalline cellulose. The mixture is granulated with a solution of polyvinylpyrrolidone in water. The granulate is mixed with the modified starch and magnesium stearate. The mixture is pressed to cores weighing 250 mg. The cores are coated with a solution/suspension of the aforementioned composition.

d) 50 mg Sachets:

| Composition: | Per sachet |
| --- | --- |
| Active ingredient | 50.0 mg |
| Finely powdered lactose | 1015.0 mg |
| Microcrystalline cellulose | 1400.0 mg |
| Sodium carboxymethylcellulose | 14.0 mg |
| Polyvinylpyrrolidone | 10.0 mg |
| Magnesium stearate | 10.0 mg |
| Flavorant | 1.0 mg |
| Sachet fill weight | 2500.0 mg |

The active ingredient is mixed with the lactose, microcrystalline cellulose and sodium carboxymethylcellulose. The mixture is granulated with a solution of polyvinylpyrrolidone in water. The granulate is mixed with the magnesium stearate and flavorants. The mixture is filled into sachets of suitable size.

We claim:

1. A cis-2,3,3a,4,5,9b-Hexahydro-1H-benzo[e]indole derivative of the formula

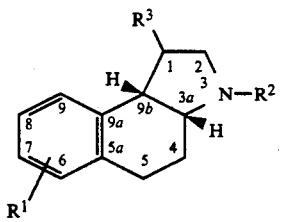

wherein R¹ is a residue of the formula —O—CO—NR⁴R⁵, R² is lower alkyl, lower cycloalkyl or lower alkyl substituted by lower cycloalkyl, aryl, aroyl, aroylamino, amino or by a cyclic amino, amide or imide group, R³ is hydrogen or lower alkyl, R⁴ is lower alkyl and R⁵ is hydrogen or lower alkyl, the corresponding trans isomer or cis-trans isomeric mixture, or a pharmaceutically acceptable salt thereof.

2. A cis-2,3,3a,4,5,9b-Hexahydro-1H-benzo[b]indole derivative, according to claim 1, wherein R² is lower alkyl or lower alkyl substituted by lower cycloalkyl, aryl, aroyl, aroylamino, amino or by a cyclic amino, amide or imide group, or a pharmaceutically acceptable acid addition salt thereof.

3. A compound, according to claim 1, wherein R¹ is in the 6- or 9-position.

4. A compound, according to claim 3, wherein R⁴ is methyl, ethyl, propyl or butyl and R⁵ is hydrogen or R⁴ is methyl and R⁵ is ethyl or R⁴ and R⁵ both are methyl.

5. A compound, according to claim 4, wherein R² is n-propyl, 3-methylbutyl, cyclopentyl, cyclohexylmethyl, 2-cyclohexylethyl, 3-cyclohexylpropyl, 4-cyclohexylbutyl, 2-cyclopentylethyl, benzyl, 2-phenylethyl, 3-phenylpropyl, 3-benzoylpropyl, 4-benzoylbutyl, 3-(4-methoxybenzoyl)propyl, 4-(3,4-dimethoxybenzoyl)butyl, 5-(3,4-dimethoxybenzoyl)pentyl, 3-(4-fluorobenzoyl)propyl, 4-benzoylaminobutyl, 5-benzoylamino-pentyl, 6-benzoylaminohexyl, 4-(4-methanesulphonylbenzoyl-amino)butyl, 5-(4-methanesulphonylbenzoylamino)pentyl, 6-(4-methanesulphonylbenzoylamino)hexyl, 4-aminobutyl, 5-amino-pentyl, 6-aminohexyl, 2-morpholin-4-ylethyl, 3-morpholin-4-ylpropyl, 2-piperidin-1-ylethyl, 3-piperidin-1-ylpropyl, 4-(1,3-dioxoisoindolin-1-yl)butyl, 5-(1,3-dioxoisoindolin-1-yl)pentyl, 6-(1,3-dioxoisoindolin-1-yl)hexyl, 5-(1,3-dioxo-octahydro-cis-isoindolin-2-yl)pentyl, 4-(4,4-dimethyl-2,6-dioxopiperidin-1-yl)butyl, 5-(4,4-dimethyl-2,6-dioxopiperidin-1-yl)pentyl, 6-(4,4-dimethyl-2,6-dioxopiperidin-1-yl)hexyl, 4-(1-oxoisoindolin-2-yl)butyl, 5-(1-oxoisoindolin-2-yl)pentyl or 6-(1-oxoisoindolin-2-yl)pentyl.

6. A compound, according to claim 5, wherein R³ is hydrogen or methyl.

7. A compound, according to claim 1, (+)-cis-3-(2-Cyclohexylethyl)-2,3,3a,4,5,9b-hexahydro-1H-benzo[e]indol-6-yl dimethylcarbamate.

8. A compound, according to claim 1, (−)-cis-3-(2-Cyclohexylethyl)-2,3,3a,4,5,9b-hexahydro-1H-benzo[e]indol-6-yl dimethylcarbamate.

9. A compound, according to claim 1, rac-cis-3-(2-Cyclohexylethyl)-2,3,3a,4,5,9b-hexahydro-1H-benzo[e]indol-6-yl dimethylcarbamate.

10. A compound, according to claim 1, rac-cis-2,3,3a,4,5,9b-Hexahydro-3-(4-phthalimidobutyl)-1H-benzo[e]indol-6-yl dimethylcarbamate.

11. A compound, according to claim 1, rac-cis-2,3,3a,4,5,9b-Hexahydro-3-(6-phthalimidohexyl)-1H-benzo[e]indol-6-yl dimethylcarbamate.

12. A compound, according to claim 1, rac-cis-2,3,3a,4,5,9b-Hexahydro-3-(2-morpholinoethyl)-1H-benzo[e]indol-6-yl dimethylcarbamate.

13. A compound, according to claim 1, rac-2,3,3aα,4,5,9bα-Hexahydro-1α-methyl-3-propyl-1H-benzo[e]indol-6-yl dimethylcarbamate.

14. A compound, according to claim 1, selected from the group consisting of rac-cis-2,3,3a,4,5,9b-Hexahydro-3-propyl-1H-benzo[e]indol-9-yl dimethylcarbamate, (+)-3-(2-cyclohexylethyl)-cis-2,3,3a,4,5,9b-hexahydro-1H-benzo[e]indol-6-yl methylcarbamate, (+)-3-(2-cyclohexylethyl)-cis-2,3,3a,4,5,9b-hexahydro-1H-benzo[e]indol-6-yl propylcarbamate, (+)-3-(2-cyclohexylethyl)-cis-2,3,3a,4,5,9b-hexahydro-1H-benzo[e]indol-6-yl ethylmethylcarbamate, rac-3-cyclohexylmethyl-cis-2,3,3a,4,5,9b-hexahydro-1H-benzo[e]indol-6-yl dimethylcarbamate, rac-3-(3-cyclohexylpropyl)-cis-2,3,3a,4,5,9b-hexahydro-1H-benzo[e]indol-6-yl dimethylcarbamate, rac-3-(4-cyclohexylbutyl)-cis-2,3,3a,4,5,9b-hexahydro-1H-benzo[e]indol-6-yl dimethylcarbamate and rac-3-(2-cyclopentylethyl)-cis-2,3,3a,4,5,9b-hexahydro-1H-benzo[e]indol-6-yl dimethylcarbamate.

15. A pharmaceutial composition comprising a therapeutically effective amount of a cis-2,3,3a,4,5,9b-Hexahydro-1H-benzo[e]indole derivative of the formula

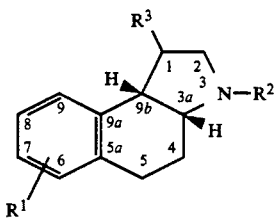

wherein R¹ is a residue of the formula —O—CO—NR⁴R⁵, R² is lower alkyl, lower cycloalkyl or lower alkyl substituted by lower cycloalkyl, aryl, aroyl, aroylamino, amino or by a cyclic amino, amide or imide group, R³ is hydrogen or lower alkyl, R⁴ is lower alkyl and R⁵ is hydrogen or lower alkyl, the corresponding trans isomer or cis-trans isomeric mixture, or pharmaceutically acceptable salt thereof, and an inert carrier.

16. A pharmaceutical composition, according to claim 15, wherein R² is lower alkyl or lower alkyl substituted by lower cycloalkyl, aryl, aroyl, aroylamino, amino or by a cyclic amino, amide or imide group, or a pharmaceutically acceptable acid addition salt thereof.

17. A pharmaceutical composition, according to claim 15, wherein R¹ is in the 6- or 9-position.

18. A pharmaceutical composition, according to claim 17, wherein R⁴ is methyl, ethyl, propyl or butyl and R⁵ is hydrogen or R⁴ is methyl and R⁵ is ethyl or R⁴ and R⁵ both are methyl.

19. A pharmaceutical composition, according to claim 18, wherein R² is n-propyl, 3-methylbutyl, cyclopentyl, cyclohexylmethyl, 2-cyclohexylethyl, 3-cyclohexylpropyl, 4-cyclohexyl-butyl, 2-cyclopentylethyl, benzyl, 2-phenylethyl, 3-phenylpropyl, 3-benzoylpropyl, 4-benzoylbutyl, 3-(4-methoxybenzoyl)propyl, 4-(3,4-dimethoxybenzoyl)butyl, 5-(3,4-dimethoxybenzoyl)pentyl, 3-(4-fluorobenzoyl)propyl, 4-benzoylaminobutyl, 5-benzoylaminopentyl, 6-benzoylaminohexyl, 4-(4-methanesulphonylbenzoylamino)butyl, 5-(4-methanesulphonylbenzoylamino)pentyl, 6-(4-methanesulphonylbenzoylamino)hexyl, 4-aminobutyl, 5-aminopentyl, 6-aminohexyl, 2-morpholin-4-ylethyl, 3-morpholin-4-ylpropyl, 2-piperidin-1-ylethyl, 3-piperidin-1-ylpropyl, 4-(1,3-dioxoisoindolin-1-yl)butyl, 5-(1,3-dioxoisoindolin-1-yl)pentyl, 6-91,3-dioxoisoindolin-1-yl)hexyl, 5-(1,3-dioxo-octahydro-cis-isoindolin-2-yl)pentyl, 4-(4,4-dimethyl-2,6-dioxopiperidin-1-yl)butyl, 5-(4,4-dimethyl-2,6-dioxopiperidin-1yl)pentyl, 6-(4,4-dimethyl-2,6-dioxopiperidin-1-yl)hexyl, 4-(1-oxoisoindolin-2-yl)butyl, 5-(1-oxoisoindolin-2-yl)pentyl or 6-(1-oxoisoindolin-2-yl)pentyl.

20. A pharmaceutical composition, according to claim 19, wherein R$^3$ is hydrogen or methyl.

21. A pharmaceutical composition, according to claim 15, wherein the compound of formula I is (+)-cis-3-(2-Cyclohexyl-ethyl)-2,3,3a,4,5,9b-hexahydro-1H-benzo[e]indol-6-yl dimethyl-carbamate.

22. A pharmaceutical composition, according to claim 15, wherein the compound of formula I is (−)-cis-3-(2-Cyclohexyl-ethyl)-2,3,3a,4,5,9b-hexahydro-1H-benzo[e]indol-6-yl dimethyl-carbamate.

23. A pharmaceutical composition, according to claim 15, wherein the compound of formula I is rac-cis-3-(2-Cyclohexylethyl)-2,3,3a,4,5,9b-hexahydro-1H-benzo[e]indol-6-yl dimethylcarbamate.

24. A pharmaceutical composition, according to claim 15, wherein the compound of formula I is rac-cis-2,3,3a,4,5,9b-Hexahydro-3-(4-phthalimidobutyl)-1H-benzo[e]indol-6-yl dimethylcarbamate.

25. A pharmaceutical composition, according to claim 15, wherein the compound of formula I is rac-cis-2,3,3a,4,5,9b-Hexahydro-3-(6-phthalimidohexyl)-1H-benzo[e]indole-6-yl dimethylcarbamate.

26. A pharmaceutical composition, according to claim 15, wherein the compound of formula I is rac-cis-2,3,3a, 4,5,9b-Hexahydro-3-(2-morpholinoethyl)-1H-benzo[e]indol-6-yl dimethylcarbamate.

27. A pharmaceutical composition, according to claim 15, wherein the compound of formula I is rac-2,3,3a$\alpha$,4,5,9b$\alpha$-Hexahydro-1$\alpha$-methyl-3-propyl-1H-benzo[e]indol-6-yl dimethylcarbamate.

* * * * *